(12) United States Patent
Hyde et al.

(10) Patent No.: US 11,084,015 B2
(45) Date of Patent: Aug. 10, 2021

(54) FORMATION OF ARRAY OF MEMBRANES AND APPARATUS THEREFOR

(71) Applicant: Oxford Nanopore Technologies Ltd., Oxford (GB)

(72) Inventors: Jason Robert Hyde, Oxford (GB); Pedro Miguel Ortiz Bahamon, Oxford (GB); Clive Gavin Brown, Cambridge (GB); Andrew John Heron, Oxford (GB); Paul Raymond Mackett, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 17/060,027

(22) Filed: Sep. 30, 2020

(65) Prior Publication Data

US 2021/0086160 A1 Mar. 25, 2021

Related U.S. Application Data

(63) Continuation of application No. 14/438,705, filed as application No. PCT/GB2013/052766 on Oct. 23, 2013, now Pat. No. 10,814,298.

(Continued)

(30) Foreign Application Priority Data

Jul. 23, 2013 (GB) ..................................... 1313121

(51) Int. Cl.
*G01N 1/18* (2006.01)
*B01J 19/00* (2006.01)
(Continued)

(52) U.S. Cl.
CPC ......... *B01J 19/0046* (2013.01); *B01L 3/5088* (2013.01); *C12Q 1/6869* (2013.01);
(Continued)

(58) Field of Classification Search
CPC ............. B01L 2300/165; B01L 3/5088; G01N 33/54353
(Continued)

(56) References Cited

U.S. PATENT DOCUMENTS 3,799,743 A 3/1974 Alexander et al.
4,154,795 A 5/1979 Thorne
(Continued)

FOREIGN PATENT DOCUMENTS

CN 103995035 A 8/2014
JP 2014-190891 A 10/2014
(Continued)

OTHER PUBLICATIONS

Extended European Search Report for Application No. EP 19203649.9 dated Dec. 17, 2019.
(Continued)

*Primary Examiner* — Natalia Levkovich
(74) *Attorney, Agent, or Firm* — Wolf, Greenfield & Sacks, P.C.

(57) ABSTRACT

An array of membranes comprising amphipathic molecules is formed using an apparatus comprising a support defining an array of compartments. Volumes comprising polar medium are provided within respective compartments and a layer comprising apolar medium is provided extending across the openings with the volumes. Polar medium is flowed across the support to displace apolar medium and form a layer in contact with the volumes, forming membranes comprising amphipathic molecules at the interfaces. In one construction of the apparatus, the support that comprises partitions which comprise inner portions and outer portions. The inner portions define inner recesses without gaps therebetween that are capable of constraining the volumes comprising polar medium contained in neighbour-
(Continued)

ing inner recesses from contacting each other. The outer portions extend outwardly from the inner portions and have gaps allowing the flow of an apolar medium across the substrate.

7 Claims, 38 Drawing Sheets

Specification includes a Sequence Listing.

Related U.S. Application Data

(60) Provisional application No. 61/718,899, filed on Oct. 26, 2012.

(51) Int. Cl.
| | | |
|---|---|---|
| G01N 33/487 | (2006.01) | |
| B01L 3/00 | (2006.01) | |
| C12Q 1/6869 | (2018.01) | |
| G01N 33/573 | (2006.01) | |

(52) U.S. Cl.
CPC ..... *G01N 33/48721* (2013.01); *G01N 33/573* (2013.01); *B01J 2219/00313* (2013.01); *B01J 2219/00317* (2013.01); *B01J 2219/00351* (2013.01); *B01J 2219/00585* (2013.01); *B01J 2219/00659* (2013.01); *B01J 2219/00734* (2013.01); *B01J 2219/00736* (2013.01); *B01L 2200/0642* (2013.01); *B01L 2400/086* (2013.01); *G01N 2333/974* (2013.01)

(58) Field of Classification Search
USPC .......................................... 436/180, 178, 174
See application file for complete search history.

(56) References Cited

U.S. PATENT DOCUMENTS

| | | | |
|---|---|---|---|
| 5,234,566 | A | 8/1993 | Osman et al. |
| 5,403,451 | A | 4/1995 | Riviello et al. |
| 6,056,922 | A | 5/2000 | Ikematsu |
| 6,300,141 | B1 | 10/2001 | Segal et al. |
| 6,479,288 | B1 | 11/2002 | Laffafian et al. |
| 6,503,452 | B1 | 1/2003 | Boxer et al. |
| 6,699,697 | B2 | 3/2004 | Klemic et al. |
| 6,863,833 | B1 | 3/2005 | Bloom et al. |
| 6,913,697 | B2 | 7/2005 | Lopez et al. |
| 6,916,488 | B1 | 7/2005 | Meier et al. |
| 7,077,939 | B1 | 7/2006 | Crooks et al. |
| 7,144,486 | B1 | 12/2006 | Fritsch et al. |
| 7,169,272 | B2 | 1/2007 | Fritsch et al. |
| 7,745,116 | B2 | 6/2010 | Williams |
| 7,939,270 | B2 | 5/2011 | Holden et al. |
| 8,124,191 | B2 | 2/2012 | Ervin et al. |
| 8,461,854 | B2 | 6/2013 | Chen et al. |
| 9,546,400 | B2 | 1/2017 | Turner et al. |
| 9,678,056 | B2 | 6/2017 | Turner et al. |
| 9,927,398 | B2 | 3/2018 | Reid et al. |
| 10,215,768 | B2 | 2/2019 | Sanghera et al. |
| 10,338,056 | B2 | 7/2019 | Hyde et al. |
| 10,416,117 | B2 | 9/2019 | Reid et al. |
| 10,549,274 | B2 | 2/2020 | Brown et al. |
| 2002/0074227 | A1 | 6/2002 | Nisch et al. |
| 2002/0123048 | A1 | 9/2002 | Gau |
| 2003/0015422 | A1 | 1/2003 | Fritsch et al. |
| 2003/0075445 | A1 | 4/2003 | Woudenberg et al. |
| 2003/0098248 | A1 | 5/2003 | Vogel et al. |
| 2003/0111340 | A1 | 6/2003 | Cheng et al. |
| 2003/0148401 | A1 | 8/2003 | Agrawal et al. |
| 2003/0224523 | A1 | 12/2003 | Thornberg et al. |
| 2004/0171169 | A1 | 9/2004 | Kallury et al. |
| 2005/0014162 | A1 | 1/2005 | Barth et al. |
| 2005/0230272 | A1 | 10/2005 | Lee et al. |
| 2006/0079009 | A1 | 4/2006 | Salmon et al. |
| 2006/0163063 | A1 | 7/2006 | Picollet-Dahan et al. |
| 2006/0257941 | A1 | 11/2006 | McDevitt et al. |
| 2007/0035308 | A1 | 2/2007 | Ide |
| 2007/0161101 | A1 | 7/2007 | Takeuchi |
| 2008/0254995 | A1 | 10/2008 | Kim et al. |
| 2009/0142504 | A1 | 6/2009 | Ervin et al. |
| 2009/0167288 | A1 | 7/2009 | Reid et al. |
| 2010/0035349 | A1 | 2/2010 | Bau et al. |
| 2010/0147450 | A1 | 6/2010 | Takeuchi et al. |
| 2010/0190253 | A1 | 7/2010 | Tazaki et al. |
| 2010/0304980 | A1 | 12/2010 | Takeuchi et al. |
| 2011/0120871 | A1 | 5/2011 | Reid et al. |
| 2011/0121840 | A1 | 5/2011 | Sanghera et al. |
| 2011/0214991 | A1 | 9/2011 | Kim et al. |
| 2011/0274737 | A1 | 11/2011 | Palmaz |
| 2011/0287414 | A1 | 11/2011 | Chen et al. |
| 2011/0318774 | A1 | 12/2011 | Larsen |
| 2012/0010085 | A1 | 1/2012 | Rava et al. |
| 2013/0071932 | A1 | 3/2013 | Itchoda et al. |
| 2013/0140192 | A1 | 6/2013 | Behrends et al. |
| 2013/0196442 | A1 | 8/2013 | Momose et al. |
| 2013/0207205 | A1 | 8/2013 | Chen |
| 2013/0217106 | A1 | 8/2013 | Jones |
| 2013/0270521 | A1 | 10/2013 | Peng et al. |
| 2014/0243214 | A1 | 8/2014 | Haga et al. |
| 2014/0255921 | A1 | 9/2014 | Moysey et al. |
| 2014/0296083 | A1 | 10/2014 | Brown et al. |
| 2014/0318964 | A1 | 10/2014 | Dunbar et al. |
| 2014/0329693 | A1 | 11/2014 | Reid et al. |
| 2014/0335512 | A1 | 11/2014 | Moysey et al. |
| 2014/0346059 | A1 | 11/2014 | Akeson |
| 2014/0346515 | A1 | 11/2014 | Yanagi et al. |
| 2015/0014160 | A1 | 1/2015 | Hyde et al. |
| 2015/0065354 | A1 | 3/2015 | Moysey et al. |
| 2015/0191709 | A1 | 7/2015 | Heron et al. |
| 2015/0198611 | A1 | 7/2015 | Ostrowski et al. |
| 2015/0204763 | A1 | 7/2015 | Stelzle et al. |
| 2015/0218629 | A1 | 8/2015 | Heron et al. |
| 2015/0268256 | A1 | 9/2015 | Sanghera et al. |
| 2015/0300986 | A1 | 10/2015 | Reid et al. |
| 2016/0040230 | A1 | 2/2016 | Akeson et al. |
| 2016/0231307 | A1 | 8/2016 | Xie |
| 2016/0257942 | A1 | 9/2016 | Bruce et al. |
| 2017/0189906 | A1 | 7/2017 | Moll et al. |
| 2017/0326550 | A1 | 11/2017 | Brown et al. |
| 2017/0363577 | A1 | 12/2017 | Reid et al. |
| 2018/0321188 | A1 | 11/2018 | Reid et al. |
| 2019/0210021 | A1 | 7/2019 | Waterman |
| 2019/0242913 | A1 | 8/2019 | Sanghera et al. |
| 2019/0391128 | A1 | 12/2019 | Hyde et al. |
| 2020/0292521 | A1 | 9/2020 | Xie et al. |

FOREIGN PATENT DOCUMENTS

| | | |
|---|---|---|
| WO | WO 1988/008534 A1 | 11/1988 |
| WO | WO 1999/013101 A1 | 3/1999 |
| WO | WO 2000/013014 A1 | 3/2000 |
| WO | WO 2005/124888 A1 | 12/2005 |
| WO | WO 2016/172724 A1 | 10/2016 |
| WO | WO 2018/007819 A1 | 1/2018 |
| WO | WO 2019/063959 A1 | 4/2019 |

OTHER PUBLICATIONS

International Search Report and Written Opinion for Application No. PCT/GB2013/052766, dated Apr. 22, 2014.
International Preliminary Report on Patentability for Application No. PCT/GB2013/052766, dated May 7, 2015.
Ivanov et al., DNA tunneling detector embedded in a nanopore. Nano Lett. 2011;11(1):279-285. doi:10.1021/nl103873a.
U.S. Appl. No. 16/816,221, filed Mar. 11, 2020, Xie et al.
U.S. Appl. No. 16/768,642, filed May 29, 2020, Waterman.

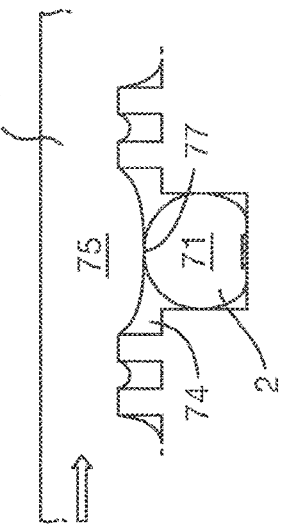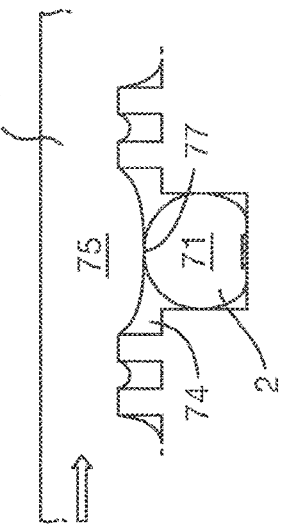

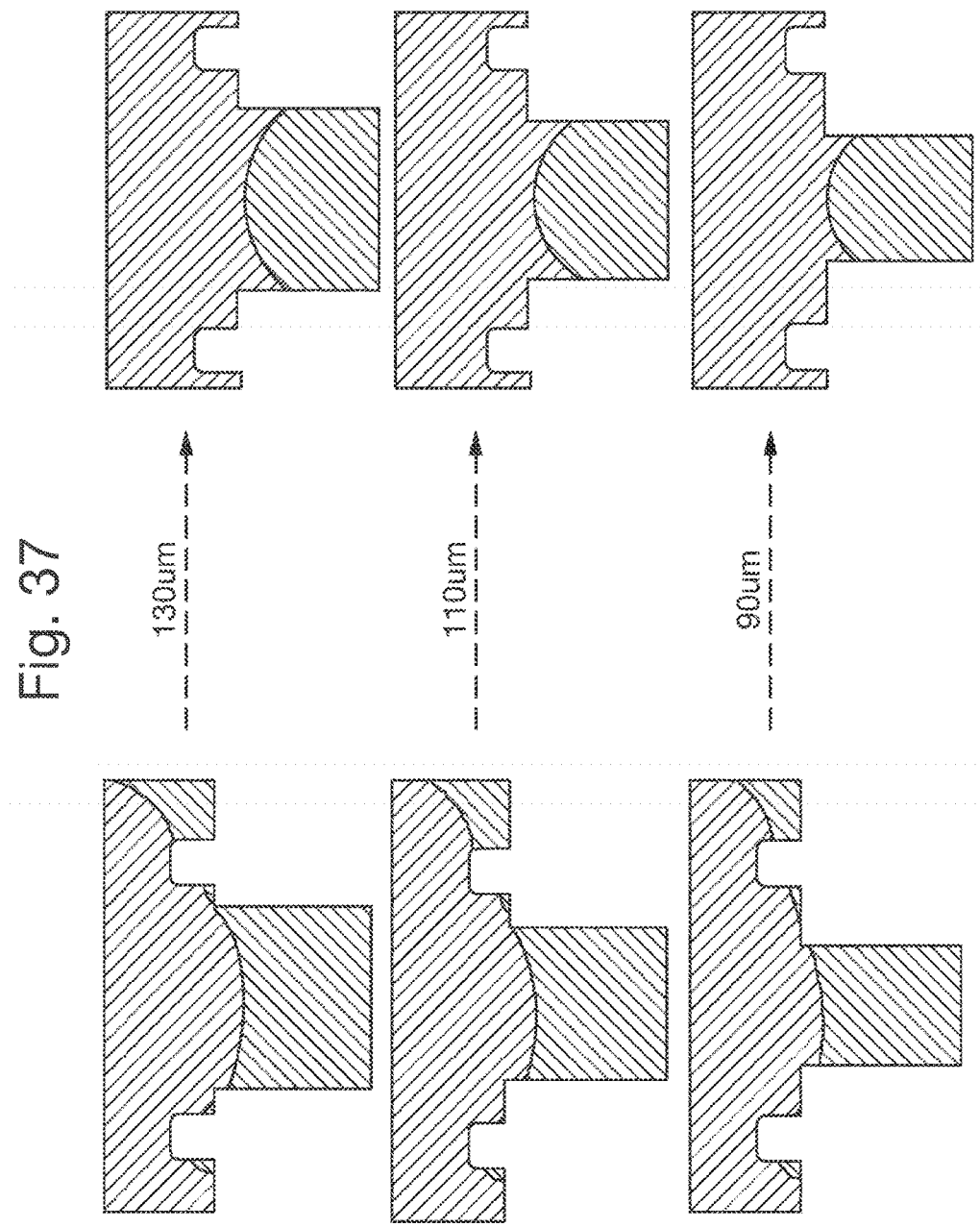

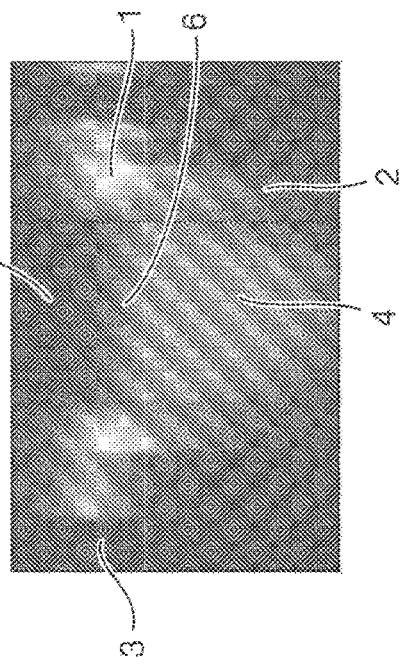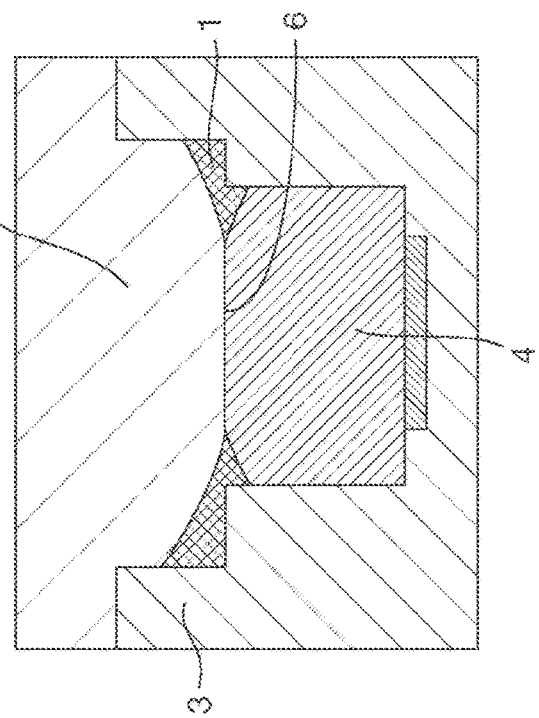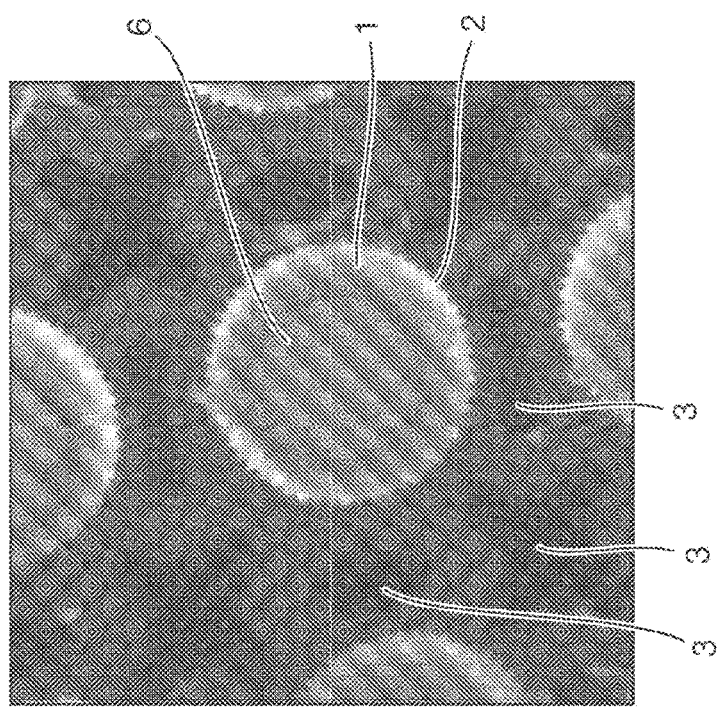

FORMATION OF ARRAY OF MEMBRANES AND APPARATUS THEREFOR

RELATED APPLICATIONS

This application is a continuation of U.S. patent application Ser. No. 14/438,705, filed Apr. 27, 2015, which is a national stage filing under 35 U.S.C. § 371 of International Application Number PCT/GB2013/052766, filed Oct. 23, 2013, which claims the benefit of priority under 35 U.S.C. § 119(e) to U.S. Provisional Patent Application No. 61/718, 899, filed Oct. 26, 2012, and which claims priority to United Kingdom Patent Application Number 1313121.4, filed Jul. 23, 2013, the entire contents of each of which applications are incorporated herein by reference in their entirety for all purposes.

In some aspects, the present invention relates to the formation of an array of membranes comprising amphipathic molecules using an array of volumes of polar medium. A further aspect relates to an apparatus suitable for forming an array of membranes. In other aspects, the present invention relates to the formation of an array of volumes of polar medium. Such an array of volumes of a polar medium may be used in a range of applications, including the formation of membranes comprising amphipathic molecules.

Spatially defined arrays of small volumes of fluid in the nanolitre to picolitre range may be used in a wide range of biological, pharmaceutical and other analytical applications. A droplet array provides the opportunity to facilitate high throughput processing of small volumes of individual droplets or groups of droplets and may be used for example to compartmentalise reactions, cell sorting and screening applications such as protein crystallisation, analysis of blood or spinal fluid and waste processing. The ability to address and replace the volumes of fluid in the array is an important aspect, for example for carrying out reactions on the volumes and replenishing the array. Microfluidic static droplet arrays are disclosed in Lab Chip, 2011, 11, 3949.

Lipid bilayers are thin polar membranes formed from two layers of lipid molecules. Lipid bilayers are found in cell membranes of most living organisms and are usually composed of phospholipids. They are impermeable to most hydrophilic molecules and ions, and enable cells to regulate their salt concentrations and pH by pumping ions across the lipid bilayer using transmembrane proteins known as ion pumps. Lipid bilayers, or more generally bilayers of amphipathic molecules, also serve as excellent platforms for a range of experimental studies. Holden et al, J. Am. Chem. Soc. 2007, 129, 8650-8655 disclose the formation of functional bionetworks of aqueous droplets comprising lipid bilayers provided between droplets. Such networks can act as light sensors, batteries and electrical components by incorporating pumps, channels and pores into the bilayers. Sackmann, Science, New Series, Vol 271, No. 5245 (Jan. 5, 1996), pp. 43-48 provides a review of the scientific and practical applications of supported lipid-protein bilayers including their use in electrooptical biosensors. Jung et al, J. Am. Chem. Soc., 2009, 131 (3), 1006-1014 have developed optical assays for the detection of protein ligand binding on supported bilayers.

The ability to form a membrane of amphipathic molecules between two droplets of aqueous solution in a hydrophobic medium such as oil has been demonstrated in WO-2008/012552. Each droplet comprises a layer of amphipathic molecules encapsulating a hydrophilic medium, the droplet being provided in a hydrophobic medium. The droplets are brought into contact to form the membrane of amphipathic molecules therebetween. Electrodes may be provided within the hydrophilic interior of each droplet in order to measure ion flow across the bilayer. A droplet array may be provided in a container having an array of micromachined dimples in which individual droplets may rest.

Another application disclosed in WO-2009/024775 is to form membranes of amphipathic molecules between the volumes of hydrophilic medium in an array and a layer of hydrophilic medium formed by a hydrated support in contact with the volumes of hydrophilic medium. This document discloses a method for producing a droplet interface bilayer, wherein droplets are prepared by contacting an oil/lipid solution with an aqueous solution and the resulting droplets of aqueous solution are brought into contact with an aqueous agarose gel support layer.

It is desirable to use membranes of amphipathic molecules to hold membrane proteins. The provision of ion channel nanopores in highly resistive amphipathic bilayers for the detection of DNA has been previously well documented. Aqueous solutions are provided on either side of the amphipathic bilayer and ion flow through the nanopore takes place under a potential gradient. DNA may be caused to translocate the pore and the change in ion flow during translocation of DNA through the pore may be measured in order to determine its nucleotide sequence. The lipid bilayer may be suspended across an aperture by methods well known in the art such as patch clamping or painting. As an alternative, WO-2009/077734 discloses a plurality of individually addressable lipid bilayers formed across an array of microwell apertures, each microwell containing an electrode and an aqueous medium in contact with the lipid bilayer.

A first aspect of the present invention is concerned with convenient and effective formation of an array of membranes comprising amphipathic molecules.

According to the first aspect of the present invention, there is provided a method of forming an array of membranes comprising amphipathic molecules, the method comprising:

providing an apparatus comprising a support defining an array of compartments having openings through which polar medium may be introduced;

disposing polar medium and apolar medium onto the support to provide volumes comprising polar medium within respective compartments so that the volumes polar medium are constrained from contacting volumes comprising polar medium in neighbouring compartments, and a layer comprising apolar medium extending across the openings in the support in contact with the volumes comprising polar medium; and flowing polar medium across the openings in the support to displace apolar medium and form a layer comprising polar medium extending across the openings in the support in contact with the volumes comprising polar medium and membranes comprising amphipathic molecules at the interfaces between the layer comprising polar medium and the volumes comprising polar medium.

Such a method provides a convenient and effective way to form an array of membranes comprising amphipathic molecules. Use of an apparatus that comprises a support defining an array of compartments having openings, allows an array of volumes comprising polar medium to be disposed within the respective compartments through the openings. As a result, the volumes comprising polar medium are constrained from contacting volumes comprising polar medium in neighbouring compartments, thereby allowing the volumes of polar medium to be used independently, facilitating a range of array-based applications. Such an apparatus may be made to accommodate volumes of any selected size. Typically, the volumes comprising polar medium may have an average volume in the range from 0.4 pL to 400 nL.

To form membranes comprising amphipathic molecules, there is provided a layer comprising apolar medium extending across the openings in the support in contact with the volumes comprising polar medium. Polar medium is flowed across the openings in the support to displace apolar medium and form a layer comprising polar medium extending across the openings in the support in contact with the volumes comprising polar medium. The membranes comprising amphipathic molecules are formed at the interfaces between the layer comprising polar medium and the volumes comprising polar medium. In general, and as described further below, the amphipathic molecules may be provided in the layer comprising apolar medium and/or the polar medium flowed across the openings in the support.

This provides a convenient and effective way to form the membranes. By displacing the apolar medium apolar medium by the polar medium, the membranes are reliably formed.

There are now described various methods of forming an array of membranes.

Several different methods may be applied for disposing the volumes comprising polar medium within respective compartments. The particular method used depends in part on the structure of the support and whether the individual volumes of polar medium are preformed prior to addition to the support or formed subsequently following addition of polar medium to the support. The support may comprise gaps between the compartments or alternatively the support may be provided without gaps between compartments. A first and second types of possible method will now be described.

In the first type of possible method for disposing the volumes comprising polar medium within respective compartments, the volumes are pre-formed before disposition in the compartments. Some possible techniques for this are as follows.

In one possible technique, the polar medium and apolar medium may be disposed onto the support by forming an emulsion of the volumes comprising polar medium in an apolar medium and flowing the emulsion over the support. In this case, volumes comprising polar medium within the apolar medium are introduced into the compartments through the openings. This allows the compartments to be filled in a straightforward manner. The dimensions of the individual volumes of polar medium as well as that of the compartment may be selected such that a single volume of polar medium is provided per compartment.

The partitions of the support may comprises gaps that allow flow of apolar medium between the compartments, as described in more detail below. The gaps are chosen to be of a size that constrains the volumes of polar medium within the compartments whereas the apolar medium is able to flow between the gaps.

The emulsion may further comprise the amphipathic molecules. This facilitates the formation of the membranes when polar medium is flowed across the openings in the support to form the layer comprising polar medium. The presence of the amphipathic molecules also stabilises the emulsion.

Typically, the emulsion contains more volumes comprising polar medium than the number of compartments. The excess of volumes comprising polar medium assists in filling a reasonably large proportion of the compartments. Accordingly, to remove the excess volumes comprising polar medium, the support may be washed with the apolar medium. This washing may be performed leaving volumes comprising polar medium inside compartments, and leaving a layer of the apolar medium used for washing as the layer of apolar medium extending across the openings in the support in contact with the volumes comprising polar medium.

In another possible technique, volumes comprising polar medium may be dispensed directly into individual compartments, for example by acoustic droplet injection. With this technique, the dispensing may be controlled such that the correct number of volumes comprising the polar medium are dispensed without the need to remove excess volumes.

Where the volumes comprising polar medium are pre-formed, they may be droplets of an aqueous buffer solution. Such droplets are easy to form and manipulate.

Where the volumes comprising polar medium are pre-formed, they may be beads of an aqueous gel. Such beads are again easy to form and manipulate and may be shaped as desired Advantageously, the aqueous gel may be a bead, which being relatively hard, provides advantages in manipulating the volumes comprising polar medium. Advantages in filling the compartments may be obtained by flowing an emulsion or suspension of the beads over the support under positive pressure. The use of a bead which resists the pressure permits relatively high positive pressures to be used.

In the second type of possible method, the respective volumes comprising polar medium may be provided in respective compartments by disposing polar medium onto the support, so that the polar medium enters into the compartments through the openings and the layer comprising apolar medium is provided subsequently, for example by flowing the apolar medium across the support, or by another technique such as spraying.

The polar medium may be disposed onto the support by flowing polar medium across the support. Excess polar medium may thereafter be displaced, leaving discrete volumes comprising polar medium in the compartments. In one example, a gas is flowed across the substrate to displace the excess polar medium between the step of flowing polar medium and the step of flowing apolar medium. In another example, the apolar medium is flowed across the substrate layer comprising apolar medium, this flow itself displacing the excess polar medium.

Alternatively, the polar medium may be disposed onto the support by injecting discrete volumes comprising polar medium into the compartments.

An advantage of providing the individual volumes of polar medium in this way is that the polar medium may be added to the support in the absence of amphiphilic molecules.

The support may be pre-treated with a pre-treatment apolar medium prior to disposing the respective volumes comprising polar medium in the respective compartments. In the case where the polar medium is disposed onto the support by flowing polar medium across the support, advantageously, the partitions of the support may comprises gaps that allow flow of apolar medium between the compartments, as described in more detail below. In this case, a pretreatment may provide some degree of sealing of the gaps connecting the respective compartments, thereby constraining the flow of polar medium between the gaps so that the polar medium enters into the compartments through the openings. This assists in the eventual formation of discrete volumes of polar medium by reducing the tendency of the volumes in neighbouring compartments to contact each other. This is particularly beneficial where no amphiphilic molecules are initially present in the volumes of polar media provided within the array of compartments as they may easily converge if they contact one another.

The addition of pretreatment may also be used change the contact angle between the pretreated material of the support and a volume of polar medium disposed within a compartment. The pretreatment may be used for example to increase the phobicity of the support to the polar medium and provide a volume having a more convex shape in order to optimise formation of the membrane at the interface between the volume of polar medium and the layer of polar medium. The use of a pretreatment to alter the phobicity of the support to a desired level permits the use of a wider number of materials to be considered in making the support. This can be useful for example in the case where a particular material is desirable from a manufacturing point of view but does not have the correct properties with regards to the polar and apolar media. The layer comprising apolar medium may further comprise the amphipathic molecules. This facilitates the formation of the membranes when polar medium is flowed across the openings in the support to form the layer comprising polar medium.

In one example, the apolar medium may comprise the amphipathic molecules prior to the addition of the layer of apolar medium to the support. Alternatively, the amphipathic molecules may be added to the layer of apolar medium following addition of the layer to the support.

Where the layer comprising apolar medium further comprises the amphipathic molecules, between the steps of providing a layer comprising apolar medium extending across the openings in the support in contact with the volumes comprising polar medium and flowed across the openings in the support, the apparatus may be left for a period of time in order to allow the amphipathic molecules to migrate to the interface between the layer comprising apolar medium and the volumes comprising polar medium.

In another example, the polar medium that is flowed across the openings in the support may further comprise the amphipathic molecules. This similarly facilitates the formation of the membranes when polar medium is flowed across the openings in the support to form the layer comprising polar medium.

In yet another example, the pre-treatment of apolar medium may further comprise amphipathic molecules, so that the membranes comprising amphipathic molecules are formed after the step of flowing polar medium across the openings in the support to form a layer comprising polar medium.

The membranes comprising amphipathic molecules may be used for a range of applications such as detection of an analyte at the membrane interface, determination of a property of the membrane interface, or passage of an analyte across one or more membrane interfaces. In some applications, the membranes may be used to analyse a sample comprising an analyte, for example a biological sample.

In one type of application, there may be used membrane proteins, such as ion channels or pores that are inserted into the membranes comprising amphipathic molecules. The membrane proteins may initially be contained in the volumes comprising polar medium or in the layer comprising polar medium. Alternatively the membrane proteins may be provided in the apolar medium. The membrane proteins typically spontaneously insert in the membranes comprising amphipathic molecules. Insertion of the membrane proteins into the membrane can be assisted where necessary for example by means such as the application of a potential difference across the membrane.

Some applications may use measurement of electrical properties across the membranes, for example ion current flow. To provide for such measurements, the support may further comprise respective electrodes in each compartment making electrical contact with the volumes comprising polar medium. Other types of measurements may be carried out for example optical measurements such as fluorescence measurements and FET measurements. Optical measurements and electrical measurements may be carried out simultaneously (Heron A J et al., J Am Chem Soc. 2009; 131(5):1652-3).

In the case that the apparatus comprises respective electrodes in each compartment, the pretreatment, where used, preferably does not cover the electrode surface and is localised elsewhere on the support.

The apparatus may further comprise a common electrode arranged so that the common electrode makes electrical contact with the layer comprising polar medium, when disposed extending across the support over the openings.

The apparatus may further comprise an electrical circuit connected between the common electrode and the respective electrodes in each compartment, the electrical circuit being arranged to take electrical measurements. Such electrical measurements may be dependent on a process occurring at or through the membranes comprising amphipathic molecules.

In the embodiment of forming an array of membranes whereby an emulsion of volumes comprising polar medium in an apolar medium is formed and flowed over the support, a stable emulsion is required in order to prevent the volumes of polar medium from merging with each other. Merging of volumes gives rise to larger volumes which may be unable to be accommodated in a compartment and which also gives rise to an increased range of sizes of volumes. Droplet merging may be prevented or minimised by adding amphiphilic molecules to the apolar medium or polar medium prior to forming the emulsion such that a volume of polar medium is effectively coated with a layer of amphiphilic molecules. However this can in some circumstances give rise to an increased electrical resistance between the electrode and the volume of polar medium due to the electrode being coated with amphiphilic molecules. In an alternative embodiment of forming an array of membranes whereby the individual volumes of polar medium are provided in the respective compartments prior to the addition of amphiphilic molecules, the volumes of polar medium are able to directly contact the electrode surfaces.

The support may have a variety of advantageous constructions.

The support may comprise a base and partitions extending from the base that define the compartments and constrain the volumes comprising polar medium from contacting volumes comprising polar medium in neighbouring compartments.

In a first possible type of construction of the support, the partitions comprise inner portions and outer portions, the inner portions defining inner recesses of the compartments without gaps therebetween, the volumes comprising polar medium being disposed within the inner recesses of the respective compartments, and the outer portions extending outwardly from the inner portions defining outer portions of the compartments and in which gaps allowing the flow of apolar medium between the compartments are formed. Effectively, the gaps in the partitions extend partway to the base. This construction has advantages of providing reliable and controlled formation of the membranes.

Where the apparatus comprises respective electrodes provided in each compartment, the electrodes may be provided at the base.

The volumes comprising polar medium may fill the inner recesses. The gaps between the outer portions assist in filling of the inner recesses. A meniscus may therefore form across the inner recess. Particular advantage is achieved in the case that polar medium is disposed in respective compartments by flowing polar medium across the support, and excess polar medium is displaced by a displacing fluid, which may be a gas or may be the apolar medium flowed across the substrate to form the layer. In this case, the gaps between the outer portions assist in permitting flow of the displacing fluid across the substrate, so that the apolar medium fills the inner recesses.

The gaps between the outer portions assist the formation of membranes by allowing the displacement of apolar medium between the compartments when the polar medium is brought into contact with the polar medium in the recesses.

The inner recesses and the outer portions of the partitions may have dimensions selected for the volumes comprising polar medium to form a meniscus across the inner recess and the layer comprising polar medium may form meniscuses across the outer portions. Those meniscuses extend towards each other to an extent that brings the layer comprising polar medium in contact with the volumes comprising polar medium. Thus the geometry controls the formation of the membranes providing reliability in the formation. This also allows control of the size and stability of the membranes comprising amphipathic molecules.

The outer portions are set back from the edges of the inner recesses as viewed from the openings. Although not essential, this assists the functions described above of assisting in the filling of the inner recesses by polar medium and in the layer comprising polar medium forming meniscuses across the outer portions.

The outer portions may be pillars extending from the inner portion.

The support may be designed as follows to facilitate formation of the membranes comprising amphipathic molecules.

Advantageously, the outer ends of the partitions may extend in a common plane. This improves the adhesion of the layer comprising polar medium to the support and therefore improves the stability of formation of the membranes comprising amphipathic molecules.

The edges of the outer ends of the partitions provide pinning of the layer comprising polar medium to the support. Advantageously, to assist such pinning, the partitions may be designed so that the total length per compartment of the edges of the outer ends of the partitions in the common plane is greater than the largest circumference of the largest notional sphere that can be accommodated within the compartments.

The inner recesses and/or outer portions may have surfaces having a patterning that is arranged to retain apolar medium, for example a plurality of indentations that extend outwardly of the compartments, or in general any microfabricated surface features. The retention of apolar medium may advantageously be used to change the surface properties of the substrate, for example to control the formation of membranes in an application where they are formed.

Apolar medium provided retained by the patterning may serve to change the contact angle between the volumes of polar medium and the support. This can in some embodiments increase the phobicity of the support to the polar medium and provide volumes of polar medium having a more convex outer surface. This may subsequently result in a smaller membrane formed at the interface between the volume of polar medium and the layer of polar medium. The base of the compartments typically do not have microfabricated surface features, such that any pretreatment of apolar medium added to the apparatus is localised and retained at the partitions. As such contact between the respective electrodes in the base of each compartment, if present, and the pretreatment, if present, is minimised.

According to a second aspect of the present invention, there is provided an apparatus for forming an array of volumes comprising polar medium, the apparatus comprising a support that comprises partitions which comprise inner portions and outer portions, the inner portions defining inner recesses without gaps therebetween that are capable of constraining volumes comprising polar medium that may be contained in neighbouring inner recesses from contacting each other, and the outer portions extending outwardly from the inner portions and having gaps allowing the flow of an apolar medium across the substrate.

An apparatus in accordance with the second aspect of the present invention may be used as the apparatus in the first aspect of the present invention.

In a second possible type of construction of the support, the partitions may have gaps extending to the base allowing the flow of apolar medium between the compartments. This facilitates filling of the compartments with the volumes comprising polar medium because the gaps allow for displacement of the apolar medium that may enter the compartments beforehand.

In a third possible type of construction of the support, the partitions may have no gaps allowing the flow of apolar medium between the compartments. This type of construction has the advantage of maximising the electrical isolation of the compartments.

According to a third aspect of the present invention, there is provided an apparatus for holding volumes comprising polar medium comprising:

a support comprising a base and partitions that extend from the base and define an array of compartments containing an apolar medium; and at least some of the compartments also containing volumes comprising polar medium within the apolar medium that are constrained by the partitions from contacting volumes comprising polar medium in neighbouring compartments.

The apparatus according to the second and third aspects of the invention may be used as a droplet array in a wide range of biological, pharmaceutical or industrial applications, as discussed above.

An apparatus in accordance with the third aspect of the present invention may be used as the apparatus in the first aspect of the present invention, or in a fourth aspect of the invention, according to which, there is provided a method of forming an array of volumes comprising polar medium, the method comprising:

providing a support comprising a base and partitions extending from the base and defining an array of compartments; and disposing an apolar medium in the compartments and volumes comprising polar medium within the apolar medium in at least some of the compartments so that the volumes comprising polar medium in respective compartments are constrained by the partitions from contacting volumes comprising polar medium in neighbouring compartments.

Such a support provides a convenient and effective way to hold an array of volumes comprising polar medium within the apolar medium. The partitions constrain the volumes comprising polar medium in respective compartments from contacting volumes comprising polar medium in neighbouring compartments, thereby allowing volumes, which may be individual volumes, of polar medium to be used independently, facilitating a range of array-based applications. Such an apparatus may be made to accommodate volumes of any selected size. Typically, the volumes comprising polar medium might have an average diameter in the range from 5 µm to 500 µm, or an average volume in the range from 0.4 pL to 400 nL.

The support is easy to fill with the volumes comprising the polar medium. In one possible technique, the volumes comprising polar medium may be disposed within the compartments by forming an emulsion of the volumes comprising polar medium in an apolar medium and flowing the emulsion over the support. This allows the compartments to be filled in a straightforward manner Typically, the emulsion contains more volumes comprising polar medium than the number of compartments. The excess of volumes comprising polar medium assists in filling a reasonably large proportion of the compartments. Accordingly, to remove the excess volumes comprising polar medium, the support may be washed with the apolar medium. This washing may be performed leaving volumes comprising polar medium inside compartments.

In another technique, volumes comprising polar medium may be dispensed directly into individual compartments, for example by acoustic droplet injection. With this technique, the dispensing may be controlled such that the correct number of volumes comprising the polar medium are dispensed without the need to remove excess volumes.

The support may be used to form membranes comprising amphipathic molecules between the volumes comprising polar medium and a layer comprising polar medium. That is, a layer comprising polar medium may be disposed extending across the support over the openings of the compartments and in contact via the amphipathic membrane with at least some of the volumes comprising polar medium. The membranes comprising amphipathic molecules are formed at the interfaces between the layer comprising polar medium and the volumes comprising polar medium.

In an embodiment, the amphipathic molecules may be provided in the volumes comprising polar medium and/or the apolar medium in order to provide a layer comprising amphipathic molecules around the volumes comprising polar medium disposed within the compartments prior to provision of the layer comprising polar medium.

If for example the volumes comprising the polar medium are provided in the form of liquid droplets in the apolar medium, the presence of a layer of amphipathic molecules around the volumes reduces the tendency of the volumes to merge with each other. Thus it is preferable that the amphipathic molecules are added to either the apolar medium or the volumes comprising the polar medium before formation of the droplets in the apolar medium. If the individual droplets do not contact each other prior to being introduced into the compartments, the droplets of polar medium may be provided in the apolar medium in the absence of amphipathic molecules. In this latter case, the amphipathic molecules may be subsequently added, for example in the layer comprising polar medium, in order to provide a layer of amphipathic molecules around the volumes comprising the polar medium provided within the apolar medium.

The membranes comprising amphipathic molecules may be used for a range of applications such as detection of an analyte at the membrane interface, determination of a property of the membrane interface, or passage of an analyte across one or more membrane interfaces In some applications, the membranes may be used to analyse a sample comprising an analyte, for example a biological sample.

In one type of application, there may be used membrane proteins, such as ion channels or pores that are inserted into the membranes comprising amphipathic molecules. The membrane proteins may initially be contained in the volumes comprising polar medium or in the layer comprising polar medium. Alternatively the membrane proteins may be provided in the apolar medium. This causes the membrane proteins to spontaneously insert, after formation of membranes comprising amphipathic molecules.

Some applications may use measurement of electrical properties across the membranes, for example ion current flow. To provide for such measurements, the support may further comprise respective electrodes in each compartment making electrical contact with the volumes comprising polar medium. Other types of measurements may be carried out for example optical measurements such as fluorescence measurements and FET measurements. Optical measurements and electrical measurements may be carried out simultaneously (Heron A J et al., J Am Chem Soc. 2009; 131(5):1652-3).

A compartment may contain a single volume of polar medium. Alternatively, a compartment may comprise more than one volume of polar medium, for example two volumes. The volumes comprising polar medium may be provided one on top of the other. The membranes comprising amphipathic molecules may be formed at the interfaces between a layer comprising polar medium and the volumes comprising polar medium. Membranes proteins may be provided at the interface between the volumes comprising polar medium to provide an ion or analyte transport pathway between the electrode and the hydrophilic layer.

The compartments of the array may be arranged in various ways, for example in a square packed, rectangular packed or hexagonal packed arrangement.

The apparatus may further comprise a common electrode arranged so that the common electrode makes electrical contact with the layer comprising polar medium, when disposed extending across the support over the openings.

The apparatus may further comprise an electrical circuit connected between the common electrode and the respective electrodes in each compartment, the electrical circuit being arranged to take electrical measurements. Such electrical measurements may be dependent on a process occurring at or through the membranes comprising amphipathic molecules.

The support may have a variety of advantageous constructions.

In a first possible type of construction, the partitions may have gaps allowing the flow of apolar medium between the compartments. This facilitates filling of the compartments with the volumes comprising polar medium because the gaps allow for displacement of the apolar medium that may enter the compartments beforehand.

In a construction having gaps, a first possibility is for the gaps to extend to the base. This construction has the advantage that the flow of apolar medium may occur between the compartments.

In a construction having gaps, a second possibility is for the gaps to extend partway to the base. For example, the support may have a construction in which the partitions comprise inner portions defining the inner portions of the compartments without gaps therebetween and outer portions that extend outwardly from the inner portion defining the inner portions of the compartments and in which said gaps are formed. This construction has the advantage that the electrical isolation of the compartments is improved whilst still permitting the flow of apolar medium between the compartments.

In a second possible type of construction, the partitions may have no gaps allowing the flow of apolar medium between the compartments. This type of construction has the advantage of maximising the electrical isolation of the compartments.

In this second possible type of construction, the partitions may have a profile as viewed across the support that comprises, around individual compartments, one or more salient portions which serve to reduce the contact between a volume of polar medium and the inner partition surface. This reduction in the contact surface area reduces the surface tension between the volume of polar medium and the inner partition surface and enables the volume to move within a compartment more easily and for example move to the base of the compartment in order to contact the electrode surface. The dimensions and number of salient portions provided around the surface of an inner partition of a compartment may vary. The reduction in contact between the droplet and the inner partitions surface enables a larger droplet to be incorporated than would have otherwise been possible in the absence of such salient portions.

The partitions may comprise one or more re-entrant portions providing channels allowing outflow of apolar medium displaced by entry of a volume of polar medium into the compartment. Such a profile is advantageous in filling of the compartments with the volumes comprising polar medium because the re-entrant portions allow for displacement of the apolar medium that may enter the compartments beforehand. The dimensions of a channel may vary. The apolar medium is more easily displaced through channels having a greater cross-sectional area. The partitions may comprise both one or more salient portions and one or more re-entrant portions. The dimensions of the one or more re-entrant portions may also determine the extent of surface contact between a volume of the polar medium and the inner partition surface.

The support may be designed as follows to facilitate formation of the membranes comprising amphipathic molecules.

Advantageously, the outer ends of the partitions may extend in a common plane. This improves the adhesion of the layer comprising polar medium to the support and therefore improves the stability of formation of the membranes comprising amphipathic molecules.

The edges of the outer ends of the partitions provide pinning of the layer comprising polar medium to the support. Advantageously, to assist such pinning, the partitions may be designed so that the total length per compartment of the edges of the outer ends of the partitions in the common plane is greater than the largest circumference of the largest notional sphere that can be accommodated within the compartments.

The dimensions of the openings of the compartments may be selected so that when the layer comprising polar medium is provided extending across the support over the openings, the layer comprising polar medium forms a meniscus extending into the compartment to an extent that brings the layer comprising polar medium in contact with at least some of the volumes comprising polar medium. This allows control of the size and stability of the membranes comprising amphipathic molecules. In the construction where the gaps extend partway down the base defining inner and outer portions, the arrangement and dimensions of the outer portions will determine whether the meniscus is pinned at the outer portions or the inner portions.

The following comments about the polar and apolar media apply to all the aspects of the present invention.

The polar medium may be a hydrophilic medium. The apolar medium may be a hydrophobic medium. In a particular embodiment, a single volume of polar medium is provided in a compartment.

The volumes comprising polar medium are typically volumes comprising an aqueous medium, for example an aqueous buffer solution.

The polar medium of respective volumes provided in the compartments may be the same or different. The volumes may each comprise different substances or differing concentrations of the same substance. For example, the volumes comprising polar medium may contain varying amounts of a substance A and the polar layer may comprise a substance B wherein a detectable interaction or reaction may occur between A and B. In this way substance B may pass through the ion-channels into the respective volumes comprising the polar medium. By detecting the individual interactions or reactions, for example a fluorescent signal, a multitude of ion channel experiments may be carried our simultaneously for example to determine an optimal reaction or interaction between B and A.

The layer comprising polar medium may typically comprise an aqueous medium, for example an aqueous buffer solution.

The polar medium of the layer may be the same or different polar medium as the respective volumes provided in the compartments. They may comprise different substances or differing concentrations of the same substance.

Embodiments of the present invention will now be described by way of non-limitative example with reference to the accompanying drawings, in which.

Figure 19:
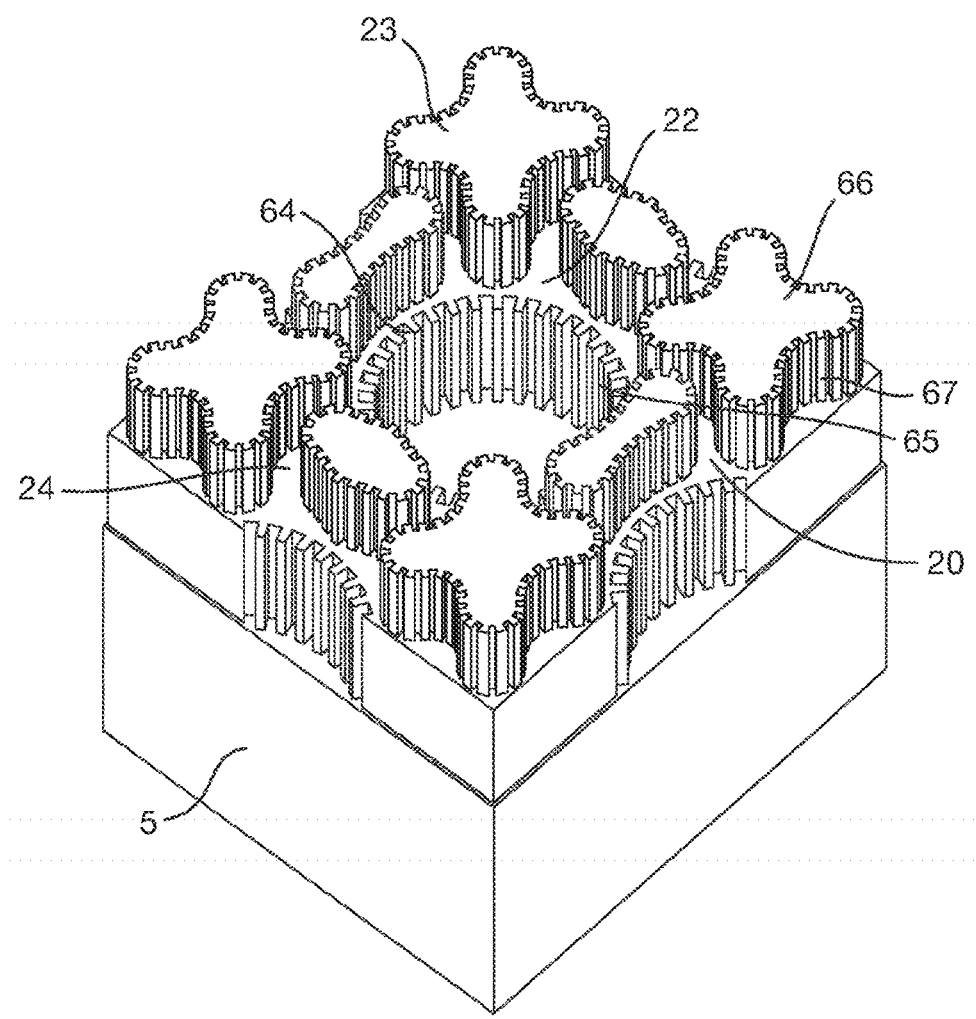
FIG. 19 is an isometric projection of a modified construction for the partitions.
Figure 21:
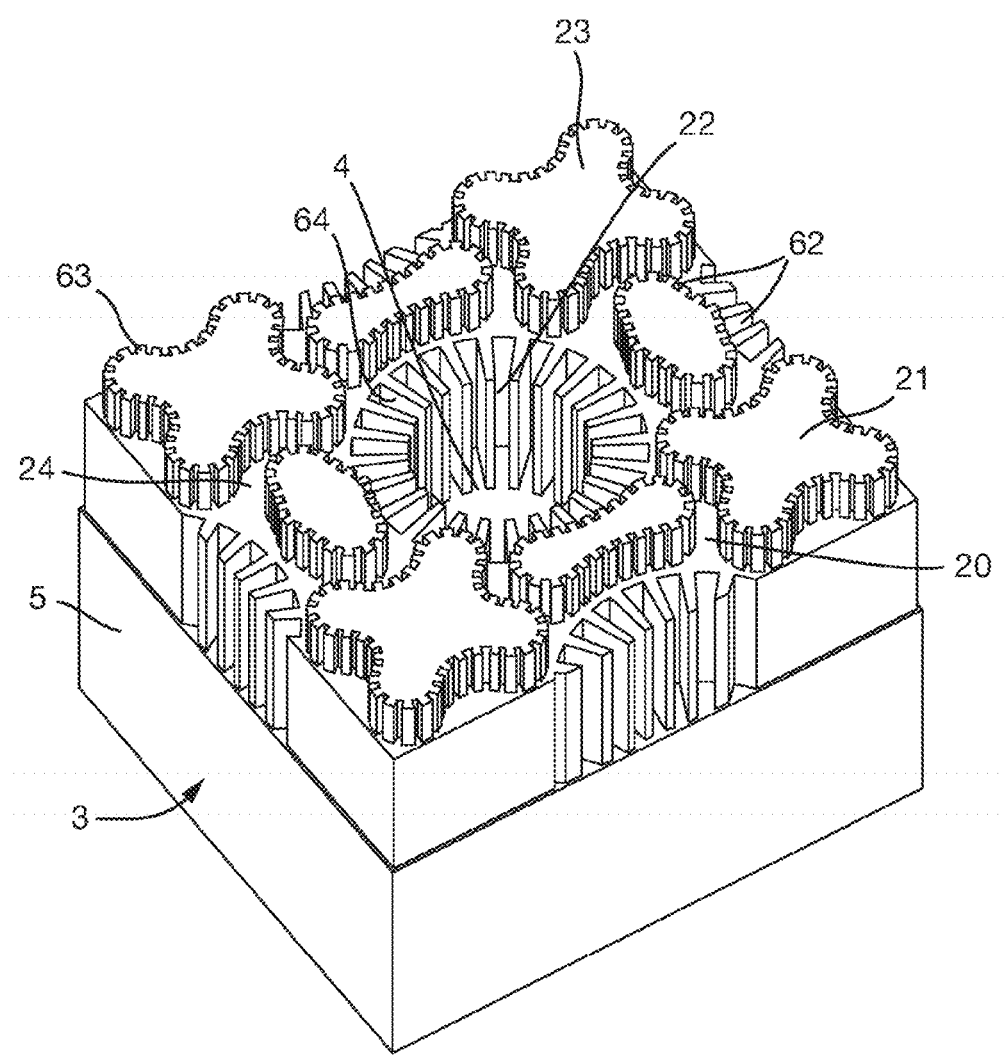
FIG. 21 is an isometric projection of a modified construction for the partitions.
Figure 36B:
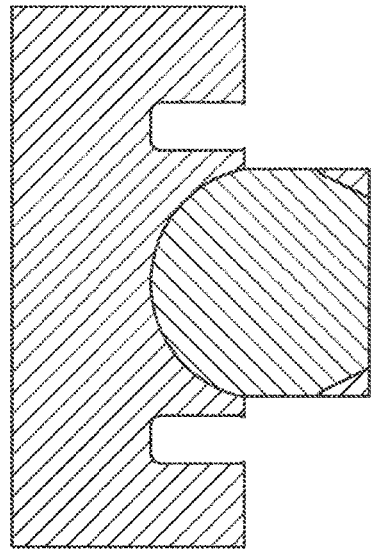
Figure 36A:
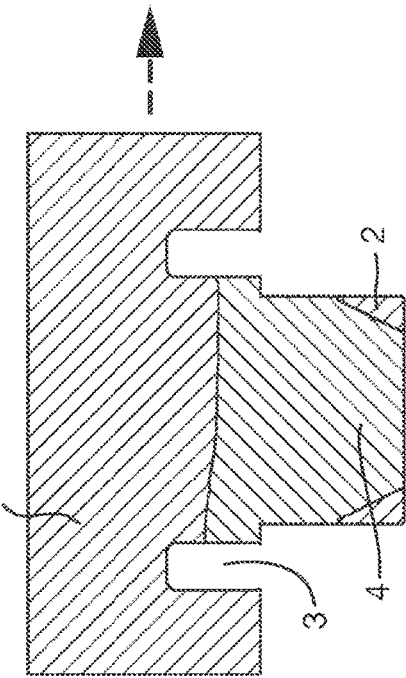
Figure 36C:
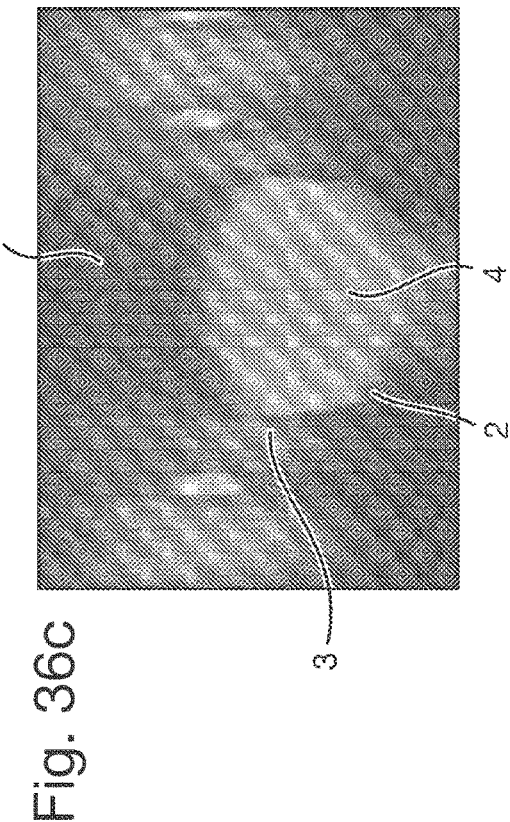
Figure 38A:
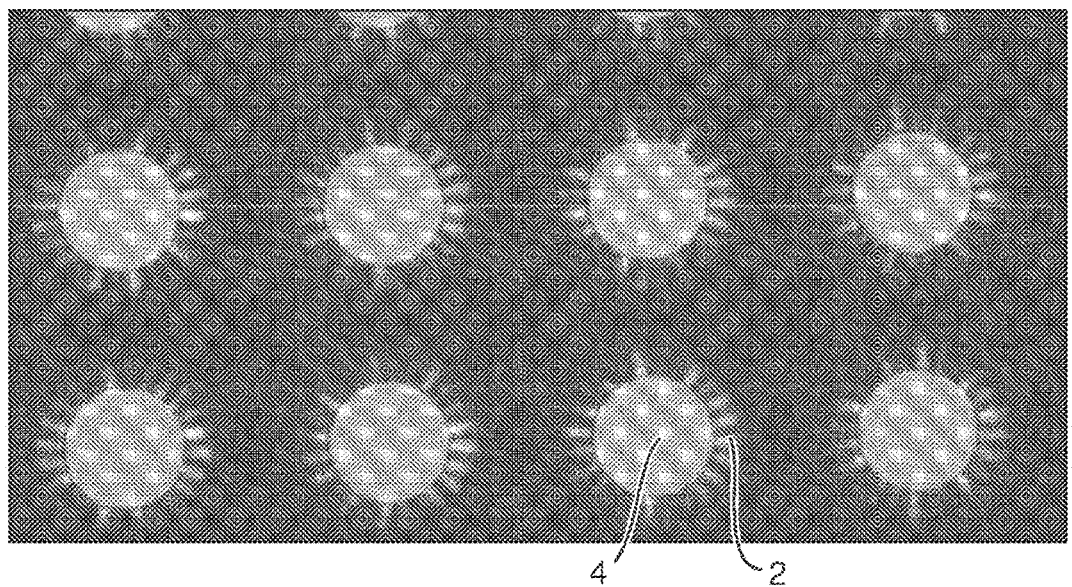
Figure 38B:
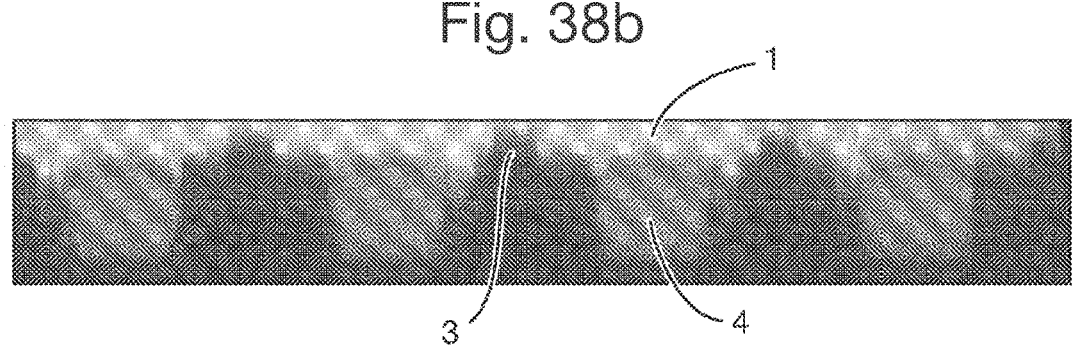
Figure 39A:
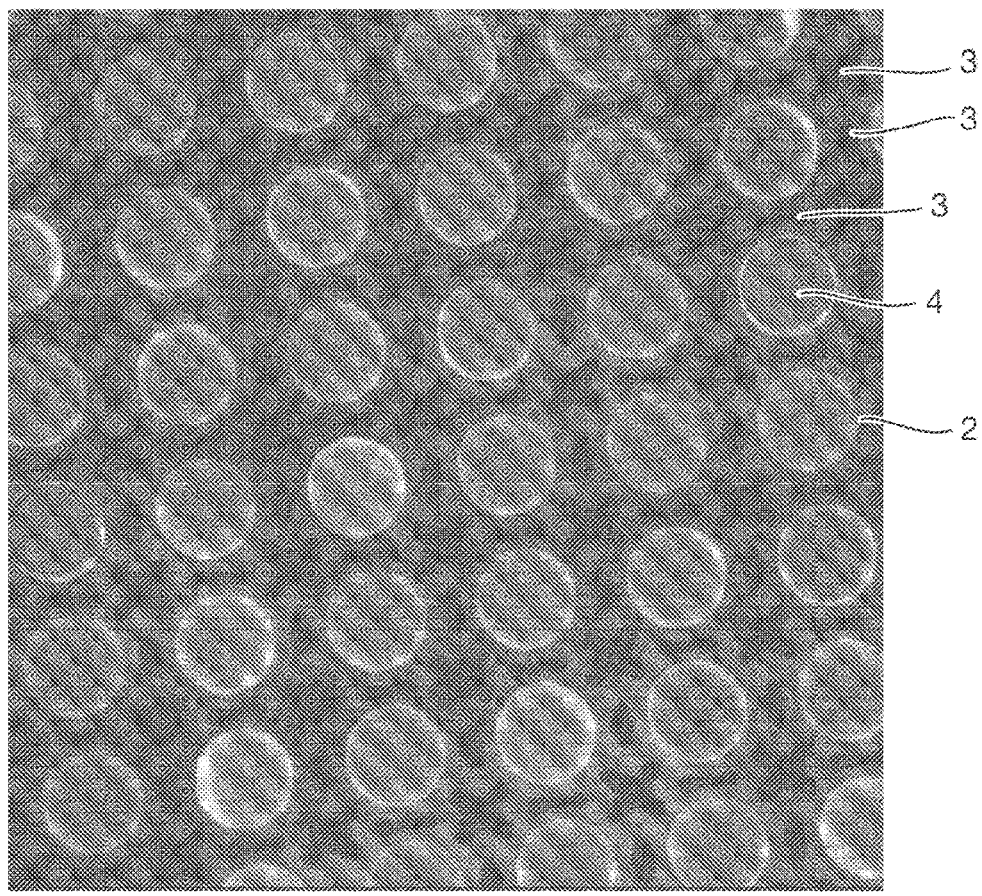
Figure 39B:
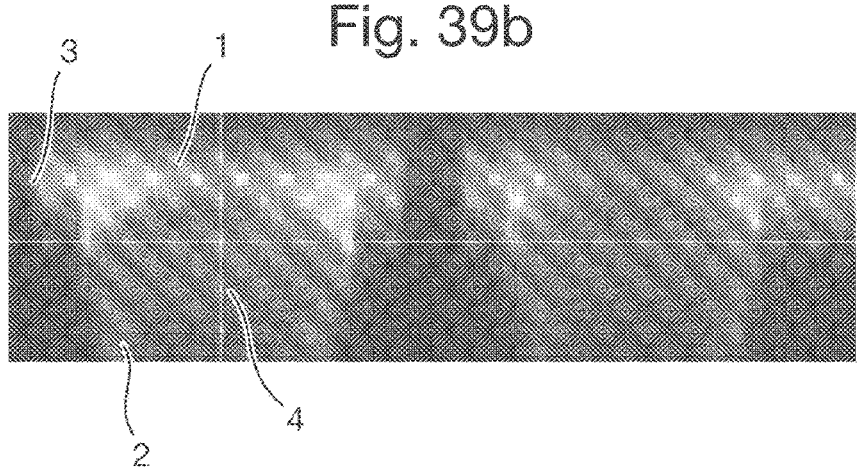

FIGS. 36 (A) and (B) are side views of a compartment during the computer simulation;

FIG. 36C is a confocal image of a compartment in which an inner recess is filled with a volume of polar medium;

FIG. 37 are side views of compartments of different size during a computer simulation;

FIG. 38 is a set of images of a support in the construction of FIG. 21 in which inner recesses are filled with volumes of polar medium;

FIG. 39 are images of a support in the construction of FIG. 19 in which inner recesses are filled with volumes of polar medium;

FIGS. 40 (A) and (B) are images of a support in the construction of FIG. 19 after formation of an array of membranes; and FIG. 40(C) is a schematic side view of a compartment having a formed membrane.

Figure 15:
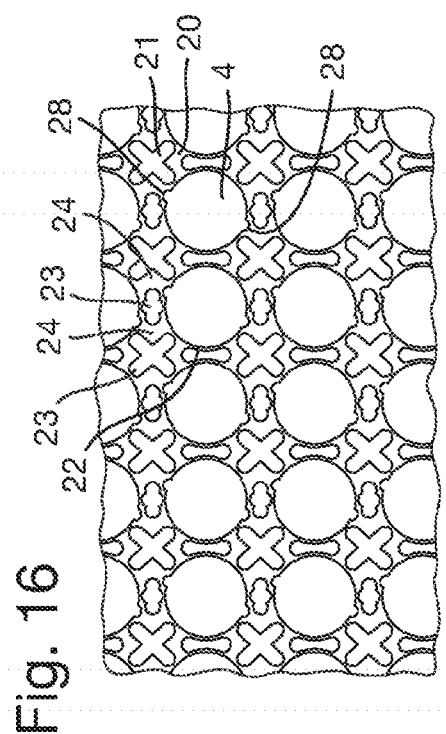
FIG. 15 is an isometric projection of the second alternative construction for the partitions.
Figure 16:
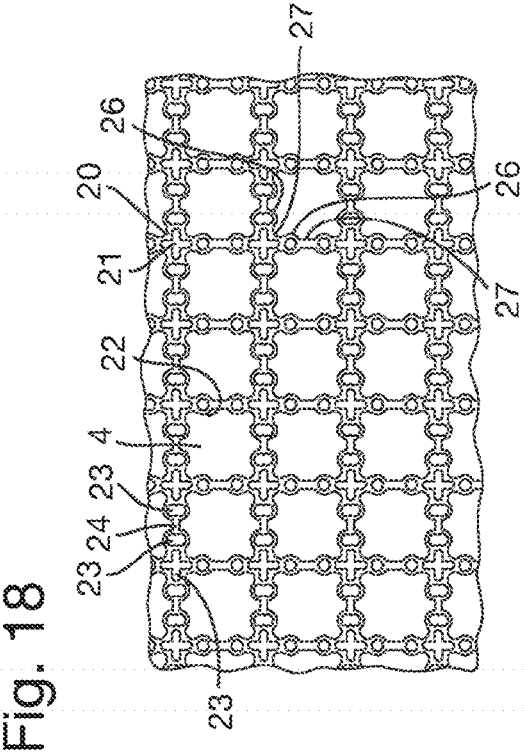
FIG. 16 is a plan view of the partitions of FIG. 15.
Figure 41:
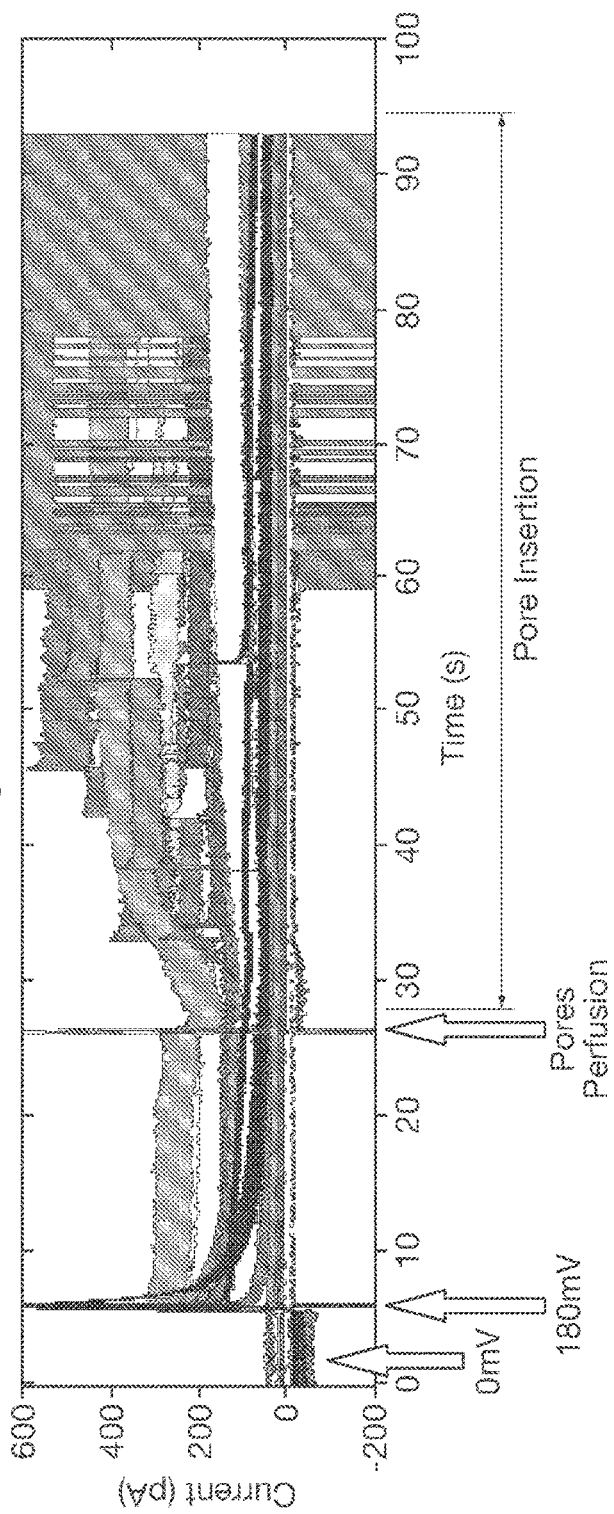
Figure 42:
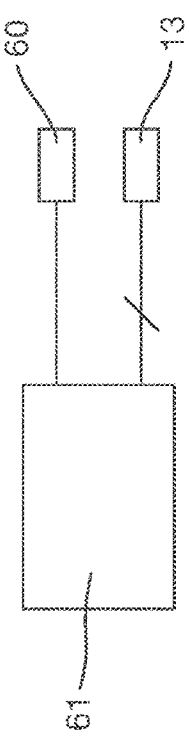
Figure 43:
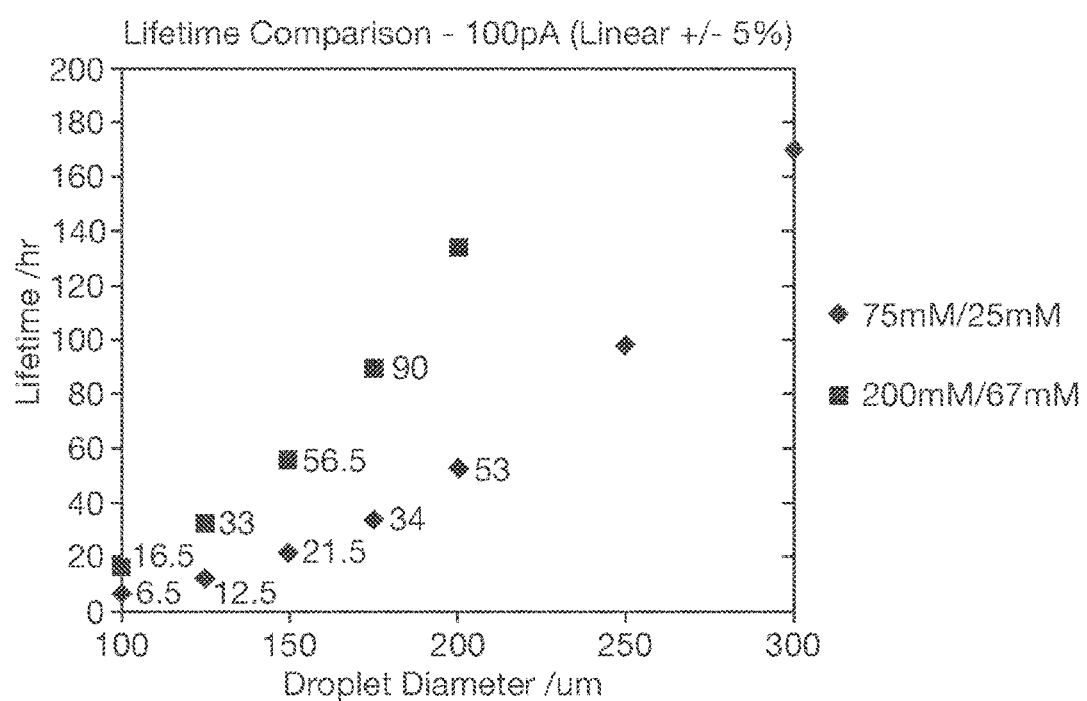
Figure 44A:
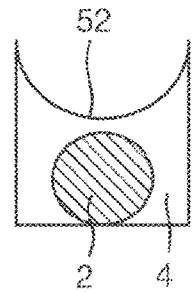
Figure 44B:
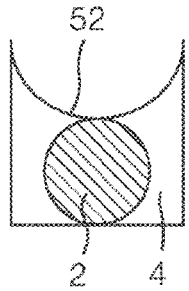
Figure 44C:
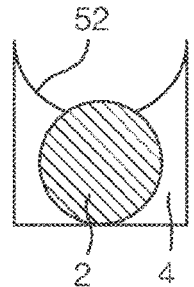
Figure 45:
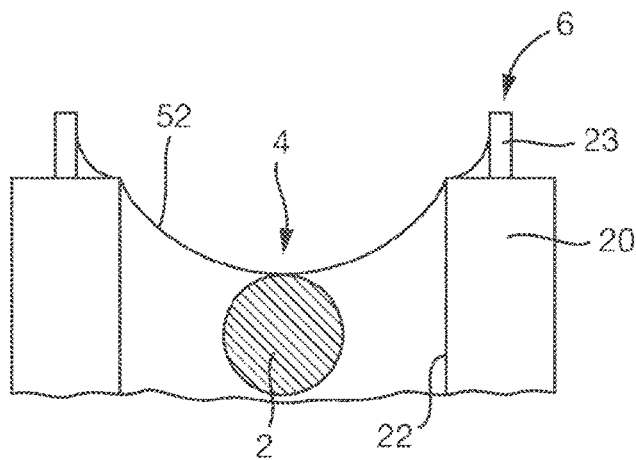
Figure 46:
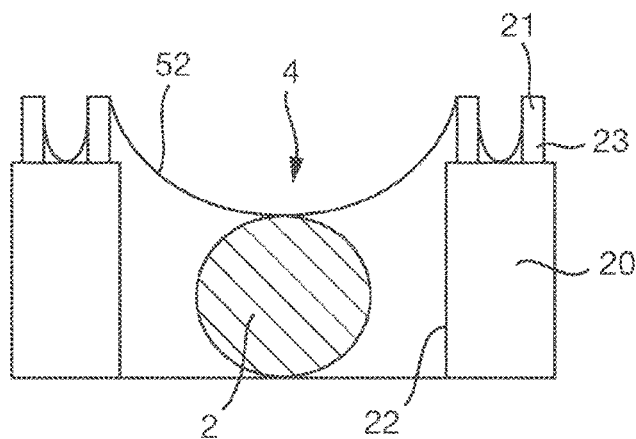
Figure 47:
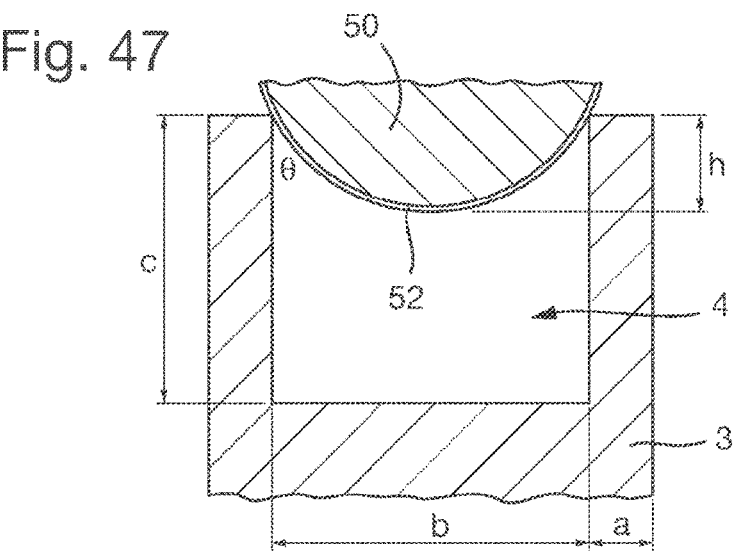
Figure 48A:
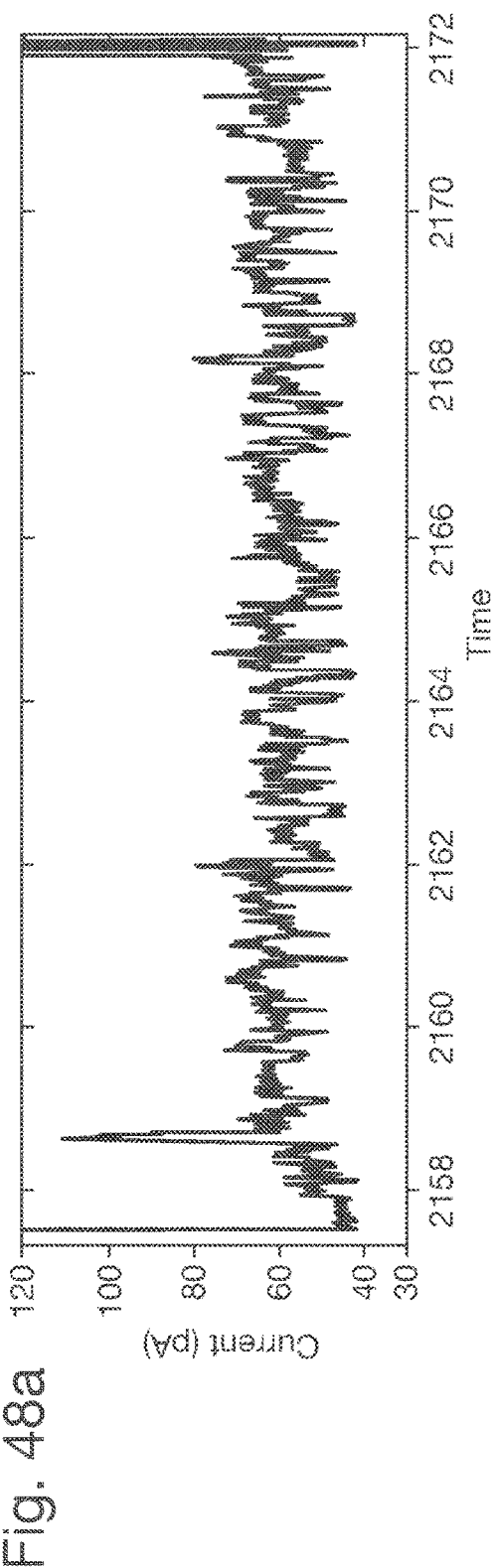
Figure 48B:
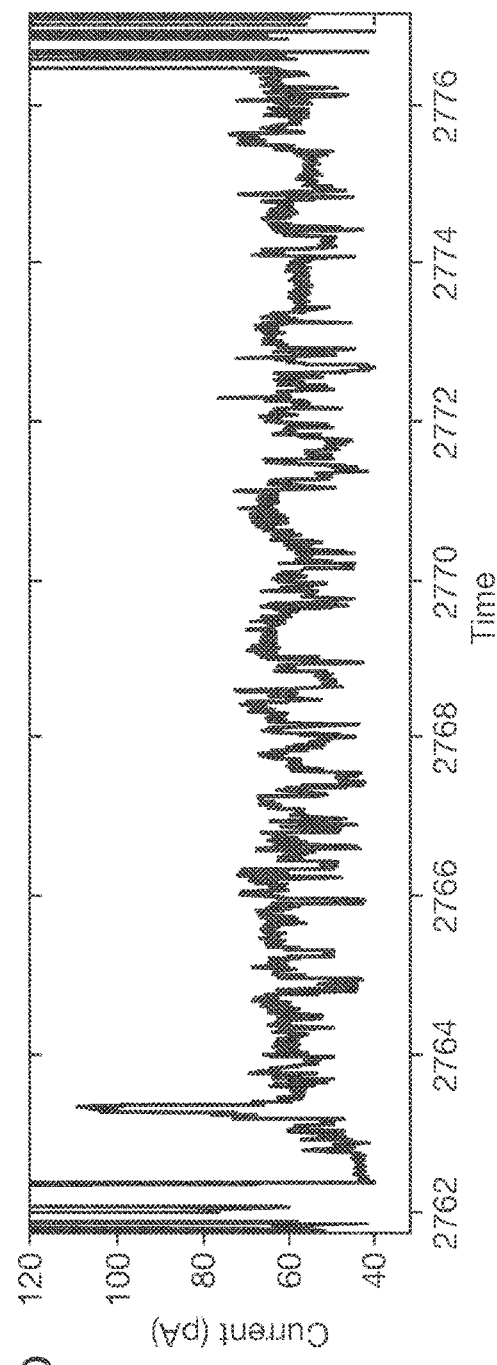

FIG. 41 is a graph of current against time showing electrical data obtained for measurement of ion current flow through an MspA nanopore;

FIG. 42 is a diagram of an electrical circuit of the apparatus;

FIG. 43 is a graph of lifetime against size for various volumes of polar medium;

FIGS. 44(a) to (c) are schematic side views of a droplets of different size in a compartment;

FIGS. 45 and 46 are schematic cross-sectional views of the apparatus of the type shown in FIGS. 15 and 16;

FIG. 47 is a side view of a meniscus formed across the opening of a compartment;

FIG. 48 shows current traces as a function of time in ms showing helicase-controlled DNA movement through an MspA-(B2C) nanopore which is inserted in tri-block co-polymer under an applied potential of 180 mV, wherein A and B show examples of two helicase-controlled DNA translocations through MspA nanopores.

Figure 49:
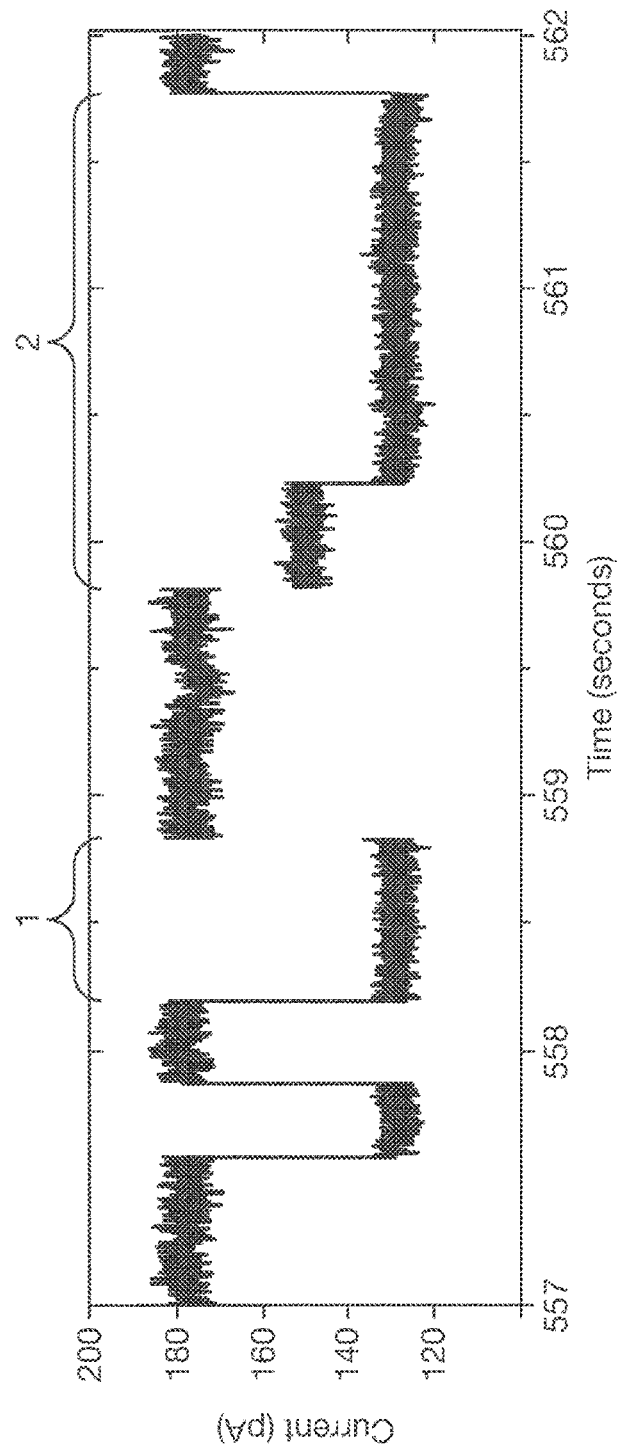
Figure 50:
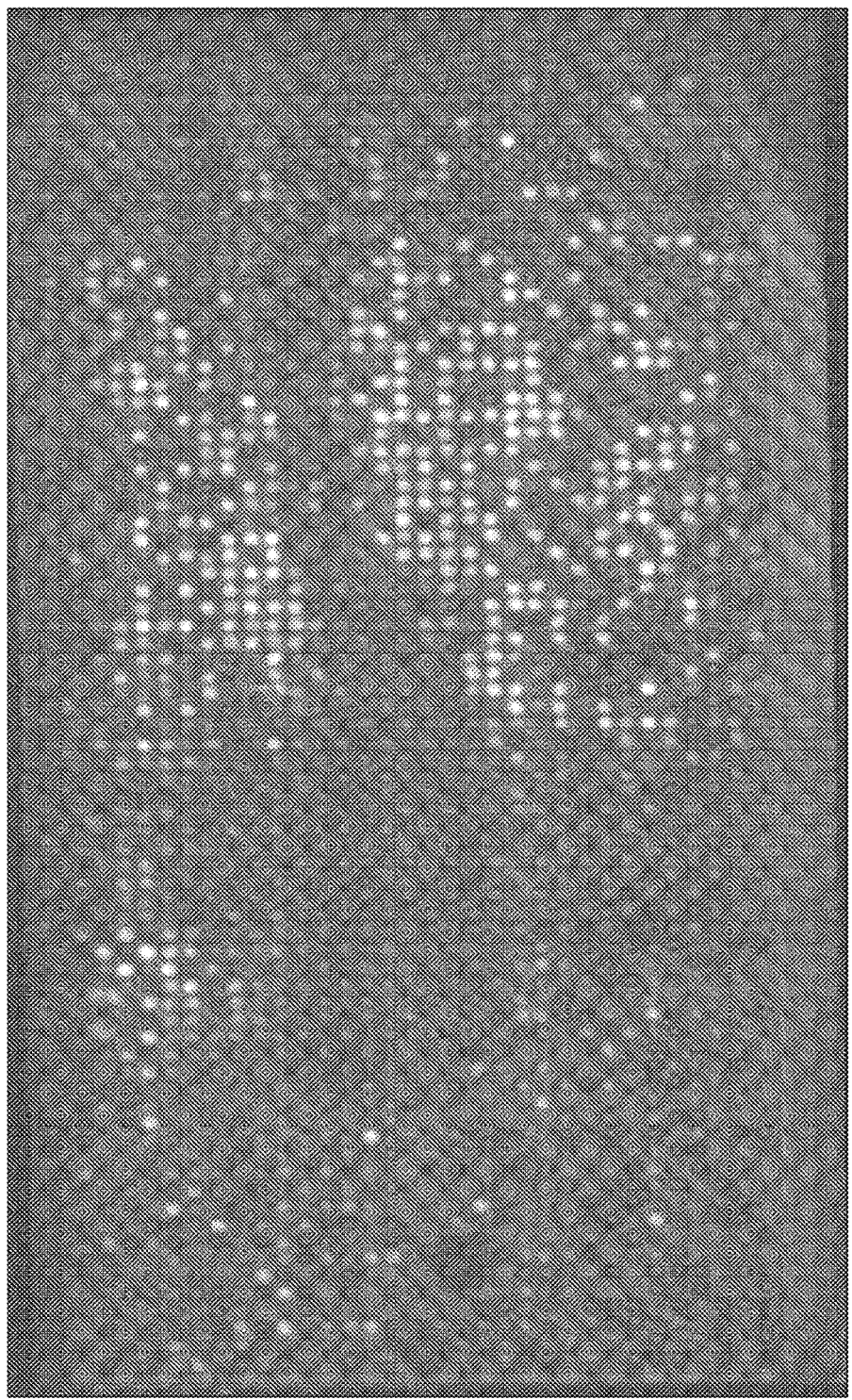
Figure 51:
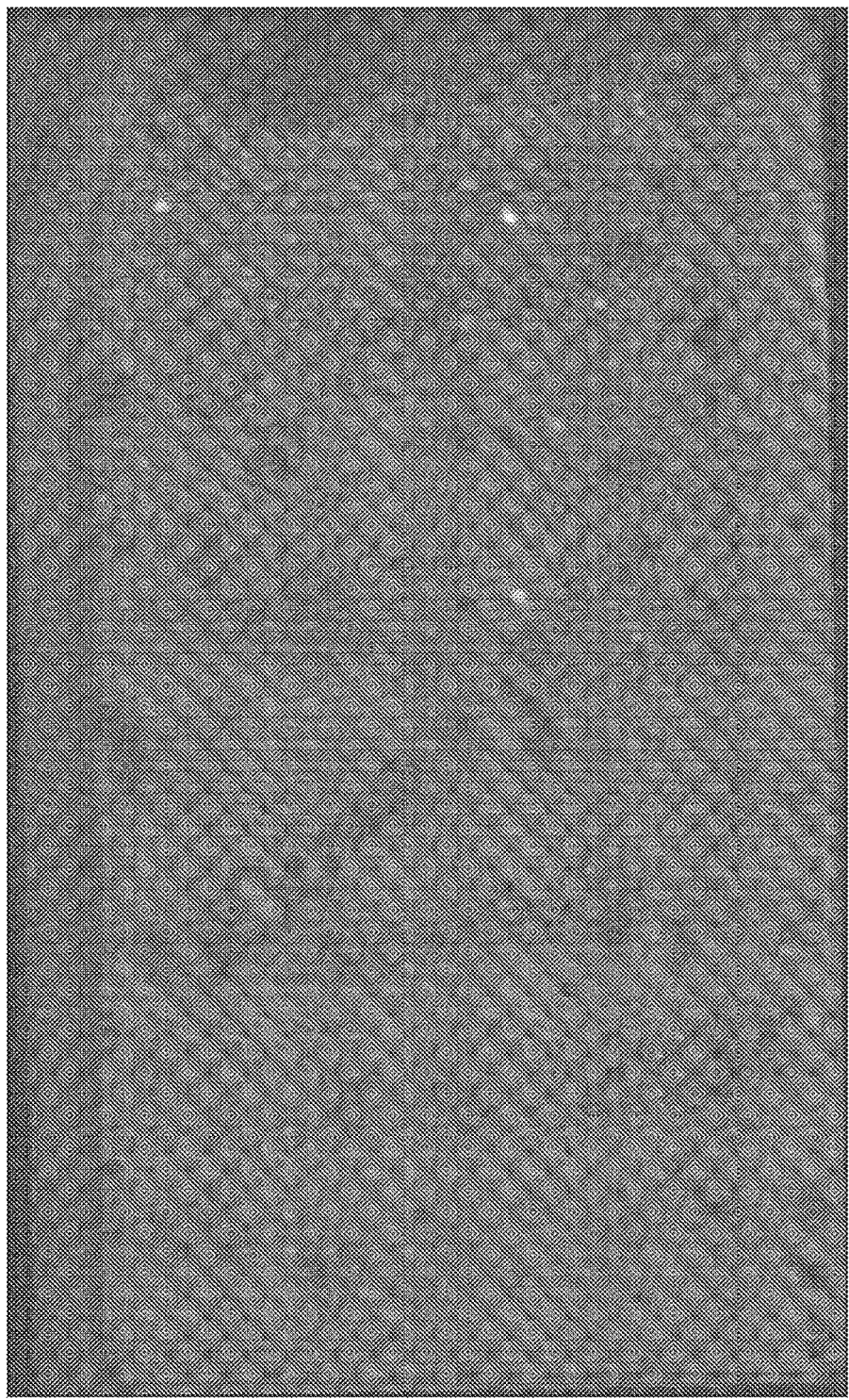

FIG. 49 shows a current trace showing characteristic block levels corresponding to the presence (block labelled 2) and absence (block labelled 1) of thrombin;

FIG. 50 shows a Brightfield image of a chip which has been exposed to MspA-(B2C) (SEQ ID NO: 1) nanopores; and FIG. 51 shows an Brightfield image of chip which has not been exposed to MspA-(B2C) (SEQ ID NO: 1) nanopores.

The specification refers to various sequences as follows.

SEQ ID NO: 1 shows the amino-acid sequence of MspA-(B2C). The amino-acid sequence of MspA-(B2C) is a variant of SEQ ID NO: 2 with the following mutations G75S/G77S/L88N/Q126R.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows one of the polynucleotide sequences used in Example 5. It is connected at its 3' end to the 5' end of SEQ ID NO: 4 via four spacer units.

SEQ ID NO: 4 shows one of the polynucleotide sequences used in Example 5. It is connected at its 5' end to the 3' end of SEQ ID NO: 3 via four spacer units.

SEQ ID NO: 5 shows the polynucleotide sequence encoding one subunit of α-hemolysin-E111N/K147N (α-HL-NN; (Stoddart, D. S., et al., (2009), *Proceedings of the National Academy of Sciences of the United States of America* 106, p 7702-7707).

SEQ ID NO: 6 shows the amino acid sequence of one subunit of α-HL-NN.

SEQ ID NO: 7, shown below, is the polynucleotide sequence of an aptamer, where X is an abasic site. XXXXXXXXXXXXXXXXXXXXXXXXAAAAAAGGT TGGTGTGGTTGG. This sequence does not comply with WIPO ST.25 and so has not been included in the sequence listing.

SEQ ID NO: 8 shows the polynucleotide sequence of a strand of DNA. The strand has a BHQ1 label attached to the thymine at position 1 in the sequence and a FAM label attached to the thymine at position 15 in the sequence.

SEQ ID NO: 9 shows the polynucleotide sequence encoding the MspA-(B2C) mutant MspA monomer. The amino-acid sequence of MspA-(B2C) is a variant of SEQ ID NO: 2 with the following mutations G75S/G77S/L88N/Q126R.

SEQ ID NO: 10 shows the polynucleotide sequence encoding the MS-B1 mutant of the MspA monomer. This mutant includes the following mutations: D90N, D91N, D93N, D118R, D134R and E139K.

Figure 1:
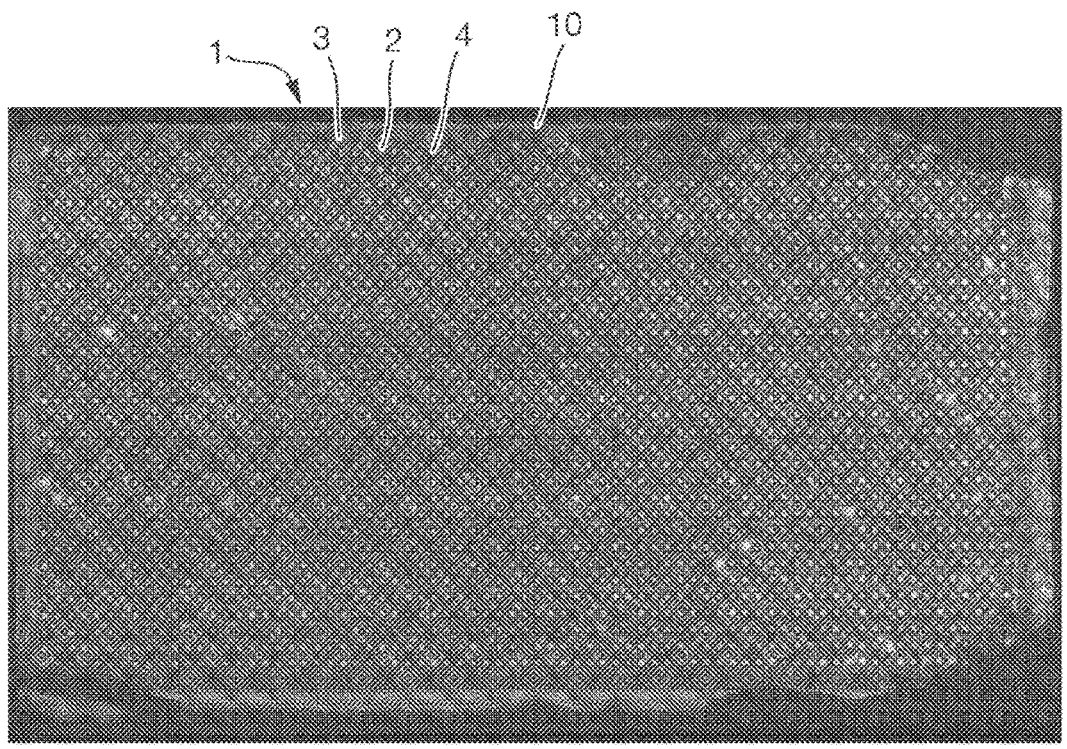
FIG. 1 is an image in plan view of an apparatus holding an array of volumes of polar medium.

FIG. 1 shows an apparatus 1 holding an array of volumes 2 of a polar medium in apolar medium. The apparatus 1 comprises a support 3 providing an array of compartments 4. In use, all the compartments 4 contain apolar medium. At least some of the compartments 4 (in this example most of the compartments 4) contain single volumes 2 of a polar medium in the apolar medium.

Figure 2:
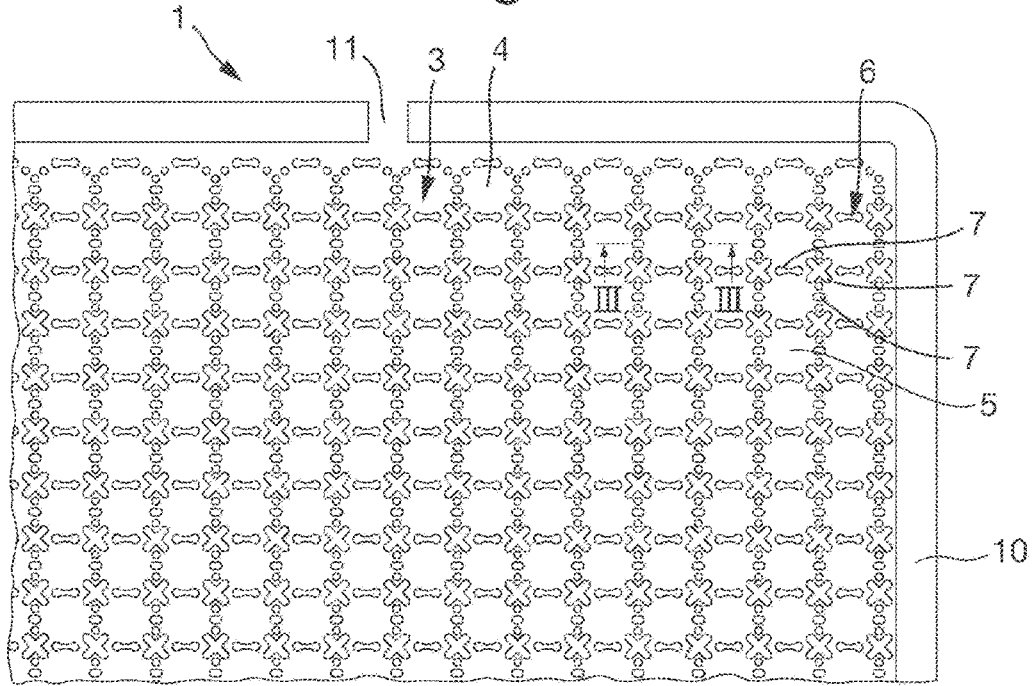
FIG. 2 is a partial plan view of the support of the apparatus of FIG. 1.
Figure 3:
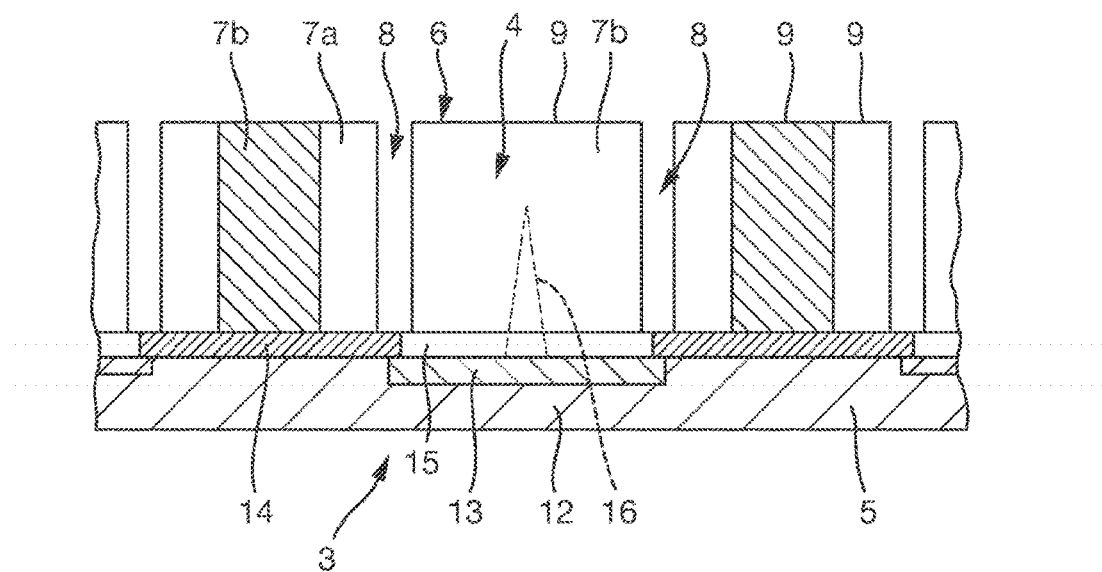
FIG. 3 is a cross-sectional side view of a single compartment of the support taken along line in FIG. 2.

The construction of the support 3 is shown in more detail in FIGS. 2 and 3. The support 3 comprises a base 5 and partitions 6 that extend from the base 5. The partitions 6 comprise plural pillars 7 that extend out from the base 5 as shown in FIG. 3, in this example perpendicularly. The compartments 4 have openings provided at the distal ends of the pillars 7. These openings provide communication from the compartments 4 into the space adjacent the support 3, and volumes of polar medium may be introduced into the compartments 4 through the openings.

The pillars 7 may have different shapes as shown in FIG. 2 so that they define the compartments 4 in a regular square array. The pillars 7 are shaped so that they constrain the volumes 2 of polar medium in the compartments 4 from contacting volumes 2 comprising polar medium in neighbouring compartments. In this example, the pillars 7 include a cross-shaped pillar 7a in the corners of compartments 4 with arms protruding into the compartment 4 and further pillars 7b along the each side of the compartment 4, with gaps 8 between the cross-shaped pillars 7a and the further pillars 7b. The compartments 4 are arranged such that the volumes 2 of polar medium are physically separated from each other. This prevents the volumes 2 of polar medium from merging or contacting each other to form interfaces. This provides a very stable array of volumes 2 of polar medium which is capable of being stored over a long period of time. Herein, the terms "inner" and "outer" describe relative locations within the compartments 4 from the openings at the outer end towards the base 5 at the inner end.

The pillars 7 have gaps 8 therebetween. In this example, the gaps 8 extend the entire distance from the openings to the base 5. The gaps 8 are of sufficient size to allow the flow of an apolar medium between the compartments 4, whilst maintaining the separation of the volumes 2 of polar medium in the compartments 4. The provision of gaps 8 allows the apolar medium to flow between the compartments 4. This greatly aids in filling of the compartments 4 as apolar medium may be displaced by a volume 2 of polar medium entering a compartment 4 through an opening. The gaps 8 also allow the level of apolar medium in the support 3 to be controlled and equalised across the array. The gaps 8 between the pillars 7 are such that the volumes 2 of polar medium are constrained from moving through the gaps 8 between the compartments 4 or from contacting volumes 2 comprising polar medium in neighbouring compartments.

Optionally, a dam 10 may be provided around the perimeter of the support 3 which aids in filling the peripheral edges of the support 3 with apolar medium. One or more channels 11 may be provided in the dam 10 through which apolar medium may be introduced or drained from the support 3.

The support 3 may be prepared from a range of different materials having a high electrical resistance, including without limitation undoped crystalline silicon (i.e. a silicon wafer), SU8, polycarbonate, and/or polyester, and including any combination of these or other materials. The support 3 may be manufactured using conventional techniques for such materials, including, without limitation, deposition and removal techniques for example etching or laser processing.

As shown in FIG. 3, the base 5 comprises a substrate 12. The substrate 12 supports an electrode 13 in each compartment 4. In this example, the electrodes 13 are shown recessed into the substrate 12, but they could alternatively be deposited as an outer layer on an exposed surface of the substrate 12. The electrodes 13 are provided to make electrical contact with the volumes 2 of polar medium contained in the compartments 4 and are discussed in more detail below.

The substrate 12 may comprise a surface coating 14 that is optional. The surface coating 14 may provide a high resistance outer layer. One possible combination of materials for the base 5 is that the base is made of undoped crystalline silicon (i.e. a silicon wafer) and the coating 14 to be made of SU8. In the example shown in FIG. 2, the surface coating 14 is provided on top of the substrate 12 and so has apertures 15 aligned with the electrodes 13 to allow electrical contact between the electrodes 13 and the volumes 2 of polar medium. As an alternative the electrodes 12 could be patterned in the same layer as the surface coating 14 or on top of the surface coating 14.

The partitions 6 may be made of the same or different material to the base 12 of the support 3 and may have the same or different surface properties. The partitions 6 are typically apolar and may be made for example from Permex. The partitions 6 may optionally comprise a surface coating (not shown) to modify their electrical and/or physical properties.

The particular shapes and arrangement of the pillars 7 shown in FIG. 2 is not essential and the pillars 7 may have a variety of different shapes to define the compartments 4 so as to constrain the volumes 2 of polar medium in the compartments 4 from contacting volumes 2 comprising polar medium in neighbouring compartments. By way of example, FIGS. 4 to 8 show some examples of alternative shapes and arrangements for the pillars 7, as follows.

Figure 4:
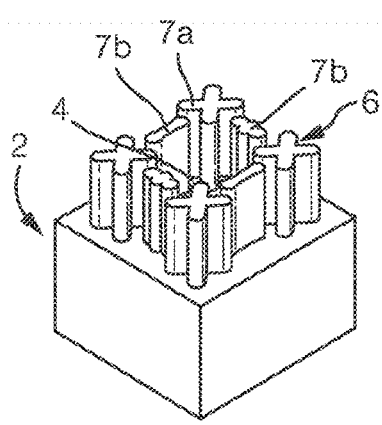
FIG. 4 is an isometric projection of an alternative pattern for pillars of the partitions defining compartments.
Figure 5:
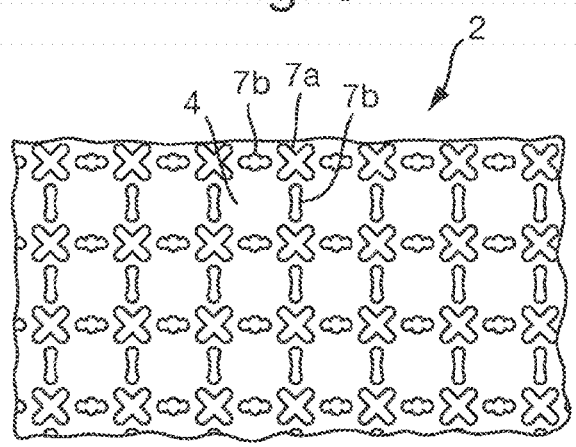
FIG. 5 is a plan view of the pillars in the pattern of FIG. 4.

FIGS. 4 and 5 show a support 3 wherein the partitions 6 comprise pillars 7 including cross-shaped pillars 7a and further pillars 7b in a similar arrangement to FIG. 2. Thus the pillars 7 are combined with short and long pitches to prevent merging of the volumes 2 of polar medium and improve pillar stability.

Figure 6:
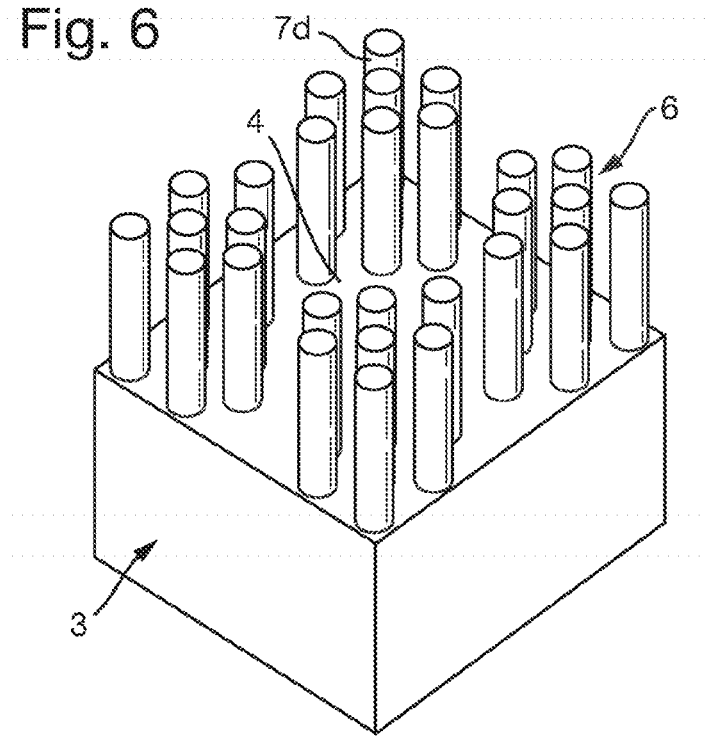
FIGS. 6 and 7 are isometric projections of further alternative patterns for the pillars.

FIGS. 6 to 9 show other supports 3 in which the pillars 7 have modified shapes and patterns. In each case, pillars 7 have gaps 8 that extend the entire distance from the openings to the base 5. The pillars 7 are arranged in a pattern that defines compartments 4 in regions of the support 3 where the pillars 7 are widely spaced from each other. The gaps 8 between the pillars 7 are such that the volumes 2 of polar medium are constrained from moving between the compartments 4 or from contacting volumes 2 comprising polar medium in neighbouring compartments. In FIG. 6, the partitions 6 comprise an array of circular pillars 7d.

Figure 7:
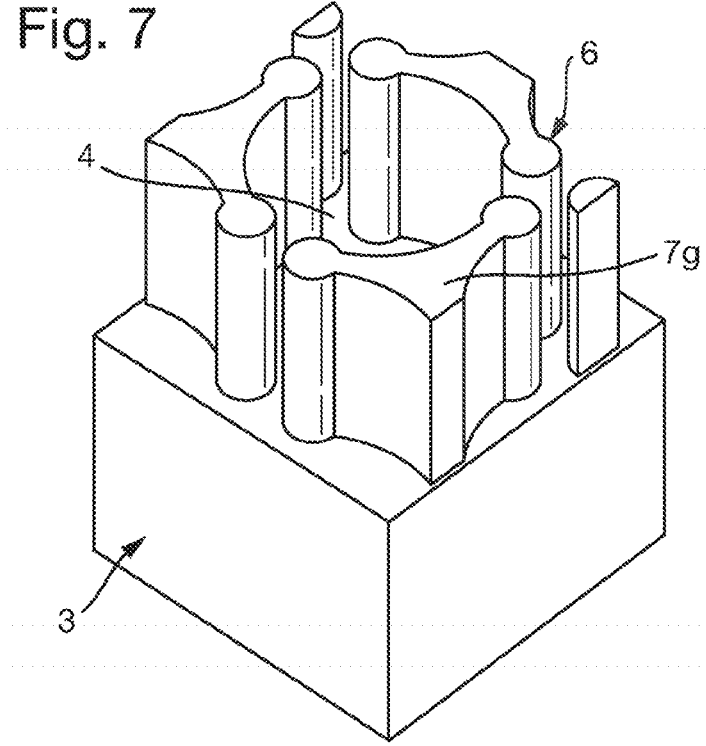
Figure 8:
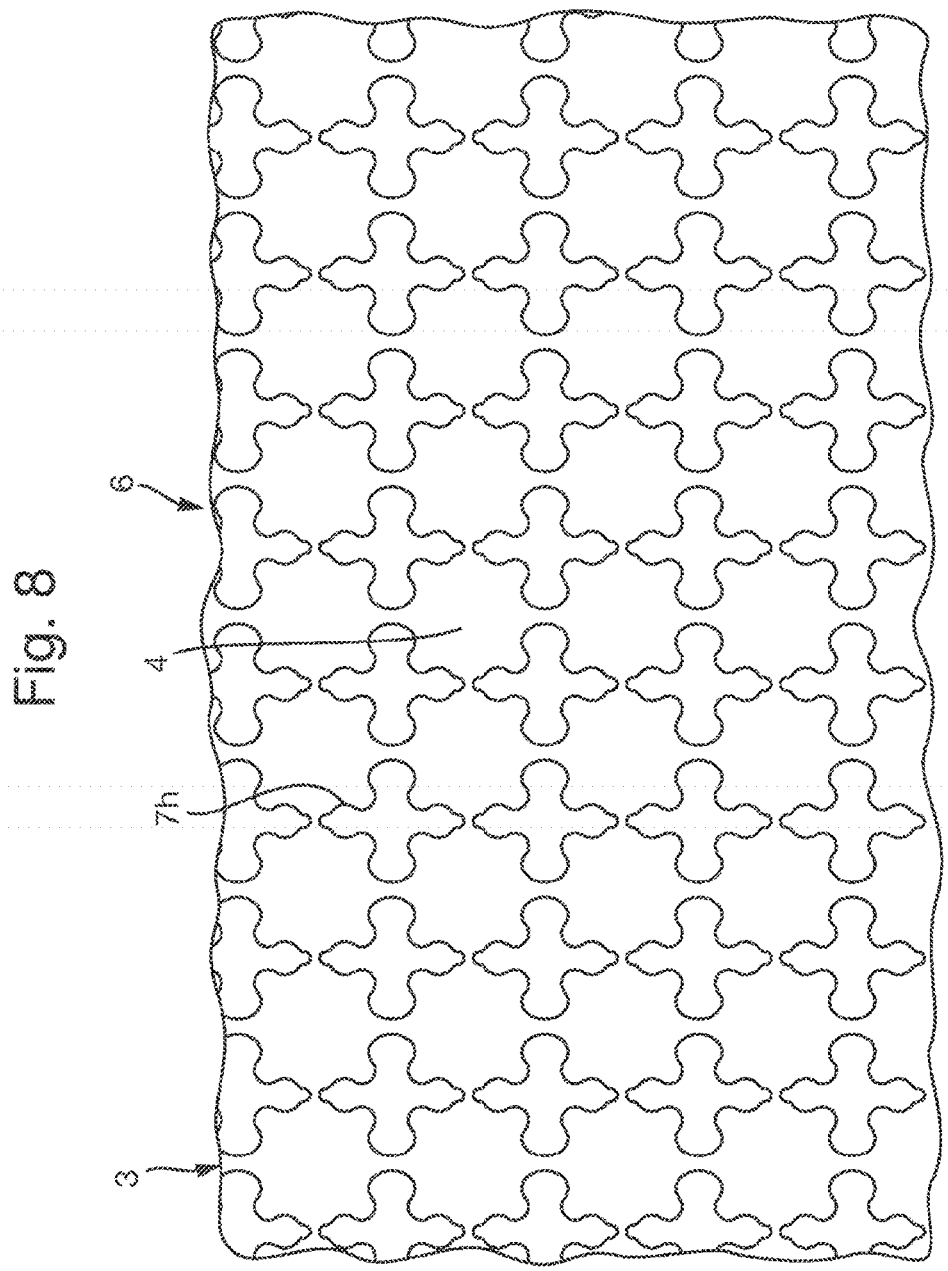
FIGS. 8 and 9 are plan views of further alternative patterns for the pillars.
Figure 9:
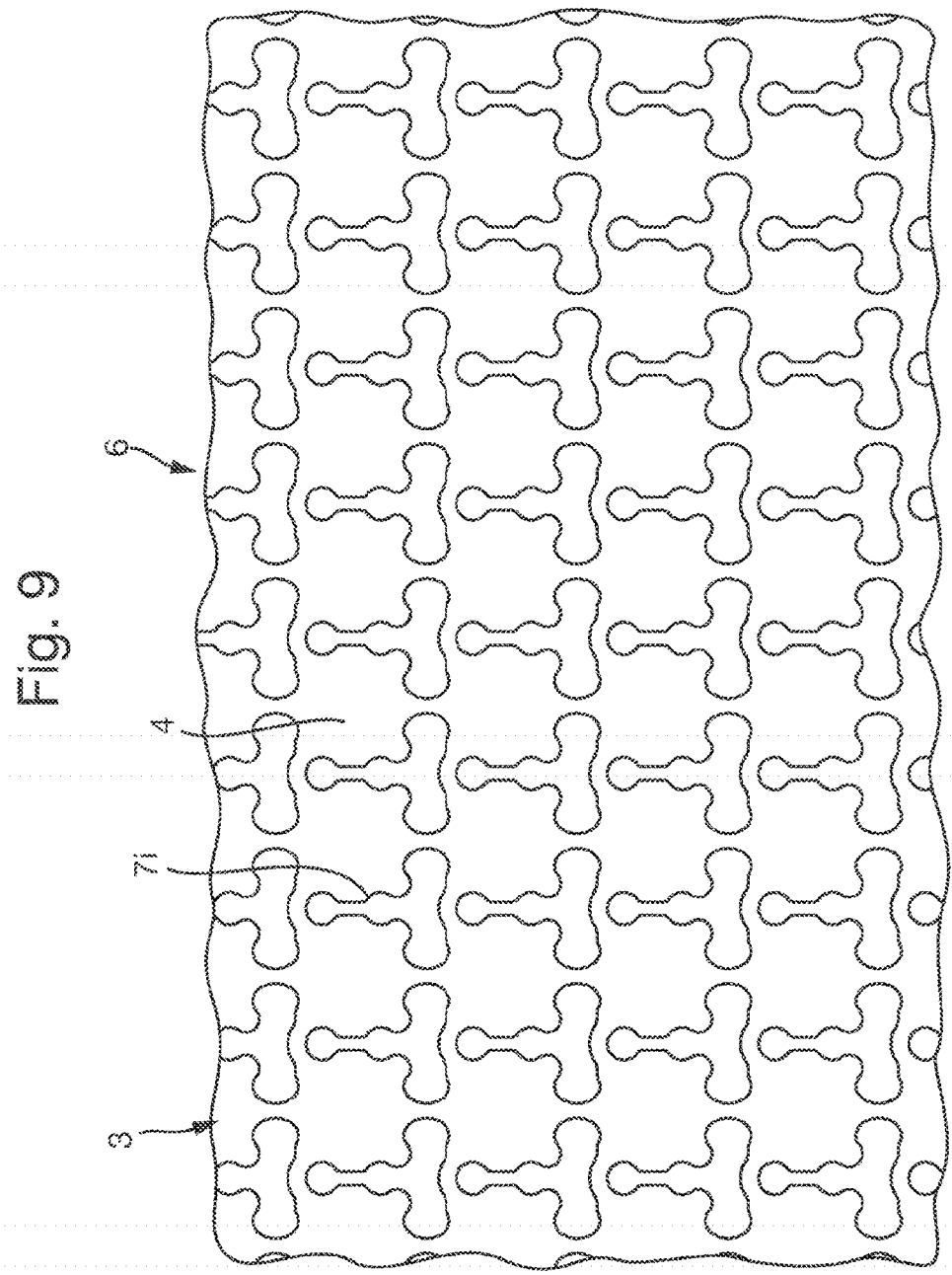
Figure 10:
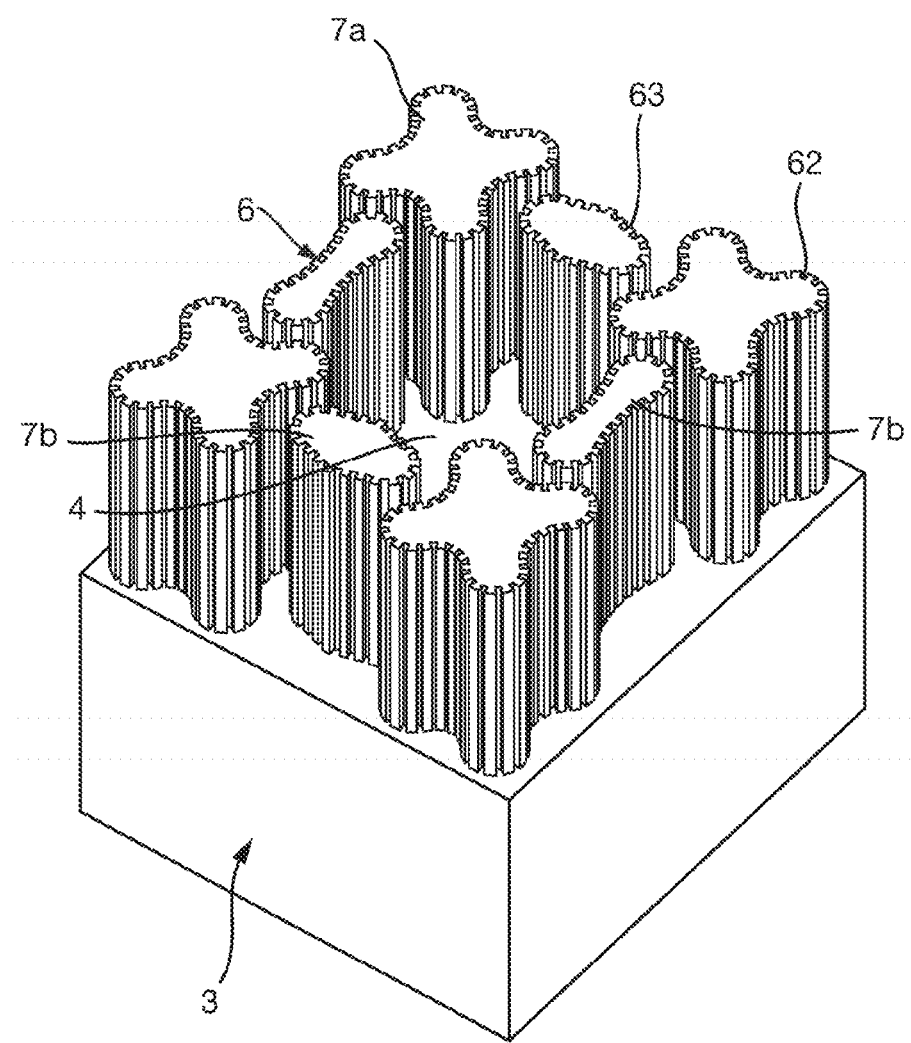
FIG. 10 is an isometric projection of an alternative pattern for pillars of the partitions defining compartments.

In FIG. 7 the partitions 6 comprise an array of tri-star pillars 7g. The tri-star pillars 7g have three arms with curved re-entrant sides and enlarged ends. The tri-star pillars 7g define a plurality of compartments 4, with three tri-star pillars 7g equi-spaced around each compartment. In FIGS. 8 and 9, the partitions 6 comprise an array of cross-shaped pillars 7h and T-shaped pillars 7i, respectively, defining a plurality of compartments 4. The cross-shaped pillars 7g and T-shaped pillars 7h have re-entrant sides.

In these examples of FIGS. 7 to 9, the number of pillars 7 that are required to provide a compartment 4 is less than for example the arrangement of FIG. 2 or 6. The provision of a reduced number of pillars 7 makes fabrication of the array easier and increases the mechanical resilience of the individual pillars.

It has also been found that the circular pillars as shown in FIG. 6 are mechanically less resilient and are more prone to collapse, or distortion than the more structurally resilient pillars of for example FIG. 4 or FIGS. 7 to 9, especially for pillars 7 of heights of the order of 100 µm and pillar widths of the order of 25 µm. Pillars 7 having a higher width:height ratio are therefore preferred.

Figure 11:
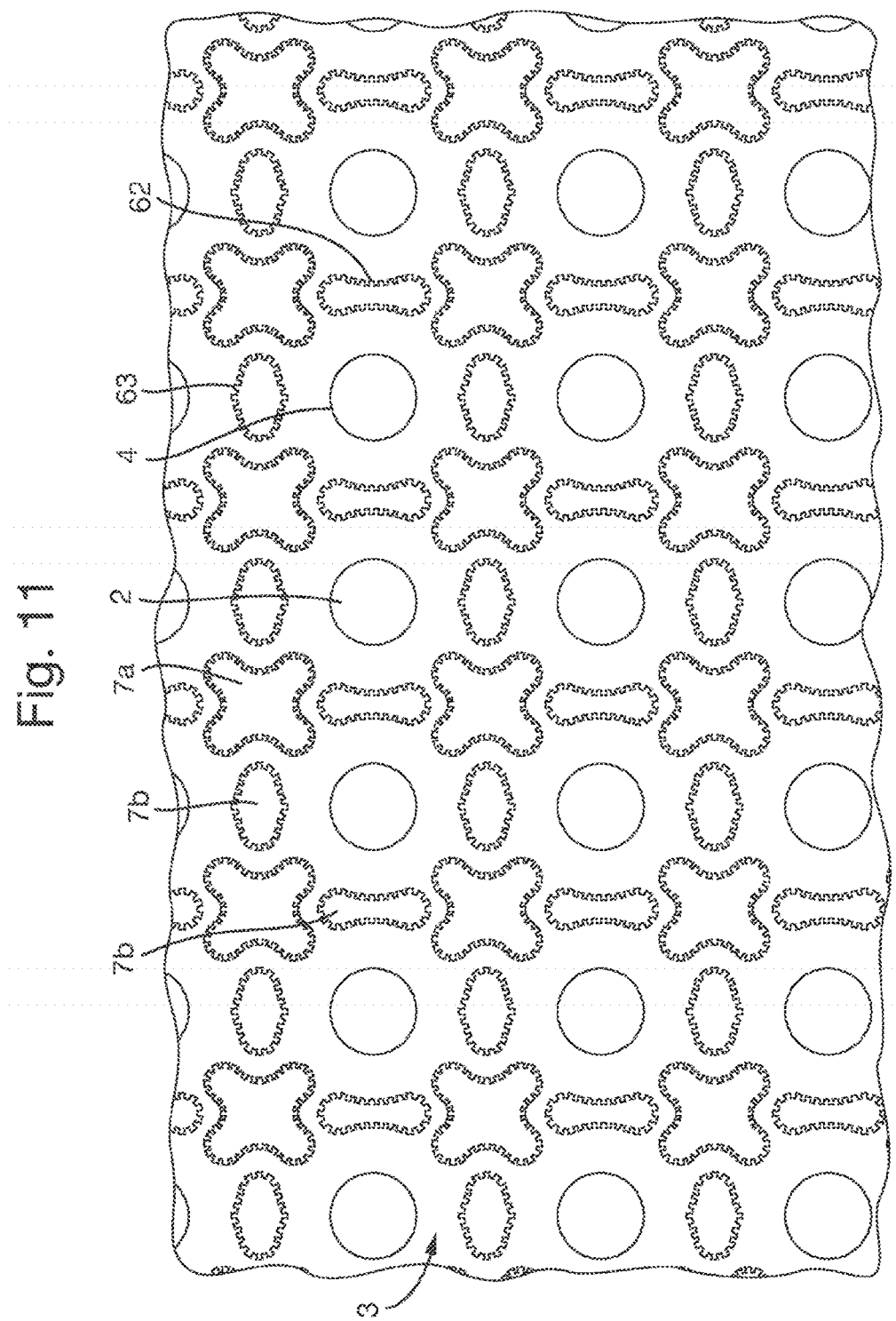
FIG. 11 is a plan view of the pillars in the pattern of FIG. 10.
Figure 12:
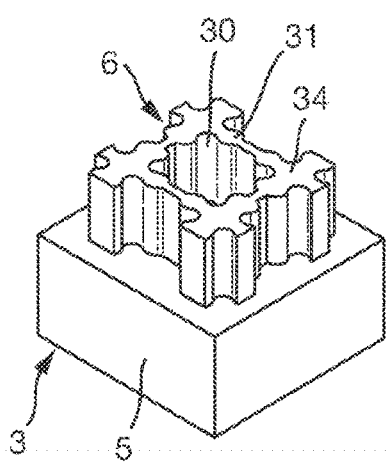
FIG. 12 is an isometric projection of a first alternative construction for the partitions.

FIGS. 11 and 12 show a support 3 wherein the partitions 6 comprise pillars 7 including cross-shaped pillars 7a and further pillars 7b having the same overall arrangement as FIG. 4 except for a modification that the surfaces 62 of the cross-shaped pillars 7a and further pillars 7b are micro-patterned with a patterning as follows. In particular, those surfaces 62 are indented with a plurality of indentations 63 that extend outwardly of the compartment 4, along the entire length of the cross-shaped pillars 7a and further pillars 7b.

In this example, the indentations 63 are rectangular in cross-section.

The surfaces 62 between the indentations 63 lie in a common curved plane extending around the compartment 4. These surfaces 62 physically constrain a volume 2 of polar medium inside the compartment 4. Thus, the dimensions of the surfaces 62 control the size of the volume 2 of polar medium that may be accommodated in the compartment 4.

The indentations 63 hold apolar medium that reduces the surface area of the partitions 6 that is in contact with a volume 2 of polar medium. This modifies the surface properties of the pillars 7, repelling polar medium and therefore assisting in constraining a volume 2 of polar medium held in the compartment 4, and in allowing entry of the polar medium into the compartment. In general, the patterning could comprise other surfaces features to achieve this effect.

The indentations 63 and surfaces 62 have widths that are small compared to the size of the volume of volume 2 of polar medium held in the compartment 4. The indentations 63 and surfaces 62 have widths preferably of at most 20 µm, more preferably of at most 10 µm. For example, if the dimensions of a compartment 4 are characterised with reference to the diameter d of the largest notional sphere that can be accommodated within the compartment 4, then the indentations 63 and surfaces 62 have widths that are at most 0.1d, preferably at most 0.05d. In a typical example where the diameter d is 140 µm, the indentations 63 and surfaces 62 have widths that are 5 µm. The depth of the indentations 63 is chosen to allow the channels to retain the apolar medium. In the example of FIGS. 11 and 12, the channels have a depth of 5 µm, providing an aspect ratio of 1:1. However, deeper indentations 63 provide more effective retention of apolar medium.

In all the constructions shown in the figures, the pillars 7 have the same height so that the outer ends 9 of the pillars 7 extend in a common plane, as shown in FIG. 3, to provide the support 3 with a brush-like planar upper surface. Whilst the provision of pillars having the same height is a preferred construction, constructions may be provided having pillars of differing heights.

There will now be described some alternative constructions for the partitions 6 in which the partitions 6 do not have pillars 7 and gaps 8 extending the entire distance to the base 5. In general, reducing the depth of any gaps in the partitions can increase the electrical isolation between compartments 4 and reduce the tendency for offset currents between the electrodes 13 of different compartments 4, for example if the apolar medium becomes hydrated sufficiently to provide an electrical conductivity path between electrodes 13. Apart from the alternative constructions of the partitions 6, supports 2 otherwise have the same construction as described above.

Figure 13:
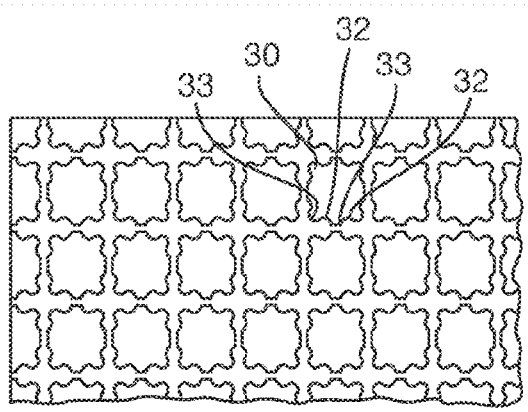
FIG. 13 is a plan view of the partitions of FIG. 12.

A first alternative construction for the partitions is shown in FIGS. 12 and 13 and arranged as follows. In the first alternative construction, the partitions 6 have no gaps allowing the flow of apolar medium between the compartments 4. In particular, the partitions 6 have recesses 30 that define the compartments 4 without gaps between those compartments 4. The partitions 6 may be formed by a common body 31 extending from the base 5. In that case, the base 5 has planar surfaces forming the inner ends of the compartments 4. The common body 31 may be formed as a separate layer laminated with the base 5, but alternatively may be integral with the base 5 and the recesses 30 formed by removing material.

In this example, the partitions 6 have a profile as viewed across the support 3 that is the same as the profile of the inner portion 20 of the partitions in the second alternative construction. That is, the profile is undulating and comprises, around individual compartments 4, plural salient portions 32 that protrude into the compartment 4 and plural re-entrant portions 33 where the compartment 4 protrudes into the partitions 6.

The salient portions 32 are arranged physically to constrain a volume 2 of polar medium inside the compartment 4. Thus, the dimensions of the salient portions 32 control the size of the volume 2 of polar medium that may be accommodated in the compartment 4.

The re-entrant portions 33 provide channels that extend outside a volume 2 of polar medium accommodated in the compartment 4. Therefore, the re-entrant portions 33 allow outflow of apolar medium displaced by entry of a volume 2 of polar medium into the compartment 4.

This undulating structure also reduces the surface area of the partitions 6 that is in contact with a volume 2 of polar medium. This serves to allow the a volume 2 of polar medium to move to the base of the compartment 4 and thereby assist in making electrical contact with the electrode 13.

In principle, any number of re-entrant portions 33 could in principle be provided such as 3, 4, 5, 6 etc. However one would need to balance the number of salient portions 32 with the contact surface for the volume 2 of polar medium.

The salient portions 32 as shown in FIG. 12 have rounded edges. Alternatively the salient portions 32 may have sharp edges. Such sharp edges may reduce further the extent of contact between the edge of the compartment 4 and the volume 2 of polar medium. Conversely, sharp edges may puncture the layer of amphiphilic molecules. It is advantageous to reduce the extent of contact of the volume 2 of polar medium with the inner surface of the compartment 4. Having salient portions 32 enables larger volumes 2 of the polar medium to be used for a given volume of compartment 4.

As can be seen from FIG. 12, the dimensions and shape of the re-entrant portions 33 determines the surface area which is capable of being contacted by a volume 2 of polar medium. The salient portions 32 and re-entrant portions 33 are interrelated in that generally the greater the cross-sectional width of the re-entrant portion 33, the greater the reduction in surface area of the walls of the compartment 4.

Thus, compared to the constructions described above, in the first alternative construction, the partitions 6 provide the same function of constraining the volumes 2 of polar medium and preventing them from contacting or merging, but the electrical isolation between compartments 4 is increased due to the absence of gaps in the partitions 6. The absence of gaps in the partitions 6 also reduces the beneficial effect of allowing flow of apolar medium between compartments 4, but this is to some extent mitigated when filling compartments 4 by the re-entrant portions 33 providing channels allowing outflow of displaced apolar medium which assists insertion of a volume 2 of polar medium. This allows for a volume 2 of polar medium of maximum size to be inserted, the movement of which is constrained by the salient portions 32.

The partitions 6 have the same height so that the outer ends 34 of the partitions 6 extend in a common plane, as shown in FIG. 12, to provide the support 3 with a brush-like planar upper surface.

There will now be described some alternative constructions for the partitions 6 in which the partitions 6 comprise inner portions defining inner recesses of the compartments without gaps therebetween, and outer portions extending outwardly from the inner portions defining outer portions of the compartments with gaps allowing the flow of apolar medium between the compartments. Thus, effectively the gaps extend partway to the base 5. Apart from the alternative constructions of the partitions 6, the following supports 2 otherwise have the same construction as described above.

Figure 14:
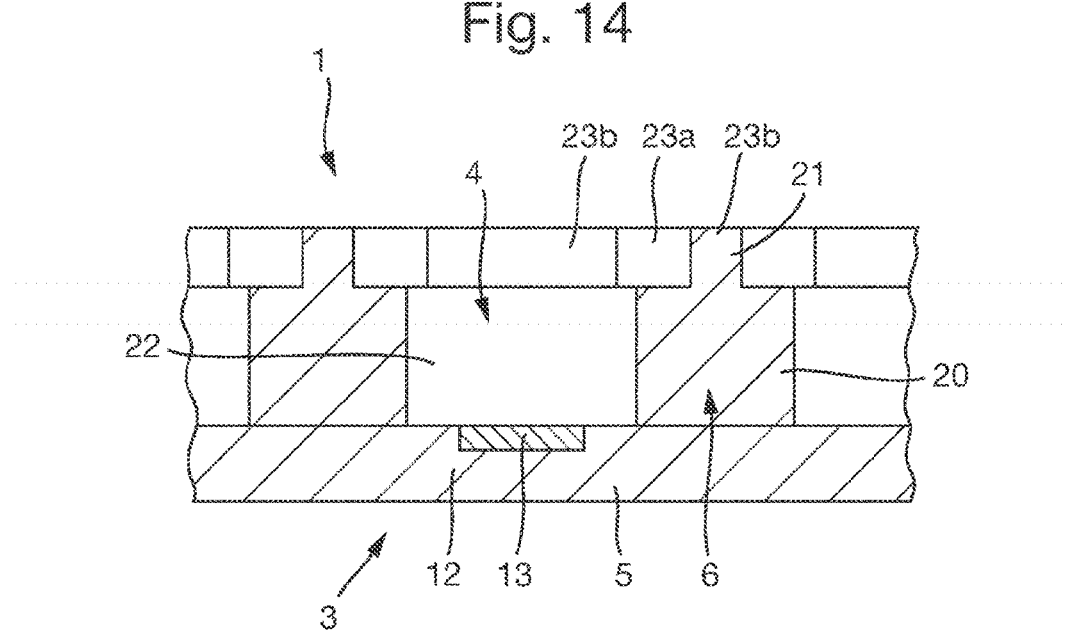
FIG. 14 is a cross-sectional side of a single compartment of a support of the apparatus in which the partitions have a second alternative construction.

A second alternative construction for the partitions is shown in FIGS. 14, 15 and 16 and arranged as follows.

The apparatus 1 for holding an array of volumes 2 of a polar medium in apolar medium comprises a support 3 providing an array of compartments 4. In use, all the compartments 4 contain apolar medium, and at least some of the compartments 4 contain single volumes 2 of a polar medium in the apolar medium.

The support 3 comprises a base 5 and partitions 6 that extend from the base 5. Herein, the terms "inner" and "outer" describe relative locations within the compartments 4 from the openings at the outer end towards the base 5 at the inner end.

As described in more detail below, the partitions 6 define compartments 4 having openings provided at the distal ends of the partitions 6. These openings provide communication from the compartments 4 into the space adjacent the support 3, and volumes of polar medium may be introduced into the compartments 4 through the openings. The compartments 4 are arranged such that the volumes 2 of polar medium are physically separated from each other. This prevents the volumes 2 of polar medium from merging or contacting each other to form interfaces. This provides a very stable array of volumes 2 of polar medium which is capable of being stored over a long period of time.

Optionally, a dam (taking the form shown in FIG. 1) may be provided around the perimeter of the support 3 which aids in filling the peripheral edges of the support 3 with apolar medium. One or more channels may be provided in the dam through which apolar medium may be introduced or drained from the support 3.

The support 3 may be prepared from a range of different materials having a high electrical resistance, including without limitation undoped crystalline silicon (i.e. a silicon wafer), SU8, polycarbonate, and/or polyester, and including any combination of these or other materials. The support 3 may be manufactured using conventional techniques for such materials, including, without limitation, deposition and removal techniques for example etching or laser processing.

The base 5 comprises a substrate 12. The substrate 12 supports an electrode 13 in each compartment 4. In this example, the electrodes 13 are shown recessed into the substrate 12, but they could alternatively be deposited as an outer layer on an exposed surface of the substrate 12. The electrodes 13 are provided to make electrical contact with the volumes 2 of polar medium contained in the compartments 4 and are discussed in more detail below.

The substrate 12 may optionally comprise a surface coating. The surface coating may provide a high resistance outer layer. One possible combination of materials for the base 5 is that the base 5 is made of undoped crystalline silicon (i.e. a silicon wafer) and the coating to be made of SU8. Such a surface coating may be provided on top of the substrate 12 with apertures aligned with the electrodes 13 to allow electrical contact between the electrodes 13 and the volumes 2 of polar medium. As an alternative, the electrodes 12 could be patterned in the same layer as the surface coating or on top of the surface coating.

The partitions 6 may be made of the same or different material to the base 12 of the support 3 and may have the same or different surface properties. The partitions 6 are typically apolar and may be made for example from Permex. The partitions 6 may optionally comprise a surface coating (not shown) to modify their electrical and/or physical properties.

FIGS. 15 and 16 show a particular arrangement of the partitions 6, but this is not essential and the partitions 6 may have a variety of different arrangements to define the compartments 4 so as to constrain the volumes 2 of polar medium in the compartments 4 from contacting volumes 2 comprising polar medium in neighbouring compartments.

In the arrangement of FIGS. 15 and 16, the partitions 6 comprise inner portions 20 and outer portions 21.

The inner portions 20 of the partitions 6 define inner recesses 22 that form the inner portions of the compartments 4 without gaps between those inner portions of the compartments 4. The inner portions 20 of the partitions 6 may be formed by a common body extending from the base 5. In that case, the base 5 has planar surfaces forming the inner ends of the compartments 4. The inner portions 20 may be formed as a separate layer laminated with the base 5 after removal of material to form apertures that become the inner recesses 5. Alternatively the inner portions 20 may be integral with the base 5 and the recesses 22 formed by removing material of the integral member.

In this example, the inner portions 20 of the partitions 6 have a profile as viewed across the support 3 that is circular around individual compartments 4.

The outer portions 21 of the partitions 6 extend outwardly from the inner portions 20 and define the outer portions of the compartments 4. In this example, the outer portions 21 of the partitions 6 comprise plural pillars 23 that extend out from the inner portions 20 of the partitions 6 as shown in FIG. 15, in this example perpendicularly, with a similar pattern to the pillars 7 in the construction of the partitions 6 shown in FIGS. 4 and 5. In particular, a cross-shaped pillar 23a in the corners of the compartments 4 with arms extending towards the compartment 4 and plural further pillars 23b along the each side of the compartment 4, with gaps 24 between the cross-shaped pillars 23a and the further pillars 23b, and between the further pillars 23b.

The pillars 23 have gaps 24 therebetween. In this example, the gaps 24 extend to the inner portions 20 of the partitions and hence only partway to the base 5. The gaps 24 are of sufficient size to allow the flow of an apolar medium between the compartments 4, whilst maintaining the separation of the volumes 2 of polar medium in the compartments 4. The provision of gaps 24 allows the apolar medium to flow between the compartments 4. This aids in filling of the compartments 4 as apolar medium may be displaced by a volume 2 of polar medium entering a compartment 4. Further description of this is given below. The gaps 24 also allows the level of apolar medium in the support 3 to be controlled and equalised across the array. Thus, compared to the constructions described above, in the second alternative construction, the partitions 4 provide the same function of constraining the volumes 2 of polar medium and preventing them from contacting or merging, and the gaps 24 provide the same function to the gaps 8 of allowing flow of apolar medium between compartments 4. However, the electrical isolation between compartments 4 is increased due to the absence of gaps in the inner portions 20.

The pillars 23 are set back from the edges of the inner recesses 22 as viewed from the openings of those inner recesses 22. This creates a step on the upper surface of the inner portions 20 of the partitions 6 between any given pillar 23 and the adjacent inner recesses 22.

The pillars 23 have the same height so that the outer ends 25 of the pillars 24 extend in a common plane, as shown in FIG. 15, to provide the support 3 with a brush-like planar upper surface.

The relative heights of the inner portions 20 and outer portions 21 of the partitions 6 may be varied. In one typical embodiment, the inner portions 20 have a height of 90 µm and a diameter of 170 µm, and outer portions 21 have a height of 60 µm.

In this example, the inner portions of the partitions further comprise two re-entrant portions 28. As can be seen from FIGS. 15 and 16, the dimensions of the re-entrant portions are relatively small compared to the inner surface of compartment 4.

Figure 17:
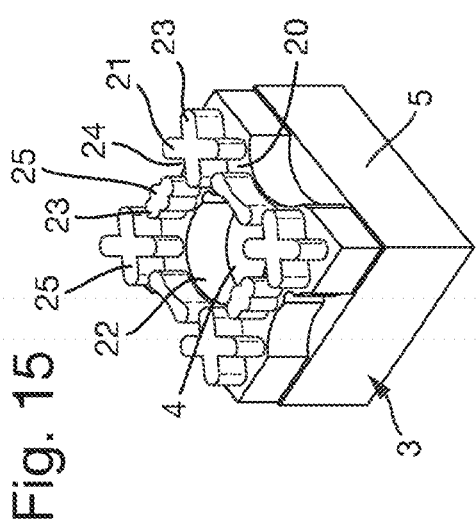
FIG. 17 is an isometric projection of a modified construction for the partitions.
Figure 18:
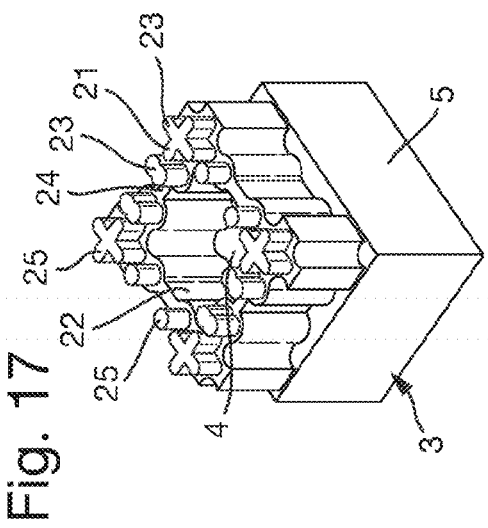
FIG. 18 is a plan view of the partitions of FIG. 17.

A modified construction for the partitions is shown in FIGS. 17 and 18. This is similar to the construction of FIGS. 15 and 16 except for the following modifications.

Firstly, the inner recesses 22 formed by the inner portions 20 of the partitions 6 have a profile as viewed from the openings of the compartments 4 across the support 3 that is not circular. In particular, the profile is undulating and comprises, around individual compartments 4, plural salient portions 26 that protrude into the compartment 4 and plural re-entrant portions 27 where the compartment 4 protrudes into the partitions 6.

The salient portions 26 are arranged physically to constrain a volume 2 of polar medium inside the compartment 4. Thus, the dimensions of the salient portions 26 control the size of the volume 2 of polar medium that may be accommodated in the compartment 4.

The re-entrant portions 27 provide channels that extend outside a volume 2 of polar medium accommodated in the compartment 4. Effectively therefore, the inner portions 20 of the partitions 6 have surfaces that are indented with a plurality of channels that extend outwardly of the inner recesses 22. Therefore, the re-entrant portions 27 allow outflow of apolar medium displaced by entry of a volume 2 of polar medium into the compartment 4.

This undulating structure also reduces the surface area of the partitions 6 that is in contact with a volume 2 of polar medium. This serves to allow a volume 2 of polar medium to move to the base of the compartment 4 and thereby assist in making electrical contact with the electrode 13.

In principle, any number of re-entrant portions 27 could in principle be provided such as 3, 4, 5, 6 etc. However one would need to balance the number of salient portions 26 with the contact surface for the volume 2 of polar medium.

Secondly, the pillars 23 of the outer portions 21 of the partitions 6 have a different pattern. In particular, a cross-shaped pillar 23c in the corners of the compartments 4 with arms extending in a direction along the side of the compartment 4 and a pair of further pillars 23c along the each side of the compartment 4, with gaps 24 between the cross-shaped pillars 23c and the further pillars 23d, and between the further pillars 23d. This is enable the pillars 23 to fit on the inner portion 20, but the pillars 23 have the same function and effect.

The salient portions 26 as shown in FIG. 17 have rounded edges. Alternatively the salient portions 26 may have sharper edges. It is advantageous to reduce the extent of contact of the volume 2 of polar medium with the inner surface of the compartment 4. Having salient portions 26 enables larger volumes 2 of the polar medium to be used for a given volume of compartment 4.

As can be seen from FIG. 17, the dimensions and shape of the re-entrant portions 27 determines the surface area which is capable of being contacted by a volume 2 of polar medium. The salient portions 26 and re-entrant portions 27 are interrelated in that generally the greater the cross-sectional width of the re-entrant portion 27, the greater the reduction in surface area of the walls of the compartment 4.

Figure 20:
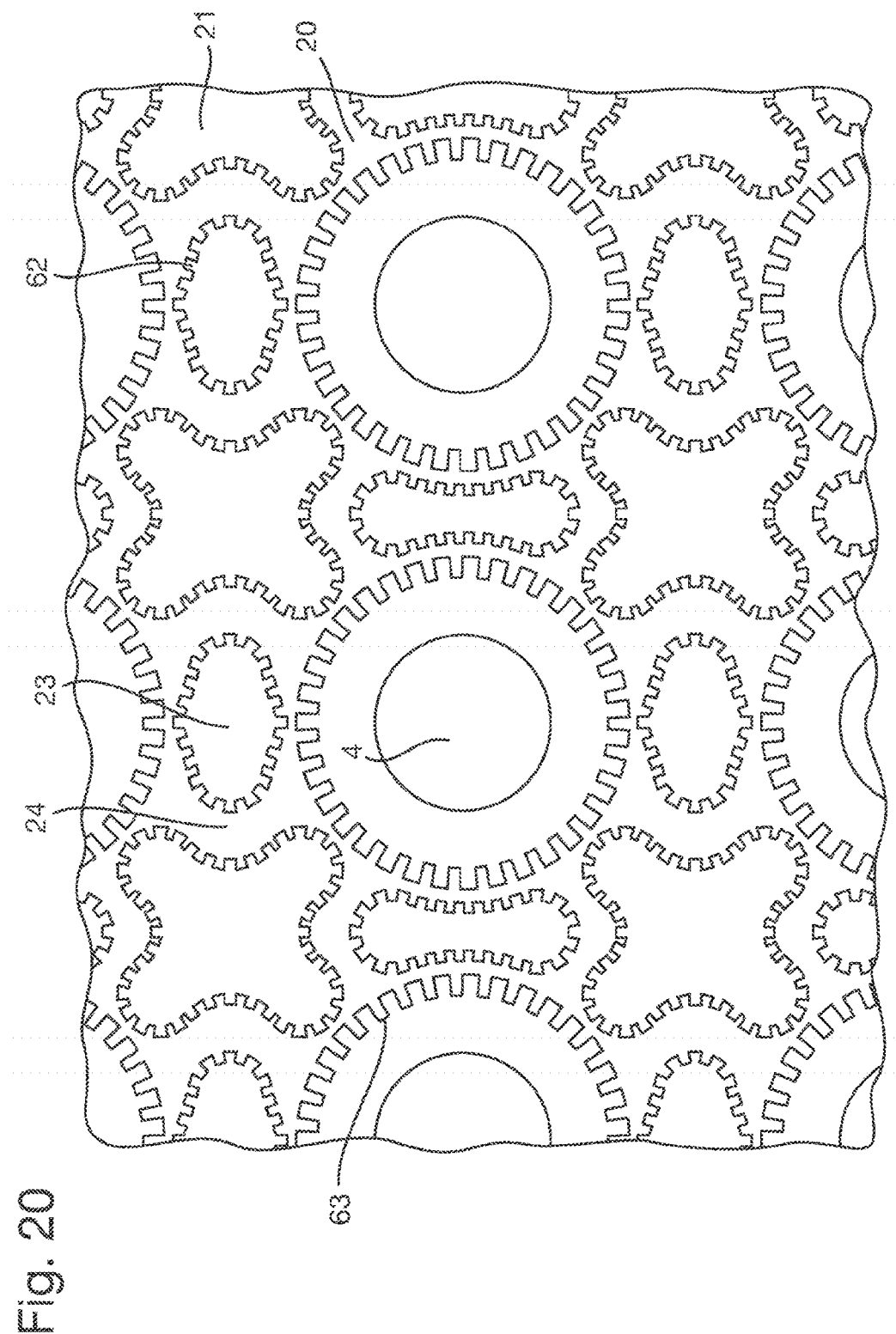
FIG. 20 is a plan view of the partitions of FIG. 19.

A modified construction for the partitions 6 is shown in FIGS. 19 and 20. This is similar to the construction of FIG. 15 except for a modification that the surfaces 64 of the inner recesses 22 and the surfaces 66 of the pillars 23 have a patterning described further below.

Figure 22:
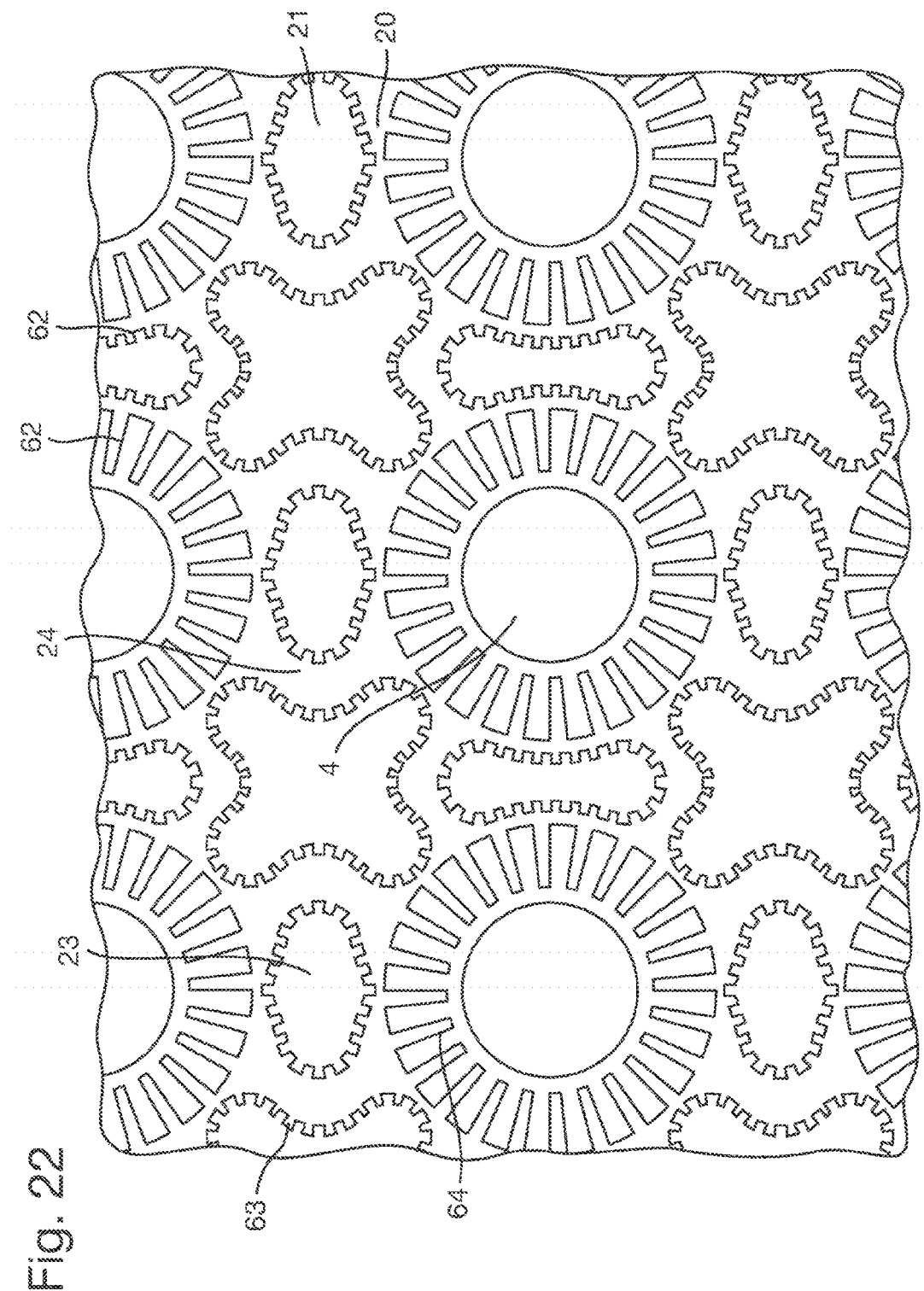
FIG. 22 is a plan view of the partitions of FIG. 21.

A yet further modified construction for the partitions 6 is shown in FIGS. 21 and 22. This is the same as the construction of FIG. 19 except for the size of the patterning.

Figure 23:
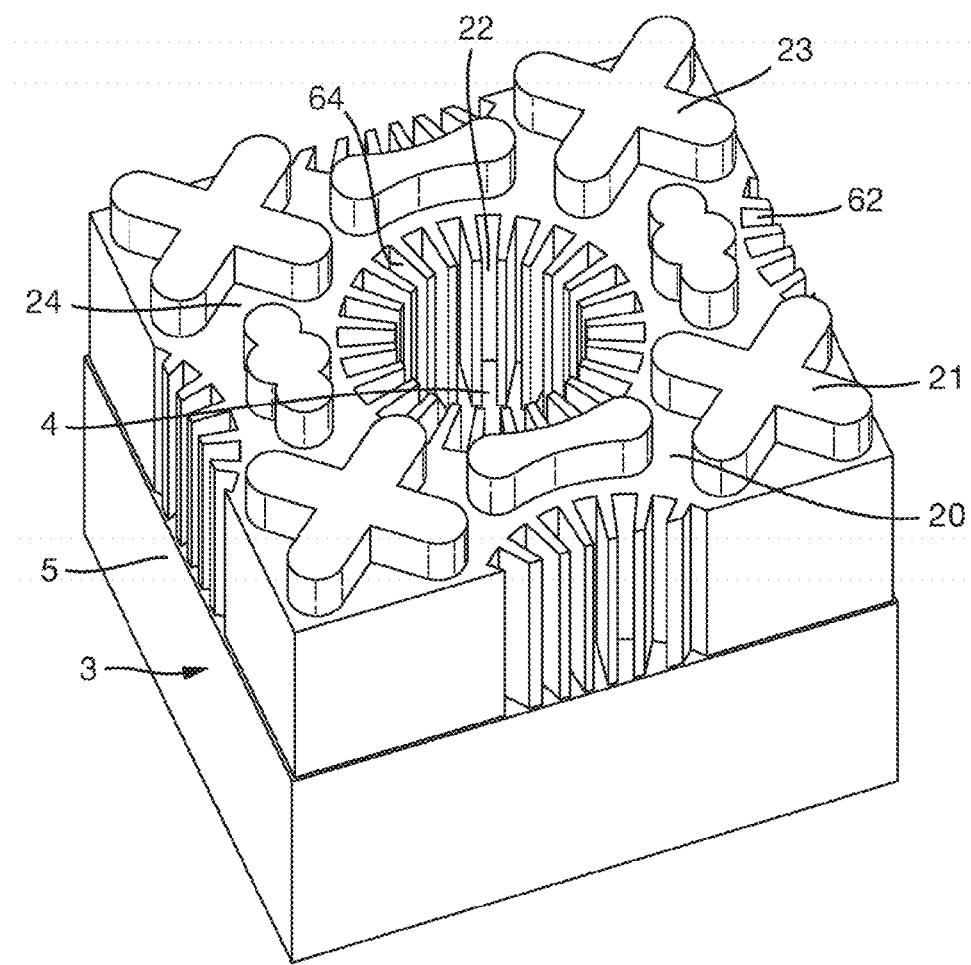
FIG. 23 is an isometric projection of a modified construction for the partitions.
Figure 24:
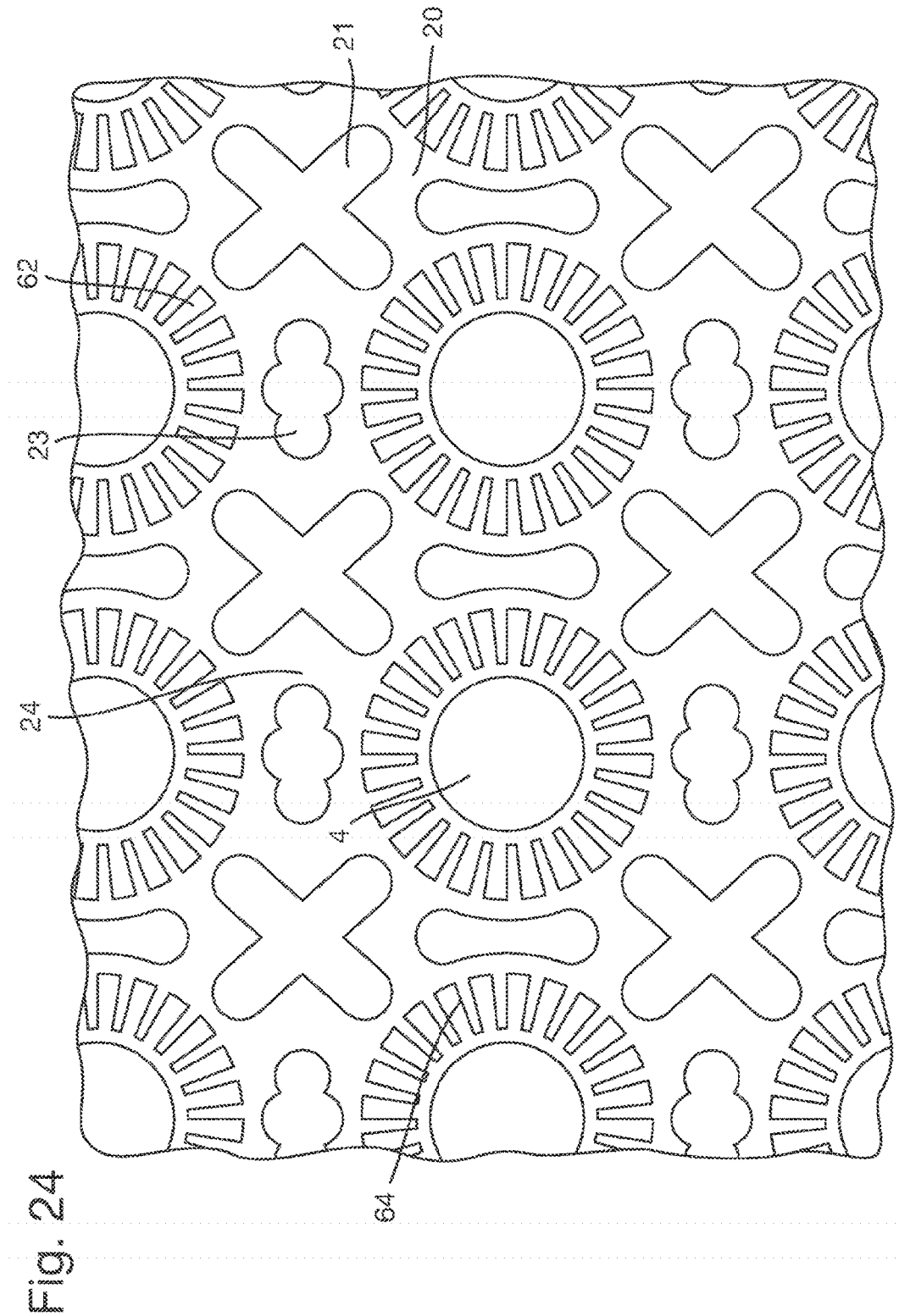
FIG. 24 is a plan view of the partitions of FIG. 23.

A yet further modified construction for the partitions 6 is shown in FIGS. 23 and 24. This is the same as the construction of FIG. 15 except for a modification that the surfaces 64 of the inner recesses 22 (but not the surfaces 66 of the pillars 23) have a patterning as described below.

Figure 25:
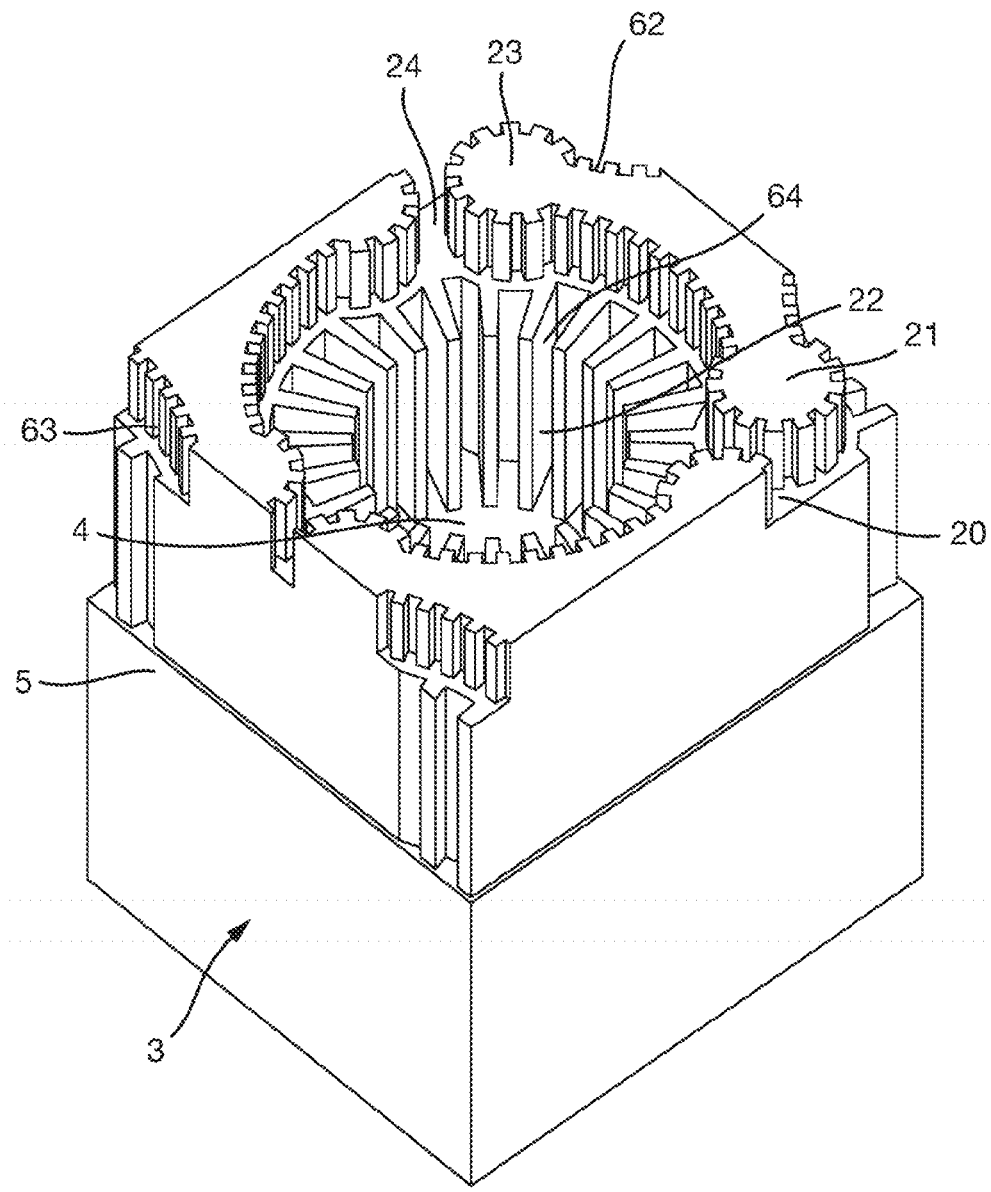
FIG. 25 is an isometric projection of a modified construction for the partitions.
Figure 26:
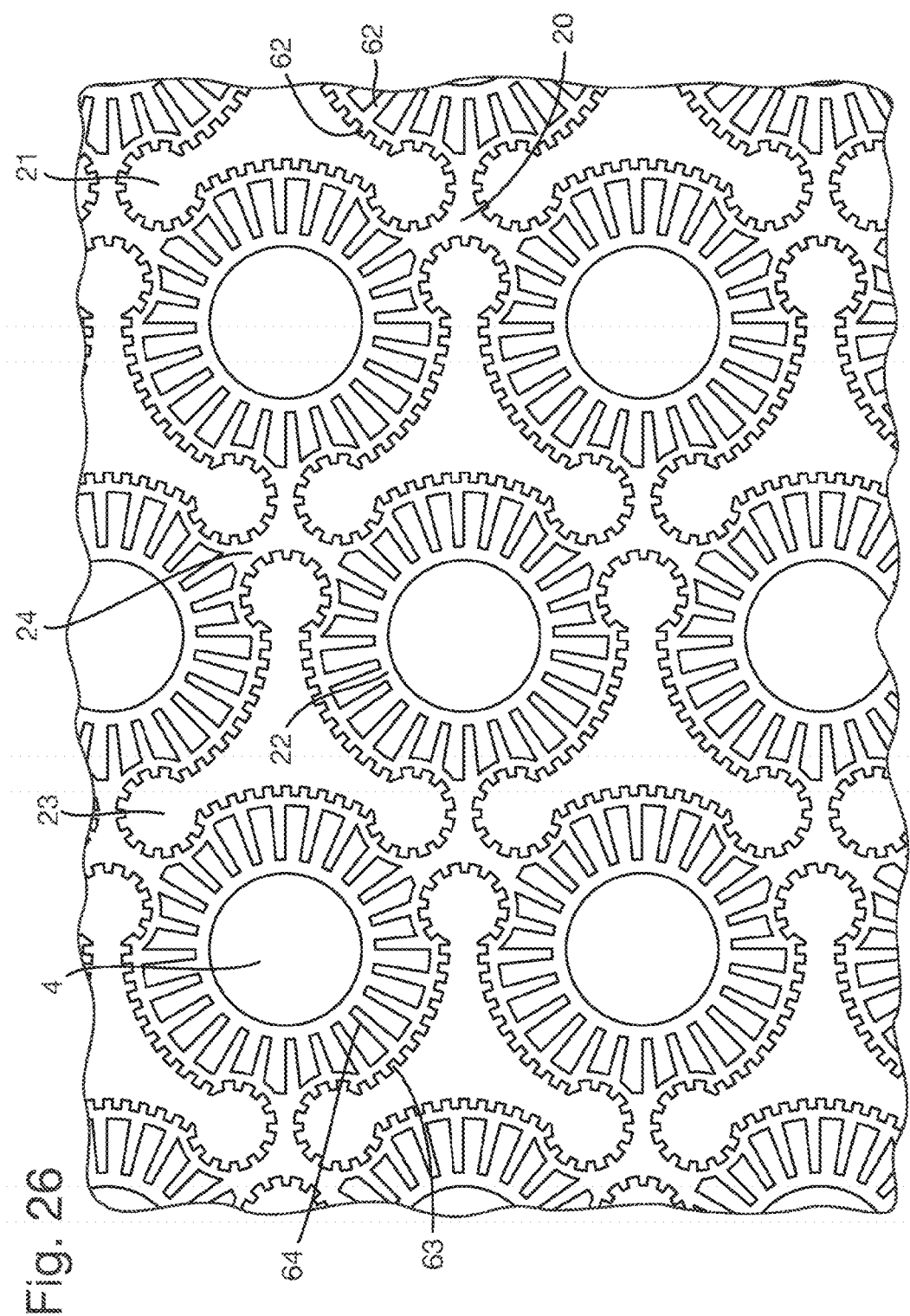
FIG. 26 is a plan view of the partitions of FIG. 25.

A yet further modified construction for the partitions 6 is shown in FIGS. 25 and 26.

The patterning on the various surfaces of the compartments 4 shown in FIGS. 19 to 26 will now be described in more detail.

In particular, the surfaces 64 of the inner recesses 22 are indented with a plurality of indentations 65 that extend outwardly of the inner recesses 22, and hence outwardly of the compartments 4, along the entire length of inner recesses 22. In this example, the indentations 65 are rectangular in cross-section. Similarly, surfaces 66 of the pillars 23 are indented with a plurality of indentations 67 that extend outwardly of the compartments 4 (except in the construction of FIG. 15). In this example, the indentations 67 are rectangular in cross-section.

The surfaces 64 of each inner recesses 22 between the indentations 65 lie in a common curved plane extending around the inner recess 22. These surfaces 64 physically constrain a volume 2 of polar medium inside the inner recess 22. Thus, the dimensions of the surfaces 64 control the size of the volume 2 of polar medium that may be accommodated in the inner recess 22.

The indentations 65 hold polar medium that reduces the surface area of the partitions 6 that is in contact with a volume 2 of polar medium. This modifies the surface properties of the pillars 7, repelling polar medium and therefore assisting in constraining a volume 2 of polar medium held in the inner recess 22, and in allowing entry of the polar medium into the inner recess 22. In general, the patterning could comprise other surfaces features to achieve this effect.

An initial pre-treatment of apolar medium 70 is applied as described below. The indentations 65 and 67 assist in spreading the pre-treatment of apolar medium 70 by wicking it over the substrate 3.

The pre-treatment of apolar medium 70 added to the partitions 6 is held within the indentations 65 by surface tension/capillarity which serves to increase the phobicity of the partitions 6 to the polar medium and therefore the contact angle between the volume 2 of polar medium and the partitions 6. This helps define the shape of the meniscus of the volume 2 of polar medium. Indentations 65 having a high capillarity are preferred as they retain the apolar medium more effectively and prevent or hinder flow of apolar medium onto the surface of the electrode 12. Thus polar medium added subsequently to the compartments is able to directly contact the electrodes 13.

The indentations 65 and surfaces 64 have widths according to an embodiment preferably of at most 20 μm, more preferably of at most 10 μm. The indentations 65 and surfaces 64 have widths that is small compared to the size of the volume of volume 2 of polar medium held in the inner recess 22. For example, if the dimensions of the inner recess 22 are characterised with reference to the diameter d of the largest notional sphere that can be accommodated within the inner recess 22, then the indentations 65 and surfaces 64 have widths that are preferably at most 0.1d, more preferably at most 0.05d. By way of example, where the inner recess 22 has a depth of 90 μm, the outer portions 23 have a height of 30 μm and the diameter d is 140 μm, the indentations 65 and surfaces 64 may have widths that are 5 μm. Similarly, in the construction of FIG. 19, the indentations 65 and surfaces 64 have widths that are 5 μm.

The depth of the indentations 65 is chosen to allow the channels to retain the polar medium. By way of example, in the construction of FIG. 19, the indentations 65 have a depth of 5 μm, providing an aspect ratio of 1:1.

However, deeper indentations 65 provide more effective capture and retention of polar medium. By way of example, in the construction of FIG. 25 and FIG. 21, the indentations 65 have a depth of 50 μm, providing an aspect ratio of 10:1. This captures and retains oil more effectively within the channels due to higher capillarity. The available droplet diameter d is 100 μm. An added benefit of the higher aspect wells is that they provide a smaller droplet diameter which in turn provides a smaller amphipathic membrane area.

The surfaces 66 of the pillars 23 between the indentations 67 lie in a common curved plane extending around the inner recess 22. The indentations 67 hold polar medium which repels the apolar medium. The pre-treatment of apolar medium 70 added to the partitions 6 is held within the indentations 65 by surface tension/capillarity which serves to increase the phobicity of the partitions 6 to the polar medium and thereby assists in the filling of the inner recess 22.

The indentations 67 and surfaces 66 have widths preferably of at most 20 μm, more preferably of at most 10 μm. The indentations 67 and surfaces 66 have widths that is small compared to the size of the volume of volume 2 of polar medium held in the inner recess 22. For example, if the dimensions of the inner recess 22 are characterised with reference to the diameter d of the largest notional sphere that can be accommodated within the inner recess 22, then the indentations 65 and surfaces 64 have widths that are preferably at most 0.1d, more preferably at most 0.05d. By way of example, where the inner recess 22 has a depth of 90 μm, the outer portions 23 have a height of 30 μm and the diameter d is 140 μm, the indentations 65 and surfaces 64 may have widths that are 5 μm. However, deeper indentations 67 provide more effective retention of polar medium, but it is difficult to provide higher aspect indentations 67 due to the limited space.

The following comments apply to the support 3 with any of the above-described constructions.

The support 3 may comprise any number of compartments 4. The support 3 may comprise, for example, number of compartments 4 in the range from 2 to $10^6$, but may typically be in the range from 100 to 100,000.

An individual compartment 4 has a notional cross-sectional area defined by the spacing between the partitions 6 and a notional volume defined by the height of the partitions 6. The notional volume is typically the same for all compartments 4 of the array.

As in the examples above, the compartments 4 may have irregularly shaped peripheries as viewed across the support 3. Irrespective of the shape of the compartments 4, in the case where a compartment contains a single volume of the polar medium, the dimensions of a compartment 4 may be characterised with reference to the largest notional sphere that can be accommodated within the compartment 4. That is approximately the size of the largest volume 2 of polar medium that could be accommodated in the case that the volumes 2 of polar medium are spherical (which is not essential). Indeed, in the case where the volumes of polar medium are liquid, they can deform depending upon the dimensions of the compartment and the surface properties of the support. Such a size may typically be between 50 μm and 500 μm, more typically between 70 μm and 200 μm The array will typically contain volumes 2 of polar medium of a substantially similar size.

The dimensions of the compartment 4 may be chosen depending upon the size of the volumes 2 of polar medium to be contained. The volumes 2 of polar medium typically have an average diameter in the range from 5 μm to 500 μm or an average volume in the range from 0.4 pL to 400 nL. The density of the compartments 4 in the support 3 is therefore dependent upon the size of the volumes 2 of polar medium and the particular arrangement of the partitions 6.

In the above examples, the partitions 6 have a regularly repeating pattern so that the compartments 4 have the same size and shape across the support 3 and are arranged in a regular array. This is not essential. The partitions 6 and compartments 4 may have alternatively have differing shapes and/or sizes across the support 3 and/or the compartments 4 may be arranged in an irregular array.

The nature of the polar medium of the volumes 2 of polar medium is as follows.

The polar medium may be a hydrophilic medium. The hydrophilic medium may for example comprise an aqueous medium.

In one example, the polar medium of the volumes 2 is an aqueous buffer solution. The buffer solution may comprise a supporting electrolyte.

Figure 27:
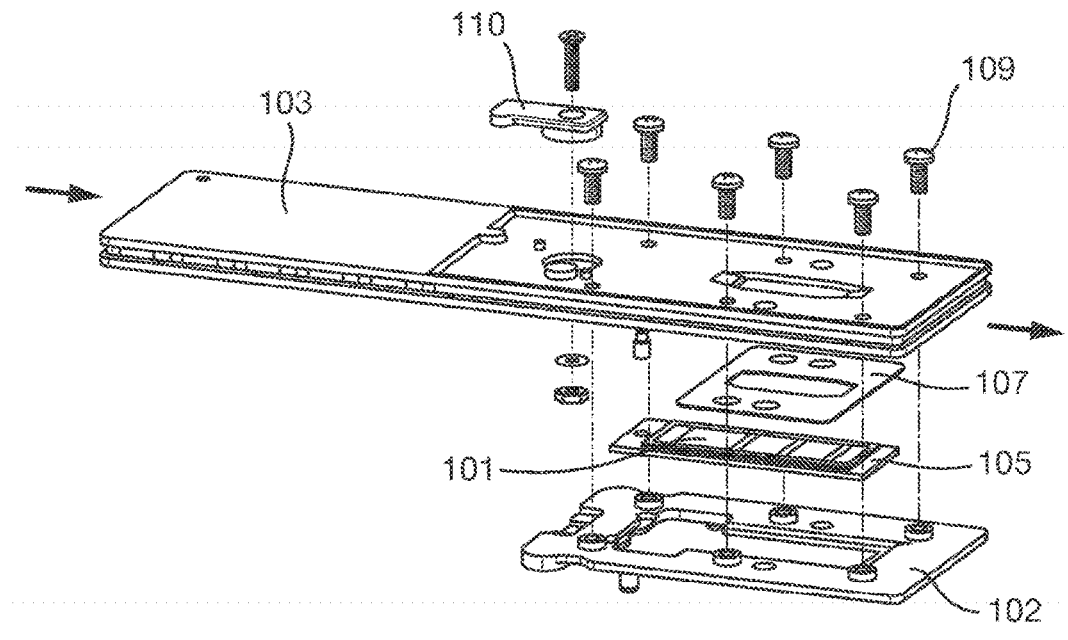
FIG. 27 is a diagram of a flow cell assembly incorporating an array.

The array may be filled with an emulsion or filled with volumes of apolar and polar volumes by use of a flow-cell assembly such as shown in FIG. 27. In FIG. 27, an array 101 attached to an ASIC/PCB 105 is inserted into the array retainer 102. A protective gasket 107 is placed on the surface of the array and the array is affixed to the fluidic module 103 using screws 109. Fluid may be flowed over the surface of the array in order to fill the compartments. Valve rotor 110 may be rotated in order to fluidically seal the flow cell. Fluid enters the flow-cell from a fluid reservoir (not shown) and exits the flow cell, as shown by the arrows.

Figure 28:
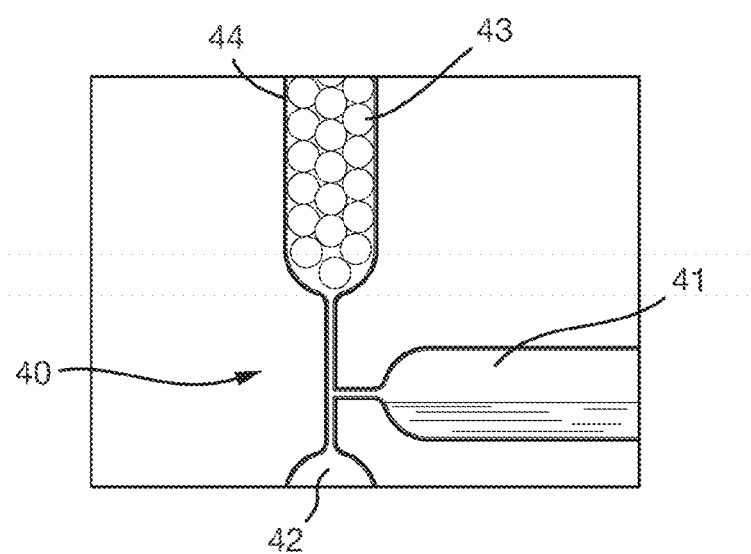
FIG. 28 is an image of droplets of aqueous solution made by a microfluidic flow junction.

In an example where the volumes 2 are pre-formed before being disposed in the compartments, the volumes 2 may be droplets of an aqueous buffer solution. In that case, they may be made in conventional manner, for example using a microfluidic flow T-junction 40 as shown in FIG. 28 comprising a first flow channel 41 containing the polar medium and a second flow channel 42 comprising the apolar medium. The two flow channels 41 and 42 intersect at the T-junction spontaneously forming droplets 43 which flow downstream from the T-junction and may be collected in a vessel 44 as an emulsion of the droplets 43 in the apolar medium. The size of the droplets 43 is determined by the flow rates of the polar and apolar fluids as well as the width of the apertures of the respective flow channels 41 and 42. FIG. 28 also shows droplets 43 that have been formed by the T-junction 40.

Droplets may be provided having different amounts of substances, by for example providing a third flow channel containing a different polar medium to the first flow channel which intersects with the first channel to form a common flow channel prior to intersecting at the T-junction. The flow rates of the third and first flow channels may be varied to provide droplets having varying ratios of components.

Figure 29:
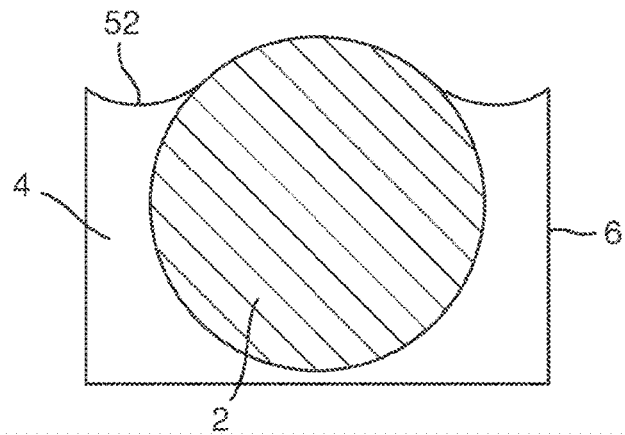
FIG. 29 is a schematic cross-sectional view of an apparatus containing a bead protruding out of a compartment.

In another example where the volumes 2 are pre-formed before being disposed in the compartments, the volumes 2 of polar medium may be beads of an aqueous gel, such as an agarose gel. The gel may comprise an aqueous buffer solution as the liquid phase. The buffer solution may comprise a supporting electrolyte. Examples of such are non-crosslinked or crosslinked hydrogels such as agarose or sepharose. A bead may be formed in-situ from a droplet for example by cooling or crosslinking with UV. A bead introduced into the apolar medium may form a droplet, for example by melting. The volume of polar medium may be provided within a porous plastic or glass bead.

Where the volumes 2 of polar medium are beads of an aqueous gel, they may have sufficient rigidity to protrude out of the compartments. FIG. 29 shows an apparatus that is an example of this. In this example, the bead protrude above the height of the partitions 6 and the meniscus 52 is formed as shown.

It may be the case that, when the volumes 2 of polar medium are beads of an aqueous gel, the leakage currents between the compartments 4 is reduced. Gel beads can be made in a conventional manner in T-piece droplet maker by merging a stream liquid gel at an elevated temperature into a stream of the apolar medium and allowing to cool, thereby to form an emulsion of beads of gel in the apolar medium. Gel beads may also be easier to locate onto a spiked electrode in the well and are generally more dimensionally stable.

In the case of using gels, shapes other than spherical may be created, for example elongate cigar shaped structures which might be employed in deep recesses (thus maximising the internal volume of the volume 2 of polar medium). This would have the advantage of extending the lifetime of the volume 2 of polar medium for example if the redox mediator were contained within the volume 2 of polar medium.

The aqueous gel may be a cross-linked gel. These are gels in which the matrix is cross-linked, which increases the hardness of the gel, providing a higher structural integrity than gels that are not cross-linked. For example, agarose gels may be cross-linked. Beads of cross-linked gel are commercially available and may be mixed with apolar medium to form an emulsion of beads of gel in the apolar medium. One possibility is cross-linked agarose beads with a particle size of 160 μm and an agarose content of 6.8-7.2% (as available for example from WorkBeads™200 SEC, BioWorks), which are highly porous and physically stable. The beads may be supplied from the manufacturer and may be coated with an amphipathic layer by introducing the beads into an apolar medium containing amphipathic molecules. This also permits an easier method of manufacture of such volumes 2 of polar medium.

Cross-linked gels may also provide advantages in inserting volumes 2 of polar medium into compartments 4 during manufacture the apparatus 1 as described below.

Figure 30:
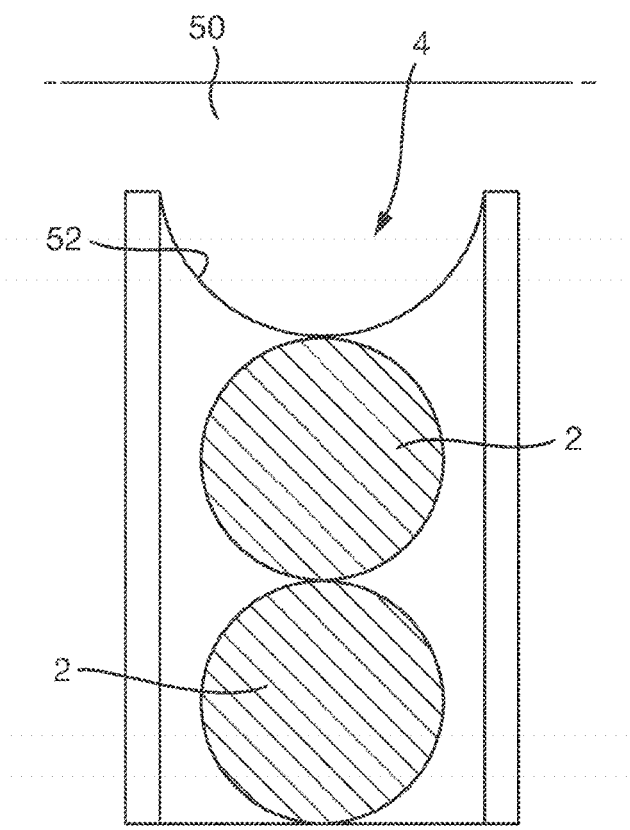
FIG. 30 is a schematic cross-sectional view of an apparatus containing plural volumes of hydrophilic medium.

Although in the above examples, a single volume 2 of polar medium is contained in an individual compartment, as an alternative plural volumes 2 of polar medium may be contained in a compartment 4. As an example of this, FIG. 30 shows an apparatus 1 in which two volumes 2 of polar medium are provided within a single compartment 4. The volumes 2 of polar medium are positioned on top of each other and may have a further layer 50 comprising polar medium provided in contact with one of the volumes 2 of polar medium. An membrane comprising amphipathic molecules may be provided at any interface between volumes 2 of polar medium, as well as at the interface between one of the volumes 2 of polar medium and the layer 50 of polar medium. Ion channels may also be provided in any such membranes. Provision of plural volumes 2 of polar medium in a compartment 4, for example as shown in FIG. 30, may increase the effective amount of the polar medium relative to the volume of the compartment 4. This provides advantages such as enabling a larger amount of mediator to be provided.

The nature of the apolar medium is as follows.

The apolar medium may be a hydrophobic medium.

The apolar medium may comprise a hydrocarbon or an oil or a mixture thereof. Suitable oils include silicone oil, AR20 or hexadecane. The apolar medium may be substantially immiscible with the polar medium of the volumes 2.

The apparatus 1 holding the array of volumes 2 of polar medium in a support 3, as described above, may have a wide range of biological, pharmaceutical and other analytical applications. It provides the opportunity to facilitate high throughput processing of small volumes 2 or groups of volumes 2 and may be used for example to compartmentalise reactions, cell sorting and screening applications such as protein crystallisation, analysis of blood or spinal fluid and waste processing. The ability to address and replace the volumes 2 of polar medium in the array is an important aspect, for example for carrying out reactions on the volumes 2 and replenishing the array.

Figure 31:
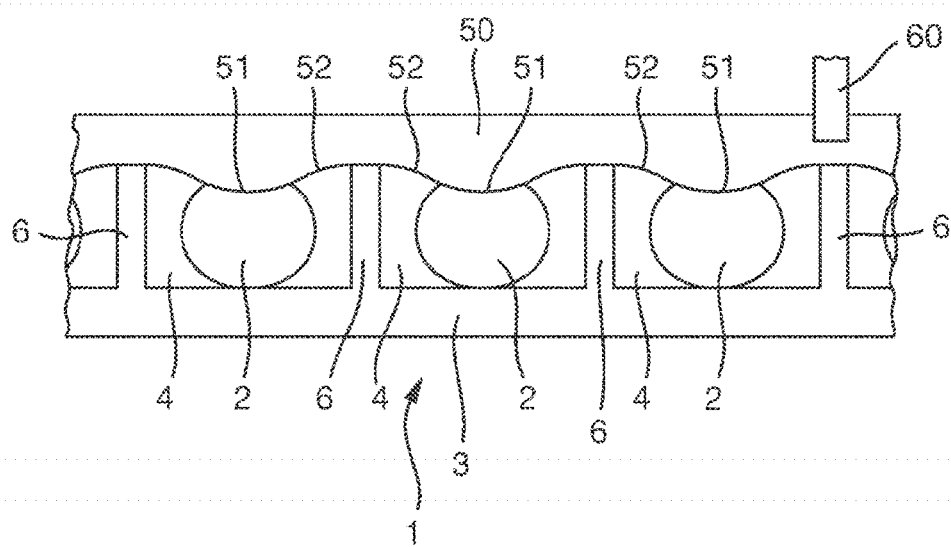
FIG. 31 is a cross-sectional view of part of the apparatus provided with a layer of polar medium.
Figure 32A:
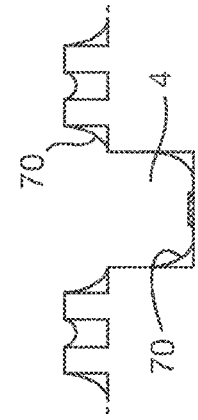
FIG. 32 is a set of schematic side views of a compartment in successive steps of a method.
Figure 32B:
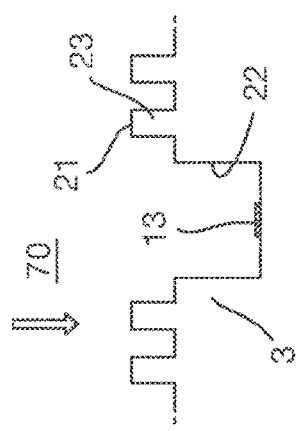
Figure 32C:
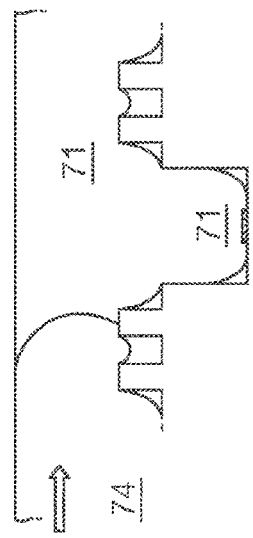
Figure 32D:
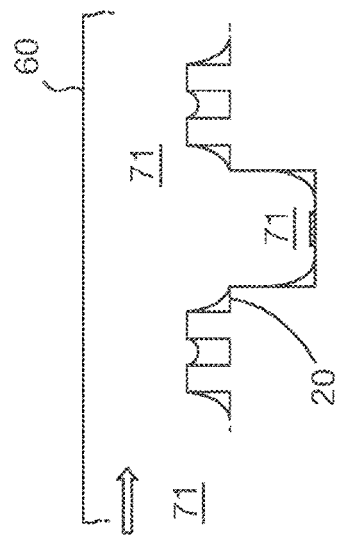
Figure 32E:
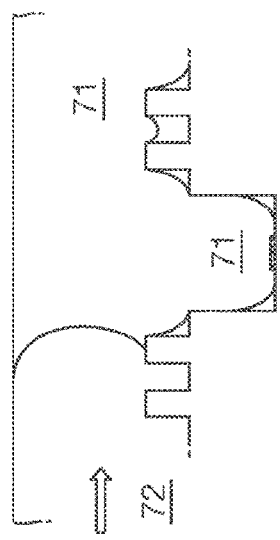
Figure 32F:
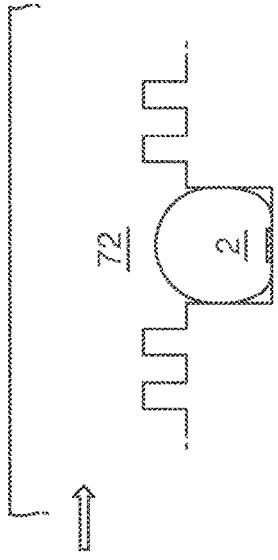
Figure 32G:
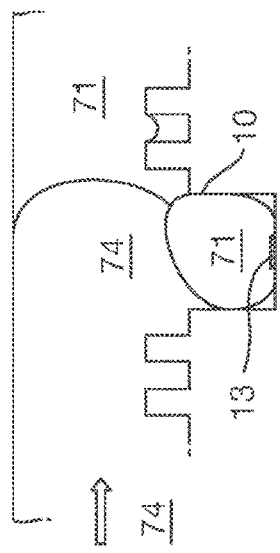
Figure 32H:
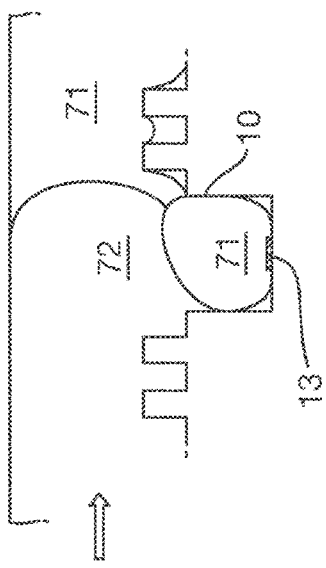
Figure 33A:
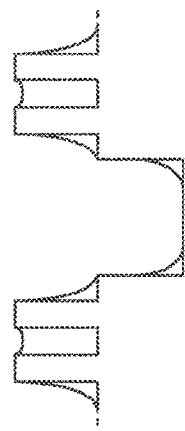
FIG. 33 is a set of schematic side views of a compartment in successive steps of a method.
Figure 33B:
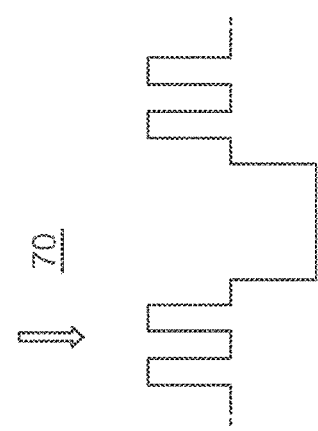
Figure 33C:
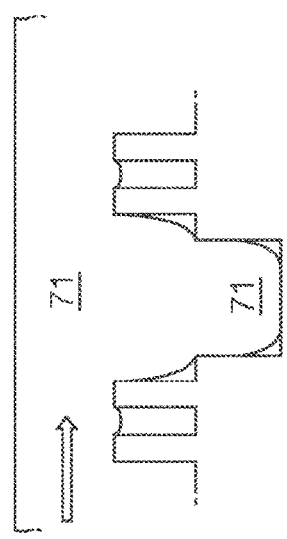
Figure 33D:
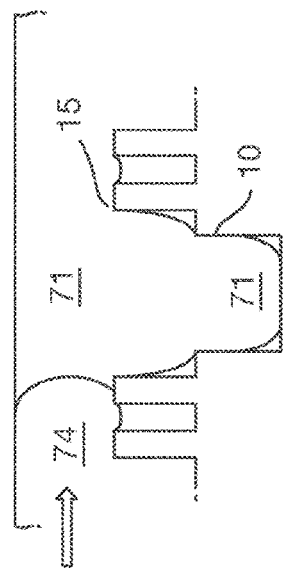
Figure 33F:
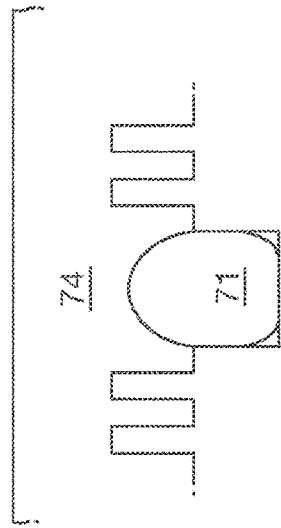
Figure 33H:
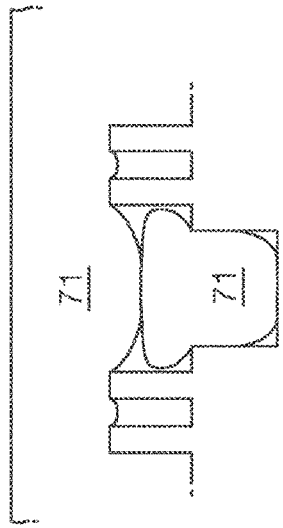
Figure 33E:
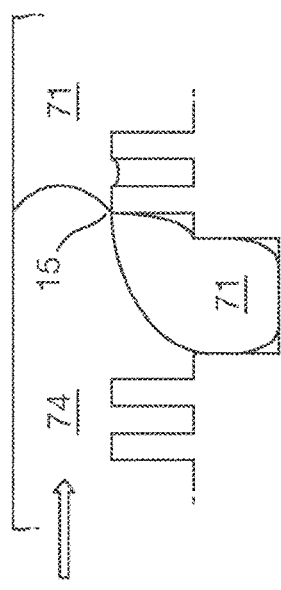
Figure 33G:
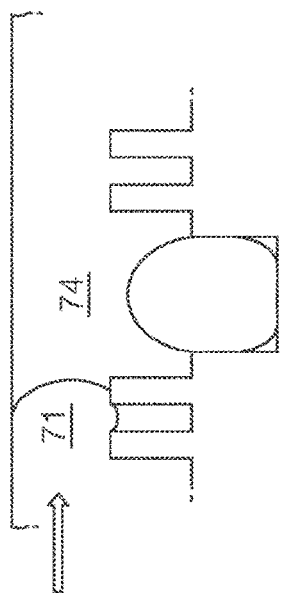

In some applications, the apparatus 1 holding the array of volumes 2 of polar medium in a support 3, as described above, may be provided with a layer 50 of a polar medium as shown in FIG. 31 (which illustrates by way of example the case that the volumes 2 of polar medium are droplets in an apolar medium). The layer 50 of a polar medium extends across the support 3 over the openings of the compartments 4. Thus the layer 50 of a polar medium rests on the partitions 6. The layer 50 of a polar medium is also in contact with at least some of the volumes 2 of polar medium preferably all of them. Membranes comprising amphipathic molecules are formed at the interfaces 51 between the layer 50 of polar medium and the volumes 2 of polar medium.

In order to form the membranes comprising amphipathic molecules, the amphipathic molecules may initially be provided in any one of more of the volumes 2 of polar medium, the layer of apolar medium or the layer 50 of a polar medium. In any of these cases, the membranes may form when the layer 50 of polar medium is flowed across the support 3. In the case of the amphipathic molecules being provided in the volumes 2 of polar medium, the volumes 2 of polar medium disposed within the compartments 4 may comprise a layer of amphipathic molecules around the surfaces thereof prior to provision of the layer 50 of a polar medium. In the case of the amphipathic molecules being provided in the layer 50 of a polar medium, the layer 50 of a polar medium may comprise a layer of amphipathic molecules on the surface that is brought into contact with the volumes 2 of polar medium.

The membranes comprising amphipathic molecules form at the at the interfaces 51 when the layer 50 of polar medium and the volumes 2 of polar medium are brought into contact. The membranes comprising amphipathic molecules separate the layer 50 of polar medium and the volumes 2 of polar medium.

The polar medium of the layer 50 may be the same or different material as the volumes 2 of polar medium. The polar medium of the layer 50 may be a hydrophilic medium. The hydrophilic medium may for example comprise an aqueous medium. In one example, the hydrophilic medium of the layer 50 comprises an aqueous buffer solution. The buffer solution may comprise a supporting electrolyte.

The nature of the amphipathic molecules is as follows.

The amphipathic molecules may be of any type that is capable of forming a membrane at the interfaces 51 between the layer 50 of polar medium and the volumes 2 of polar medium.

The method and apparatus of the invention is suitable for use with numerous different types of amphipathic molecules.

In one example, the amphipathic molecules may comprise a lipid, which may have a single component or a mixture of components, as is conventional when forming lipid bilayers.

Any lipids that form a lipid bilayer may be used. The lipids are chosen such that a lipid bilayer having the required properties, such as surface charge, ability to support membrane proteins, packing density or mechanical properties, is formed. The lipids can comprise one or more different lipids. For instance, the lipids can contain up to 100 lipids. The lipids preferably contain 1 to 10 lipids. The lipids may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-snGlycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. Examples of suitable lipids include without limitation phytanoyl lipids such as 1,2-diphytanoyl-sn-glycero-3-phosphocholine (DPhPC) and 1,2-diphytanoyl-sn-glycero-3-phosphoethanolamine (DPhPE). However such naturally occurring lipids are prone to biological degradation for example by proteins or detergents and are not able to withstand high voltages. Preferably the amphipathic layer is non-naturally occurring. Amphipathic polymer membranes are preferred over lipid membranes due to their ability to withstand higher voltages.

In another example, the amphipathic molecules may comprise an amphipathic compound comprising a first outer hydrophilic group, a hydrophobic core group, and a second outer hydrophilic group, wherein each of the first and second outer hydrophilic groups is linked to the hydrophobic core group.

Some such amphipathic compounds are disclosed in the International Patent Application filed on the same day as this application entitled "Droplet Interfaces" [ONT Ref: ONT IP 039] which is incorporated herein by reference.

Other such amphipathic compounds are disclosed in U.S. Pat. No. 6,916,488 which is incorporated herein by reference and discloses a number of polymeric materials that can be employed in the apparatus 1 as planar amphipathic membranes. In particular triblock copolymers are disclosed, for example silicon triblock copolymer membranes such as poly(2-methyloxazoline)-block-poly(dimethylsiloxane)-block-poly(2-methyloxazoline) (PMOXA-PDMS-PMOXA).

The use of such triblock copolymers as amphipathic membranes in the present invention is particularly preferred due to their ability to withstand high voltages, their robustness as well as their ability to withstand biological degradation from detergents and proteins. Their ability to withstand biological degradation allows the direct application and measurement of biological samples to the array, such as for example blood or serum. The polar layer applied to the top surface may be the sample to be determined. Examples of silicone triblock polymers that may be employed are 7-22-7 PMOXA-PDMS-PMOXA, 6-45-6 PMOXA-PE-PMOXA and 6-30-6 PMOXA-PDMS-PMOXA, where the nomenclature refers to the number of subunits. For example, 6-30-6 PMOXA-PDMS-PMOXA is comprised of 30 PDMS monomer units and 6 PMOXA monomer units.

Depending on the nature of the amphipathic molecules, the membranes may be bilayers of the amphipathic molecules or may be monolayers of the amphipathic molecules.

Some possible methods of forming an array of volumes 2 in the apparatus 1 are as follows.

First, there is provided the apparatus 1 comprising the support 3 arranged as described above.

In a first type of method, the volumes 2 of polar medium are pre-formed in the apolar medium before disposition in the compartments. There will now be described an example of this type of method in which first an emulsion of the volumes 2 of a polar medium in an apolar medium is made using the methods mentioned above.

The amphipathic molecules may be provided to the volumes 2 of a polar medium or the apolar medium. This may be achieved simply by adding the amphipathic molecules to the emulsion and whereupon they migrate to the interfaces between the volumes 2 of a polar medium and the apolar medium. Alternatively the amphipathic molecules may be added to the apolar medium prior to forming the emulsion.

To dispose the polar medium and apolar medium on the support 3, the emulsion is flowed over the support 3. This has the effect that the apolar medium flows into the compartments 4 and respective volumes 2 of polar medium within the apolar medium further flow into at least some of the compartments 4 through the openings. This has been found to occur naturally as the emulsion flows over the upper surface of the support 3, assisted by the design of the support 3 as describe above. The apolar medium and volumes 2 of polar medium are drawn into the array by capillary forces. In addition in supports 2 having gaps between compartments 4, the apolar medium flows between compartments through the gaps.

The emulsion typically contains more volumes 2 of polar medium than the number of compartments to ensure that a relatively large proportion of the compartments 4 are populated with volumes 2 of polar medium. The excess volumes 2 of a polar medium may be removed by washing the support 3 with the apolar medium. The washing leaves volumes 2 of polar medium in the compartments and leaves a layer of the apolar medium used for washing as a layer of apolar medium extending across the openings in contact with the volumes 2 of polar medium.

In this method, the emulsion may further comprise the amphipathic molecules. This facilitates the formation of the membranes when polar medium is flowed across the openings in the support to form a layer comprising polar medium, as described below. The presence of the amphipathic molecules also stabilises the emulsion.

The relative viscosities of the polar medium of the volumes 2 and apolar medium may be selected to be sufficiently similar that volumes 2 of a polar medium does flowing the emulsion over the support 3 do not float at the surface of the apolar medium away from the support 3. It is noted however that typically the volumes 2 of polar medium are drawn and held within the compartments 4 by capillary forces such that even if an apolar medium of a higher density than the volumes 2 of polar medium is used, the volumes 2 of a polar medium tend to remain within the apolar medium at the electrode surface.

This method also intrinsically provides a layer comprising apolar medium that extends across the openings of the compartments 4 in contact with the volumes 2 of polar medium in the compartments 4, being the apolar medium of the emulsion, or the apolar medium used to wash the support 3.

A dye may be incorporated into the volumes 2 of polar medium such that the presence of droplets in the array may be more easily visualised. A coloured dye, preferably of a different colour to that added to the volumes 2 of polar medium may be added to the apolar medium to more easily visualise the distribution of the apolar medium across the support 3. The incorporation of dyes within the volumes 2 of polar medium and/or apolar medium may be employed as a quality control check during fabrication to ensure that the compartments 4 are sufficiently populated with volumes 2 of polar medium and/or the apolar medium is properly distributed.

When the volumes 2 of polar medium are beads of an aqueous cross-linked gel, the emulsion may be flowed over the support 3 under positive pressure. This is possible because the cross-linked gels are harder and able to withstand the pressure, which is chosen having regard to the mechanical properties of the cross-linked gel. In contrast, beads of gel and droplets of solution can have a greater tendency to deform and merge under pressure. The use of such a positive pressure assists in filling of the compartments 4. This is particular advantageous when using a support with the first alternative construction or other constructions without gaps between the compartments, which are in general terms harder to fill.

In another example of the first type of method in which the volumes 2 of polar medium are pre-formed in the apolar medium, the volumes comprising polar medium may be dispensed directly into individual compartments, for example by acoustic droplet injection. With this technique, the dispensing may be controlled such that the correct number of volumes comprising the polar medium are dispensed without the need to remove excess volumes. In one embodiment of this technique, the substrate 3 comprises compartments 4 without gaps in the partitions, in which case it is desirable that the width of the volumes 2 of polar medium is less than the width of the opening of the compartment 4. The volume 2 may consist of a polar medium or comprise a polar medium within an apolar medium. In another embodiment, the substrate 3 comprises compartments 4 having gaps 8 in the partitions 6, wherein the gaps 8 extend fully from the openings to the base 5 of the support 3. In a yet further embodiment, the substrate 3 comprises compartments 4 having gaps 8 in the partitions 6, wherein the gaps may extend partially from the openings to the base 5. In the case that the gaps extend fully from the openings to the base of the support, a pretreatment may be advantageously added to the support prior to the addition of the volumes in order to constrain the droplets and prevent them from merging.

In a second type of method, the volumes 2 of polar medium are formed in the compartments 4 from a larger amount of polar medium that is flowed into the cell. Examples of such methods will now be described with reference to the schematic flow diagrams of FIGS. 32 to 34 which show the support 3 in successive steps of the method. In FIG. 32, the support 3 is of the type described above in which the partitions 6 comprise inner portions 20 defining inner recesses 21 without gaps, and outer portions 21 with gaps 23 In FIG. 32, the support 3 is illustrated schematically, and could for example be any of the second to eleventh alterative constructions described above.

First the support 3 is provided as shown in FIG. 32(*a*).

The support 3 is pre-treated with a pre-treatment apolar medium 70 as shown in FIG. 32(*b*). The pre-treatment apolar medium 70 may be of the same or different material from the layer of apolar medium subsequently applied as described below.

The pre-treatment apolar medium 70 (which may be diluted in a solvent) is added to the substrate 3 (for example by pipette) and allowed to spread across the substrate by capillarity. The pre-treatment apolar medium 70 collects inside the corners of the inner recess 22 and around the pillars 23 of the outer portions 21, in particular in the corners between the pillars 23 and the upper surface of the inner portion 20.

Next, polar medium 71 and apolar medium 74 are disposed on the support 3 as follows.

Polar medium 71 is flowed across the support 3 so that the polar medium 71 enters into the compartments 4 through the openings, as shown in FIG. 32(*c*). One way of doing this is to attach one end of the apparatus 1 to a flow cell 60. At least a portion of the are of the electrode 13 is free from apolar medium and therefore the volume 2 of polar medium makes electrical contact with the electrode 13.

In contrast to the first type of method wherein the volumes 2 of polar medium and the apolar medium are disposed on the support 3 together, for example in an emulsion, herein the layer of apolar medium is provided subsequently.

Excess polar medium 71 is removed by flowing a displacement fluid having a different phase from the polar medium across the substrate 3, leaving the volumes 2 comprising polar medium in the compartments 4. Two alternative approaches for this are described.

The first approach is illustrated in FIGS. 32(*d*) and (*e*). In the first approach, the displacement fluid is apolar medium 74 which is flowed across the substrate 3 as shown in FIG. 32(*d*). Clipping of the polar medium 71 takes place at the outer edge of the inner portion, as shown in FIG. 32(*e*). Relaxation of the volume of polar medium takes place as shown by FIG. 32(*j*) to leave the volumes 2 comprising polar medium in the compartments 4. This first approach leaves a layer 73 comprising apolar medium extending across the openings of the compartments 4 in contact with the volumes 2 comprising polar medium.

The second approach is illustrated in FIGS. 32(*f*) to (*i*) which steps occur instead of FIGS. 32(*d*) and (*e*). In the second approach, the displacement fluid is a gas 72 which is flowed across the substrate 3 as shown in FIG. 32(*f*). Clipping of the polar medium 71 takes place at the outer edge of the inner portion, as shown in FIG. 32(*g*), leaving the volumes 2 comprising polar medium in the compartments 4 and a layer of the gas 72 extending across the openings of the compartments 4 in contact with the volumes 2 comprising polar medium, as shown in FIG. 32(*h*). The gas 72 is preferably inert, and may be air or any other gas.

Thereafter, apolar medium 74 is flowed across the substrate 3, as shown in FIG. 32(*i*), displacing the gas 72 to provide a layer 73 comprising apolar medium extending across the openings of the compartments 4 in contact with the volumes 2 comprising polar medium, as shown in FIG. 32(*j*). As an alternative to being flowed, the layer 73 of apolar medium 74 could be provided across the substrate 3 using some other technique such as spraying.

In each of the first and second approaches, the displacement fluid flows across the support 3, through the gaps in the outer portions 23 and therefore scrapes across the openings of the compartments 4 to displace or clip the excess polar medium. Thus, the geometry and physical properties of the outer portions 23 and the inner recesses 22, including the effect of the indentations 65 when present, control the process of disposing the volumes 2 of polar medium in the inner recesses 22. The effectiveness of clipping and the ultimate shape of the volume 2 of polar medium is determined by a number of factors such as the relative heights of the outer portions 23 and inner recesses 20, the aspect ratio of the inner recesses 20. The dimensions of the inner recesses 22 and the outer portions 23 of the partitions 6 are ideally selected so that the volumes 2 comprising polar medium form a meniscus across the inner recess 22 as shown in FIGS. 32(*h*) and (*j*).

By way of a counter-example, FIG. 33(*a*) shows steps of a method corresponding to that of FIG. 32, except that the support 3 having a larger ratio of pillar height to depth of the inner recess compared to that of FIG. 32. Due to the increased pillar height, clipping of the polar medium by the displacing fluid 74 takes place at the outer edge 15 of the pillar as opposed to the outer edge 10 of the inner recess as shown in FIG. 33(*e*). This results in a larger volume of polar medium being retained in the compartment 4 as shown by FIG. 33(*f*). Due to the increased volume of the polar medium in the compartment a larger interface is formed following flowing of the polar medium over the support, as shown in FIG. 33(*h*). In general the smaller the membrane interface, the lower the noise and electrical resistance. Thus the membrane interface as shown in the method of FIG. 32 is preferred to the membrane interface as shown in the method of FIG. 33.

As regards specific dimensions of the geometry, it should be noted that the optimum dimensions are very much dependent upon the material system, including respective surface energies of the material of the substrate 3, the apolar medium and the polar medium. Also because filling is a dynamic process, it also depends to some extent upon the flow rate across the substrate 3. Thus the preferred dimensions dependent on the material system. Any reference to particular dimensions herein hold for a material system where the substrate 3 is the epoxy resin TMMS, the apolar medium is silicone oil AR20 and the polar medium is 1M KCl.

As an alternative to flowing polar medium 71 across the support into the compartments 4 and then removing the excess polar medium by flowing a displacement fluid, the volumes 2 could be disposed on the support by injecting discrete volumes 2 of polar medium into the compartments 4 through air, for example using a printing technique. In that case the apolar medium 74 is then subsequently disposed on the support.

The pre-treatment apolar medium 70 also has a beneficial role in the formation of volumes 2 of polar medium.

Firstly, in the case of compartments 4 having gaps therebetween, the pre-treatment apolar medium 70 sits in the gaps and seals them against flow of the polar medium. This assists in forming discrete volumes of polar medium by reducing the tendency of the volumes in neighbouring compartments to contact and merge.

Secondly, the pre-treatment apolar medium 70 may also serve to coat the support 3 and may modify the surface properties in a beneficial way. Depending on the surface properties of the support 3 and the properties of the pre-treatment apolar medium 70, the addition of pre-treatment apolar medium 70 may change the contact angle between the support 3 and a volume of polar medium disposed within a compartment. The pre-treatment apolar medium 70 may be used for example to increase the phobicity of the support 3 to the polar medium and provide a volume having a more convex shape. The use of a pretreatment to alter the phobicity of the support 3 to a desired level permits the use of a wider number of materials to be considered in making the support 3. This can be useful for example in the case where a particular material is desirable from a manufacturing point of view but does not have appropriate material properties.

Figure 34A:
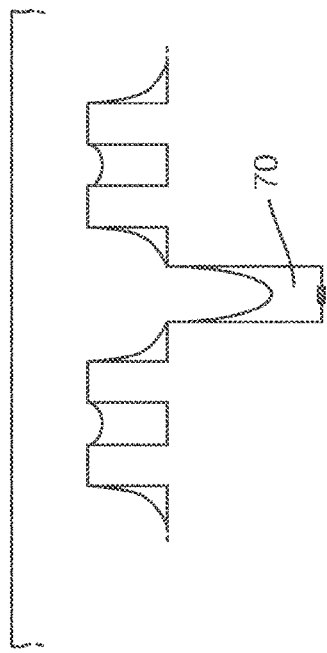
FIG. 34 is a schematic side view of a compartment having a pre-treatment apolar medium applied.
Figure 34B:
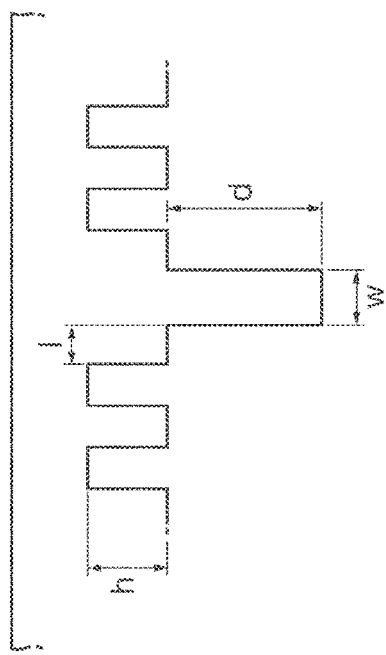

The aspect ratio of the inner recesses 22 is an important consideration. Aspect ratios (length:width) that are too large can result in a meniscus of the pre-treatment apolar medium 70 forming which spans the electrode 13 as illustrated in FIG. 34(*b*). If the aspect ratio (depth d:width w) is too small, clipping can result in the removal of polar medium from the compartment. Desirably, the inner recesses 22 have a ratio of depth to width, where the width of an inner recesses is defined as the diameter of the largest notional sphere that can be accommodated within the inner recess 22, that is at least 1:3, preferably at least 2:3. Desirably, the inner recesses 22 have a ratio of depth to width, where the width of an inner recesses is defined as the diameter of the largest notional sphere that can be accommodated within the inner recess, that is at most 3:1, preferably at most 3:2.

The effectiveness of clipping and the ultimate shape of the volume of polar medium is determined by a number of factors such as the relative values of height (h) of the outer portions, the depth (d) of the inner recess, the width (w) of the inner recess and the length (l) between a respective outer portion and an inner recess of a compartment, as shown in 34(*a*). The optimum dimensions for forming the array also depend upon factors such as the relative surface energies of the material of the support, the apolar medium and the polar medium. The process for forming an array also depends upon the flow rate of the apolar and polar media across the support.

A computer simulation of the second approach will now be described.

Figure 35:
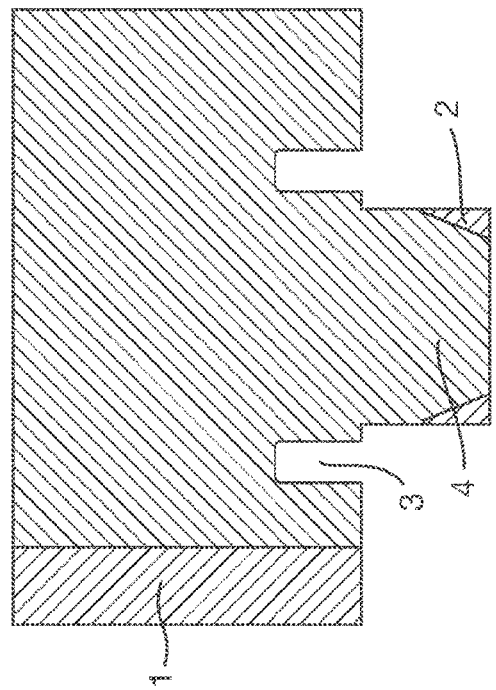
FIG. 35 is a side view of a compartment at the start point of a computer simulation.

FIG. 35 shows the start point of the computer simulation, where the substrate 3 has been pre-treated with a pre-treatment apolar medium 70, in this example oil, and then filled with a polar medium 71, in this example an aqueous buffer solution. FIG. 35 also shows the front of the apolar medium 74 in its start point before being flowed across the substrate 3.

FIGS. 36(A) and (B) show the computer simulation after the apolar medium 74 has flowed across the substrate 3, FIG. 36(A) showing the initial state and FIG. 36(B) showing the steady state after the system has been allowed to relax. FIG. 36(B) shows that the volume 2 of polar medium has pinned to the surfaces of the inner recess 22.

FIG. 36(C) shows a confocal image of a compartment 4 of the substrate containing a volume 2 of polar medium. As predicted by the computer simulation, the volume 2 of polar medium has pinned to the surfaces of the inner recess 22.

FIG. 37 shows a relaxation from the initial to steady state, similar to that of FIGS. 36(A) and (B), in simulations for inner recesses 22 having widths of 130 μm, 110 μm and 90 μm, all of which show pinning of the volume 2 of polar medium to the surfaces of the inner recess 22. These results also show that the meniscus of the volume 2 of polar medium, at its interface with the apolar medium, does not protrude above the edges of the inner recess 22, which helps to achieve membrane size control.

FIGS. 38(A) and (B) are images showing the formation of volumes 2 of polar medium, in this case aqueous buffer solution, in the construction of FIG. 21. Uniform volumes 2 of polar medium were observed, pinned to the surfaces of the inner recess 22.

FIGS. 39(A) and (B) are images showing the formation of volumes 2 of polar medium, in this case aqueous buffer solution, in the construction of FIG. 19. Uniform volumes 2 of polar medium were observed, pinned to the surfaces of the inner recess 22.

The pre-treatment apolar medium 70 may comprise the amphipathic molecules but this risks the amphipathic molecules providing an electrically insulating layer across the electrode 13, so it is preferred that the pre-treatment apolar medium 70 does not comprise the amphipathic molecules.

The layer 73 comprising apolar medium may comprise amphipathic molecules. The apolar medium 74 which is flowed across the substrate 3 may comprise the amphipathic molecules. Alternatively, the apolar medium 74 which is flowed across the substrate 3 may not comprise the amphipathic molecules so that the initially provided a layer 73 similarly does not comprise the amphipathic molecules, in which case the amphipathic molecules may be subsequently added to the layer 73 comprising apolar medium.

In any of those cases, after formation of the layer 73 comprising apolar medium, the apparatus 1 is left for a period of time that allows the amphipathic molecules to migrate to the interface between the layer 73 comprising apolar medium and the volumes 2 comprising polar medium. Typically the apparatus 1 may be incubated for a period of time of the order of 30 mins.

As another alternative, the amphipathic molecules may be provided in the polar medium 75 that is subsequently flowed across the support 3 as described below. A method of forming an array of membranes using the apparatus 1 is performed by forming an array of volumes 2 by the method described above, and then performing the following steps. These steps are illustrated in FIG. 32 for that method of forming an array of volumes 2 of polar medium but is generally applicable to any of the methods of forming an array of volumes 2 of polar medium described herein.

Polar medium 75 is flowed across the support 3 to cover the openings of the compartments, as shown in FIG. 32(*k*). The polar medium displaces the apolar medium of the layer 73 comprising apolar medium to form a layer 76 comprising polar medium extending across the openings in the support 3 as shown in FIG. 32(1). FIG. 40(C) shows a more detailed view. The layer 75 comprising polar medium is brought in contact with the volumes 2 comprising polar medium forming an interface 77 with each of the volumes 2 comprising polar medium.

In the case that the amphipathic molecules are already present, membranes 78 comprising amphipathic molecules are formed at the those interfaces 77. This occurs simply by flowing the polar medium 75 over the support 3.

Alternatively, the amphipathic molecules may be provided in the polar medium 75 that is subsequently flowed across the support 3. In that case, after formation of the layer 75 comprising polar medium, the apparatus 1 is left for a period of time that allows the amphipathic molecules to migrate to the interfaces 77 between the layer 75 comprising polar medium and the volumes 2 comprising polar medium, and thereby form the membranes 78. Typically the apparatus 1 may be incubated for a period of time of the order of 30 mins. FIG. 31 shows an equivalent example for the case that the volume 2 of polar medium is a droplet in the apolar medium introduced into the compartment 4 using an emulsion as described above, showing the layer 50 of polar medium that has been formed by flowing polar medium across the support 3 in the same way.

The geometry and physical properties of the outer portions 23, including the effect of the indentations 67 when present, control the geometry of the layer 75 comprising polar medium extending across the support 3. The dimensions of the inner recesses 22 and the outer portions 23 of the partitions 6 are selected having regard to the dimensions of the inner recesses 22 so that the volumes 2 comprising polar medium form a meniscus across the outer portions 23 as shown in FIG. 32(1). The meniscuses of the volumes 2 comprising polar medium and the layer 75 comprising polar medium extend towards each other to an extent that brings them into contact. Thus the geometry controls the formation of the membranes 78 providing reliability in that formation. This also allows control of the size and stability of the membranes 78 comprising amphipathic molecules.

The relative heights of the pillars to the inner recesses is therefore a design consideration. In the case of a particular material system where the substrate 2 is made of epoxy resin TMMS, the apolar medium is silicone oil AR20 and the polar medium is 1M KCl, when the height of the pillar was 60 μm and the height of the inner recess was 90 μm (1:1.5), clipping of the volume 2 of polar medium took place at the upper edge of the partition 6, which resulted in a volume 2 of polar medium which protruded from the inner recess. This resulted in a 'muffin' shaped droplet with a large membrane area (large interface). Whilst this membrane can work, it is not an ideal shape, as larger membranes are prone to more leaks, have a higher capacitance and are often electrically more noisy. In the case of the material system mentioned above, ratios of the height of the pillars to the inner recesses of 30:90 and 30:120 were shown to be effective.

By way of example, FIGS. 40(A) and 40(B) are images of a support 3 with the construction of FIG. 19 in which membranes have been formed in the case of the polar medium being an aqueous buffer solution.

The apparatus 1 may be kept in the state with or without the layer 75 of polar medium, in storage or during transport from a manufacturing facility to the point of use of the apparatus 1. The layer 50 of polar medium may be applied after such storage or transport, if not already present.

In the first type of method of forming the volumes 2 of polar medium wherein the volumes 2 of polar medium are pre-formed as droplets in an emulsion, in order for the droplets to be incorporated into the compartments 4, they need to be provided within a fairly narrow range of size distribution and therefore it is necessary for the emulsion to be stable. The formation of a stable emulsion may be achieved by the presence of amphiphilic molecules which form interfaces between the droplets and apolar medium. In the absence of amphiphilic molecules, the emulsion is unstable. This tends to result in some degree of merging of the droplets to form larger droplets which are unable to fit correctly within the compartments 4.

A potential drawback however with the method of providing a stable emulsion is that during the process of filling the compartments 4, the apolar medium tends to coat the surfaces of the electrodes 13 provided in each compartment 4 resulting in a layer between the electrode 13 and the volume 2 of polar medium that is an electrically resistive. Electrical contact between the electrode 13 and the volume 2 of polar medium may be necessary requirement if it is desired to sense electrical signals such as ion flow across a membrane. The presence of amphiphilic molecules in the layer across the electrode 13 further exacerbates the problem of poor electrical contact. Due to the presence of both apolar and polar groups, it is difficult to displace amphiphilic molecules from the surface of the electrode 13 by modifying its surface characteristics.

The second type of method may be applied to reduce the problem of poor electrical contact by assembling individual volumes 2 of polar medium in the compartments 4 in the absence of amphiphilic molecules. The apolar medium added to the substrate 3 is largely localised at the surface of the partitions 6 and away from the electrode 13. Thus, the pre-treatment apolar medium 70 may further comprises the amphipathic molecules, so that the membranes comprising amphipathic molecules are formed after the step of flowing polar medium 8 across the support 3 to displace apolar medium and form a layer of polar medium.

However, if the pre-treatment apolar medium 70 does not include amphipathic molecules, the volumes 2 of polar medium are assembled in the absence of the stabilising amphiphilic molecules, and so merging of volumes between neighbouring compartments is much more of an issue. As such, semi-closed structures are preferred (structures comprising partitions having no or few gaps provided on the surfaces of wells) due to the fact that the individual volumes are confined within the wells. However the method will also work to some extent with open structures (pillars having gaps that extend the height of the compartments) due to the fact that the pre-treatment apolar medium 70 can, depending upon the separation between the pillars, partially span the gaps between the partitions thus effectively providing a semi-closed structure.

The apparatus 1 may have membrane proteins inserted into the membranes comprising amphipathic molecules formed at the interfaces 51. The membrane proteins may be ion channels or pores.

Such membrane proteins that are capable of insertion into the membranes comprising amphipathic molecules may initially be provided in either or both of the layer 50 of polar medium and the volumes 2 of polar medium, prior to bringing the layer 50 of polar medium and the volumes 2 of polar medium into contact. In some material systems, bringing the layer 50 of polar medium and the volumes 2 of polar medium into contact to form the membranes comprising amphipathic molecules may cause the membrane proteins to spontaneously insert into the membranes. Insertion of the membrane proteins into the membrane can be assisted where necessary for example by means such as the application of a potential difference across the membrane 2.

Alternatively the membrane proteins may be provided in the apolar medium.

The membrane proteins may be used to perform analysis of a sample in the layer 50 of polar medium.

To facilitate this, the layer 50 of polar medium may comprise the sample to be analysed at the time it is initially added. As an alternative, the layer 50 of polar medium may be provided as described above without the sample to be analysed. This allows the apparatus to be prepared for storage and transportation prior to use. In that case, prior to performing the analysis, there may be carried out a step of displacing the layer 50 of polar medium by a further layer of polar medium that comprises the sample to be analysed.

Membrane proteins that are ion channels may be used to measure the translocation of an analyte through the ion channel by measurement of current flow under a potential difference applied across the ion channel. The membrane itself is highly resistive and has a resistance typically of the order of 1GΩ or greater. Thus ion flow takes places substantially exclusively through the ion channel. By way of example, FIG. 41 shows electrical data obtained for measurement of ion current flow through an MspA nanopore illustrating pore insertion.

The ion channel may be a nanopore for determining the sequence of a polynucleotide. The current may be measured wherein the magnitude and duration of each current episode may be used to determine the sequence. The array may comprise an enzyme for control of translocation of the polynucleotide through a nanopore.

The ion channel may be provided in the layer 50 of polar medium external to the volumes 2 of polar medium. It is possible that more than one ion channel may insert into the membrane or none at all. In practice there will be a Poisson distribution of ion channels in the membranes. Following insertion of the ion channels, the membranes may be measured, for example by measurement of ion flow through the channel, in order to determine which membranes contain a single ion channel. Droplets containing a single channel may be selected for further experimentation. The percentage of droplet interfaces containing single ion channels may be optimised by varying the concentration of ion channels in the polar medium.

Alternatively the ion channel may be provided in the apolar medium. Formation of an ion channel in a membrane may be checked optically by for example providing a fluorophore in the polar interior of the droplet and a quencher in the polar meniscus layer. If an ion channel is present in the membrane at the interface 51, the quencher and fluorophore will come within close proximity of one another, extinguishing the fluorescent signal.

The magnitude of ion flow is dependent upon the potential difference applied across the ion channel and therefore is it desirable to provide a stable reference potential. Both members of the redox couple are required in order to provide a stable reference potential. However, one member may be provided and the other member generated in situ, for example by oxidation or reduction of the redox member present.

Electrical measurements may be taken as follows.

The apparatus 1 further comprises a common electrode 60 arranged above the support 3 as shown in FIG. 31 so that the common electrode 60 makes electrical contact with the layer 50 of polar medium once it has been provided.

As shown in FIG. 42, the apparatus 1 further comprises an electrical circuit 61 connected between the common electrode 60 and the respective electrodes 13 in each compartment 4. The electrical circuit 13 is arranged to take the electrical measurements and may have a conventional construction, for example as discussed in more detail in WO-2009/077734 which is incorporated herein by reference.

The electrical circuit 61 is configured to take electrical measurements dependent on a process occurring at or through the membranes. Where a sample containing an analyte is provided, for example in the layer of a polar medium, the process may analyse the sample. The polar medium of the layer 50 applied to the support 3 may be for example the liquid sample to be analysed. This sample may be a biological sample such as blood, serum, urine, interstitial fluid, tears or sperm. The liquid sample may be derived from a solid or semi-solid sample. The sample may be agricultural, environmental or industrial in origin. It may be a forensic sample.

An electrochemical measurement apparatus typically comprises working, counter and reference electrodes wherein a potentiostat measures the potential difference between the working and reference electrodes and measures current flow between the working and counter electrodes. Because no current flow takes place through the reference electrode a constant potential difference is maintained between the reference electrode and working electrode. Alternatively, a two electrode system may be employed, as is the case with the apparatus 1, wherein a potential is provided between a counter and a counter/reference electrode and ion flow takes place between these electrodes. This however results in consumption of one or the other member of the redox couple depending upon the polarity of the potential applied. The rate of consumption of the redox member is dependent upon the magnitude of the ion flow.

In the case of measurement of the translocation of a polynucleotide, the polynucleotide is caused to translocate the pore under a positive potential applied across the pore. Application of a positive potential results in the oxidation of one member of the redox couple which ultimately will become depleted. Once depletion of a redox member occurs, the reference potential will start to drift, therefore limiting the lifetime of the measurement. In the case of one or both members of the redox couple provided within the droplet the lifetime of the measurement is dependent upon the amount of the reduced member of the redox couple, which in turn is dependent upon the concentration of the redox member and the droplet volume.

The apparatus 1 provides a stable array of volumes 2 of polar medium on which membranes may be formed in-situ. Such an array has advantages over an apparatus comprising an array of individual apertures across which suspended amphipathic membranes are provided. In the latter case, it is possible that leakage can occur at the membrane edges over time. By contrast volumes 2 of polar medium contained in an apolar medium are extremely stable. Amphipathic membranes formed from triblock copolymers are very stable and resistant to biological degradation. However it has proved very difficult to provide amphipathic membranes made from triblock copolymers, in particular silicon triblock copolymers, across an array of microwell apertures by methods such as described in WO2009/077734. By contrast it is relatively straightforward to prepare silicon triblock droplets. This enables nanopore arrays to be provided having very stable membranes and having a low susceptibility to biological attack. This also enables the direct application of samples such as biological samples to the amphipathic membrane.

The apparatus 1 would typically be single use. Thereafter the components of the apparatus 1, namely the biological sample, the volumes 2 of polar medium and apolar medium may be simply removed from the support 3, and the support 3 cleaned and repopulated with volumes 2 of polar medium and apolar medium. This allows reuse of the silicon chip and the electrode array comprising the array and the electrodes, which are expensive components of the array chip. It also allows for replenishment of the redox couple.

A particular application is wherein the apparatus 1 is housed in a single use handheld device for use with a computation means such as a laptop. Data is generated by the device and transmitted to the computation means by USB or other transmission means. The computation means would typically comprise a stored algorithm by which to generate event and base calling data.

Alternatively the apparatus 1 could be housed in a reusable device wherein the device comprises flow conduits allowing the array to be cleaned by flushing with solution stored in on-board fluid reservoirs.

Having regard to the electrical requirements, the electrodes 13 may be arranged as follows.

The electrodes 13 provide an electrical contact to the volumes 2 of polar medium and may be used to provide a potential difference across the membrane of amphipathic molecules. Electrical connections may extend from the electrodes 13 through the support 3 to an electrical circuit.

The electrodes 13 may be of any shape, for example circular. An individual electrode 13 may extend across the whole width of a compartment 4 or across a partial width thereof. In general, the electrodes 13 may protrude above the base 5 or may be integral with the base 5.

Some or all surfaces of the compartments 4 may be hydrophobic, including the outer surfaces of the partitions 6 inside the compartments 4. This assists positioning of a volume 2 of polar medium on an electrode 13 and thereby facilitates the making of an electrical contact.

The electrodes 13 may include other features to assist the making of an electrical contact to the volumes 2 of polar medium.

One option is for the exposed surfaces of the electrodes 13 may be roughened, for example by provision of a layer of Pt black on a Pt electrode.

Another option is for the electrodes 13 to comprise spikes 16 protruding into the compartment 4 to penetrate the volumes of polar medium. Following penetration of a volume 2 of polar medium by a spike 16 it tends to reform around the electrode effectively resealing the volume 2 of polar medium.

Exposed surfaces of the electrodes 13 may be hydrophilic and/or surfaces of the compartments 4 around the electrodes 13, for example the exposed surfaces of the surface coating 14, that may be hydrophobic. This can reduce the tendency of the apolar medium to coat the exposed surfaces of the electrodes and thereby act as an electrically insulating layer.

The electrode 13 may be a reference electrode such as Ag/AgCl in order to provide a stable reference potential with respect to a counter electrode. Alternatively the electrode 13 may be an electrochemically inert material such as Au, Pt, Pd or C and the electrode potential provided by one or both members of a redox couple located within the polar interior of the droplet. Types of redox couples that may be employed are for example Fe(II)/Fe(III), Ru (III)/Ru (II) and ferrocene/ferrocinium. Specific examples of redox couples that may be employed are ferri/ferrocyanide, ruthenium hexamine and ferrocene monocarboxylic acid.

FIG. 43 shows the droplet lifetime for various droplet diameters for ferro/ferricyanide as the redox couple. As can be seen from the graph, a 200 mM concentration of ferrocyanide in a 200 μm diameter droplet has a lifetime of approximately 140 hrs for a current flow of 100 pA.

The support 3 is designed as follows to assist the formation of membranes of amphipathic molecules.

As shown in FIG. 31, the layer 50 of polar medium forms a meniscus 57 that protrudes into the compartments 4 to contact the volumes 2 of polar medium. All the constructions of the support 3 described above provide the advantage that the upper surfaces of the partitions 6 assist in the formation and pinning of the meniscus 52. In particular, the various, convoluted shapes of the upper surface of the partitions 6 provides pinning points for the layer 50 of polar medium in order to form the meniscus 52.

A meniscus formed in a conventional square type of well structure is not pinned uniformly around the edges of the well. As such, stresses on the meniscus are created at the corners of the well. In order to optimise meniscus formation in a well type structures, it is beneficial to provide further features on the wells in order to pin the polar layer. All the constructions of the support 3 described above provide such features, being for example the convoluted shapes of the various pillars 7 and 23 and the undulating shape of the common body 31 around the recess 30. The meniscus 52 may be pinned around these undulations effectively creating a more distributed pinned meniscus 52 in the compartment 4.

In general terms, such pinning is achieved in the constructions of the support 3 described above because in each case the total length per compartment 4 of the edges of the outer ends of the partitions 6 in the common plane is greater than the largest circumference of the largest notional sphere that can be accommodated within the compartments 4.

The layer 50 of polar medium forms the meniscus 52 with the partitions 6 which extends into the compartment 4 and contacts the volume 2 of polar medium provided therein to form a membrane. The compartments 4 are designed with openings having dimensions selected so that the layer of a polar medium when applied will form a meniscus 52 extending into the compartment 4 to an extent that brings the layer 50 of polar medium into contact with at least some of the volumes 2 of polar medium.

The ability to form a membrane is dependent upon the height of the volume 2 of polar medium within the compartment 4 and the extent to which the meniscus 52 extends into the compartment 4. This in turn is dependent upon the surface interaction between the partitions 6, the polar medium and the apolar medium, as well as the dimensions and shape of the compartment 4 defined by the partitions 6. These parameters, and/or the sizes of the volumes 2 of polar medium, may be selected such that a polar medium applied to the top surface of the support 3 will spontaneously form membranes with the volumes 2 of polar medium.

This is illustrated schematically in FIGS. 44(a) to (c) for the case that the volumes 2 of polar medium are droplets in the apolar medium. FIG. 44(a) shows the case that there is no contact between the layer 50 of polar medium and the volume 2 of polar medium so that a membrane is not formed due the volume 2 of polar medium being too small and/or the meniscus 52 not extending sufficiently into the compartment 4.

FIG. 44(b) shows the case whereby the volume 2 of polar medium and the meniscus 52 just contact one another. However, the size of the membrane may be insufficient. Also the membrane formation may be sensitive to other parameters. The size of the volume 2 of polar medium is temperature dependent and a small drop in temperature can result in contraction of the volume 2 of polar medium leading to the non-formation of a membrane. Furthermore, whilst the volumes 2 of polar medium are designed to be substantially similar in size, a small variation in the droplet size may occur, resulting in unreliable membrane formation.

FIG. 44(c) shows the case where the volume 2 of polar medium is made larger and/or the meniscus 52 extends further into the compartment 4 such that a substantial droplet interface is formed. This reduces the chances that the membrane will not be formed as well as providing a large surface area for ion channel insertion.

FIGS. 45 and 46 are schematic cross-sectional views of the apparatus 1 of the type shown in FIGS. 15 to 18 wherein the partitions 6 comprise inner portions 20 and outer portions 21 that comprise pillars 23 having gaps 24 therebetween, for the case that the volumes 2 of polar medium are droplets in the apolar medium. FIGS. 45 and 46 show the influence of the height and density of the pillars 23 on the pinning of the meniscus 52.

In FIG. 45, the meniscus 52 is pinned at the edges of the inner portions 20 and not the pillars 23. Additional apolar medium is pinned at the interface between the pillar 23 and the edge of the recesses 22 of the inner portion 20. The pillars 23 therefore serve to control the distribution of apolar medium but do not influence the formation of the meniscus 52 which is controlled by the recesses 22.

In FIG. 46, the arrangement of the pillars 23 is such that the meniscus 52 is determined by the pillars 23 themselves and not the recesses 22 in the inner portions 20. In FIG. 46, two sets of pillars 23 are provided between neighbouring compartments 4 on the inner portions 23 of the partitions 4. Alternatively for example, a single pillar might be provided having a larger height than that shown in FIG. 1.

Whether the meniscus 52 forms according to that of FIG. 45 or 46 will depend upon the arrangement and relative dimensions of the pillars 23 of the outer portions 21 and the recesses 22 of the inner portions 20.

Compartments 4 with no gaps between the partitions 6 have the tendency to flood with apolar medium. This is disadvantageous as this prevents formation of the membrane interface between the two volumes 2 of the hydrophilic medium.

FIG. 47 shows a meniscus 52 formed by a polar liquid at the surface of the support 3. The size and degree of curvature of the meniscus 52 of the layer 50 of polar medium applied to the upper surface of the support 3 can be controlled across a wide range. The curvature of the meniscus 52 will be determined by the contact angle between the polar liquid and the partitions 6, which is a property of the material system of the polar medium, the apolar medium and the surface properties of the partitions 6. It will also be determined by the dimensions across the opening of the compartment 4 on which the meniscus 52 is formed and the height of the partitions 6.

For example, for a compartment 4 having a width b between the partitions 6, a height c and a contact angle θ between the surface of the pillar and the meniscus 52, a meniscus 52 will be formed above the base of the compartment when:

$$\frac{c}{b} \leq \frac{1 - \sin\theta}{2 - \cos\theta}$$

The distance h that the meniscus 52 extends into the compartment can be determined, and can be controlled in combination with the size of the volumes 2 of polar medium to control the size of the meniscus 52. Conceptually, assuming a perfectly spherical volume 2 of polar medium of diameter d, an interface will be formed between the meniscus 52 and the volume 2 of polar medium when the diameter d≥c−h. For a diameter d of 150 μm, Permex being the material of the partitions 6 and a the polar medium of the layer 50 being 1M HEPES, suitable values for b and c are b=150 μm, a=30 μm, c<170 μm.

For a pillar array, menisci 52 are formed on the partitions 6 in what is known as a superhydrophobic or Fakir state. The Fakir state occurs when:

$$\cos\theta < \left(-1 + 4\frac{c}{a}\phi_s\right)$$

where a is the pillar thickness and where $\Phi_s$ is a dimensionless term which is equal to the fraction of solid in contact with the liquid.

Although the above examples are given assuming a perfectly spherical volume 2 of polar medium for ease of understanding, this might not be the case. In the case of a gel, the volume 2 of polar medium may be designed to have other shapes. Furthermore, even if the shape prior to entering the compartment 4 is spherical in shape, it may deform to some extent depending upon the nature of interaction with the support 3 and/or surface of the electrode 13, thus changing the height of the volume 2 of polar medium after it is contained in the compartment 4. This factor also needs to be taken into account when assessing the height of the volume 2 of polar medium in order to be able to spontaneously form membranes.

The widths and heights of the compartments 4 may be selected as follows. To take account of the differing profiles of the compartments 4 across the support 3, for this purpose, the width of a compartment 4 is defined as the diameter of the largest notional sphere that can be accommodated within the compartment 4.

The width of the compartment 4 may be chosen to be a value less than 2 times the average diameter of the volumes of polar medium in order to avoid the possibility that more than one volume 2 of polar medium may be contained in a side by side relationship within a compartment 4 where desirable. Where the volume of polar medium is a liquid droplet, the compartment width may have a value less than 2 times, for example 1.75 times the width, to take account of the fact that the droplets may deform, thus reducing their average width.

For the case that the volumes 2 of polar medium are droplets in the apolar medium, the width of the compartment 4 may further be chosen to be a value greater than the average diameter of a volume 2 of polar medium such that it may freely insert into the compartment 4. For this purpose, the width will typically be at least 1.05 times the average diameter of the volumes 2 of polar medium. The width will typically be at most 1.5 times the average diameter of the volumes 2 of polar medium. Widths greater than this provide the possibility that the volume 2 of polar medium may move within the compartment 4. Ideally the volume 2 of polar medium is provided in a closely packed arrangement within the compartment 4.

The height of the compartment 4 is determined by the height of the partitions 6. The height of the compartment 4 is chosen depending upon the size of the volumes 2 of polar medium and the ability to form a membrane with a polar liquid. The pillar height is typically between 1.1 and 1.3× the height of the droplet in the droplet zone. The compartments 4 may have heights that are at least 1.1 times the average diameter of the volumes of polar medium. The compartments 4 may have heights that are at most 1.3 times the average diameter of the volumes of polar medium. In a particular embodiment where the volume of polar medium is a bead, it may extend beyond the height of the partitions.

Some examples of experiments performed using an apparatus 1 as described above will now be given. In various examples, the apparatus 1 was formed as an array chip.

The first example is as follows.

Droplets of polar medium in apolar medium may be prepared as follows. 2 mg/ml of 6-30-6 PMOXA-PDMS-PMOXA triblock copolymer was dissolved in AR20 silicon oil to provide the apolar medium. The polar medium consisting of 625 mM NaCl, 75 mM potassium ferrocyanide and 25 mM potassium ferricyanide in 100 mM HEPES. Droplets were prepared in a microfluidic T-junction (Chip type: Dolomite, part no. 3000158) having two intersecting channels of 300 μm width. The channels narrow towards the intersection to provide channel widths at the intersection of 105 μm. The polar and apolar solutions were flowed along the channels at respective solution flow rates of 3-4 ul/min and 15-17 ul/min to provide droplets having a droplet size of between 150-160 μm.

The flow rates can be varied to provide droplets of different dimensions.

A silicon wafer having an array of Pt connectors spaced apart by 200 μm by 225 μm was coated with a 2-3 μm layer of SU photoresist. Permex pillars were added to the base support by a standard photolithographic process wherein uncrosslinked Permex precursor is applied to the base and the precursor cross linked by exposure to UV light through a patterned mask. The uncrosslinked precursor was subsequently washed away to reveal the pillar structure. The resulting array was a 38×128 droplet zone with a pillar shape according to FIG. 2. The pillar height was 160 μm. Droplets of 145 μm in diameter were added to the array in the form of an AR20 oil/droplet emulsion as described above.

The emulsion was applied to the top surface of the array and oil and droplets were drawn into the array by capillary action. Excess droplets were removed by flowing AR20 silicon oil over the array. The droplets were held in the array by surface tension.

The array was placed into a flow cell and the polar medium containing an MspA protein nanopore was flowed over the surface of the array to provide ion channels in the droplet interfaces.

Droplet interfaces containing single MspA nanopores were selected for experimentation and measurement of DNA was carried out by measuring ion flow through the individual nanopores during translocation of DNA.

The second example is as follows.

Apparatuses were prepared according to the following general method.

Array chips were fabricated in clean-room facilities. A 6 in Si wafer with a 1 µm thermal oxide (SiMat) was used a base support. The wafer was initially treated with 200 W, O2 plasma in a plasma processor (Oxford Instruments), it then underwent a dehydration bake at 150° C. for 15 minutes in a hotplate (Electronic Micro Systems Ltd). The wafer was coated with a 1 µm layer of SU-8 2 photoresist (MicroChem Corp.) in a spin-coater (Electronic Micro Systems Ltd, 3000 rpm for 30 seconds), soft baked at 65° C. and 2 min at 95° C. in a hotplate, flood exposed (110 mJ/cm2) in a UV mask aligner (Quintel Corp.) and then post-exposure baked (PEB) for 1 min at 65° C. followed by 2 min at 95° C. in a hotplate. The wafer is then spin-coated with a 120 µm thick layer of SU-8 3050 (1250 rpm for 30 s) and soft baked for 5 min at 65° C. followed by 2.5 h at 95° C. in a level hot plate. After cooling, it is exposed (260 mJ/cm2) in the mask aligner using the photomask patterned with the microfluidic network. A PEB is then carried out: 2 min at 65° C. and 15 min at 95° C. The channel features are developed by immersion of the wafer in Microposit EC Solvent (Rhom Haas Electronic Materials), in an appropriately size beaker, and shaken for 10 min and finally rinsed. Once the channels have been formed, the wafer is treated with O2 plasma for 1 min at 200 W to promote adhesion of the top layer and the SU-8 resist.

The channels are sealed with a layer of 100 µm thick film laminate resist, SUEX (DJ DevCorp) using a Exclam-Plus laminator (GMP) with the top roller set at 45° C., with a pressure setting at 1 mm thickness and a speed of 50 cm/min. A post lamination bake of 3 min at 65° C. was then carried out. After cooling, the SUEX layer was exposed (1400 mJ/cm2) using the fluidic port mask. It should be noted that the protective polymer layer on the laminate is left on. The PEB is 3 min at 65° C. followed by 7 min at 95° C., again with the protective film on. The wafer is then developed using propylene glycol monomethyl ether acetate (Sigma-Aldrich) for 10 min and rinsed thoroughly with isopropanol, making sure the all residual developer is rinsed from the interior of the channels. The wafers are finally hard baked at 150° C. for 1 h and diced into individual array chips.

EXAMPLE 1

This example describes the method used to produce the triblock co-polymer droplets which were used to fill the interconnecting droplet zones on the array.
Materials and Methods
The T-junction chips were prepared for droplet generation by affixing nanoport assemblies (Upchurch Scientific) as fluidic interfaces.

The droplet generation mechanism in a T-junction is well documented in the literature [Garstecki et al., Lab Chip, 2006, 6, 437-446 and Thorsen et al., Physical Review Letters, 2001, 86, 18, 4163-4166]. Taking into account the fluid viscosities of the reagents involved the chosen T-junction geometry was 50 µm channel width for both cases (oil and buffer).
1.1—Droplet Reagents In order to make aqueous phase droplets in oil, buffer was used as the disperse phase, while a silicon oil (e.g. AR20), was used as the continuous phase. Both buffer and triblock co-polymer-containing oil were prepared as described below.

A solution of buffer (buffer 1) was prepared by adding 298 mg of KCl (99.99% Purity, Sigma) to 10 mL of degassed DI water. To this solution 30.35 mg of 2-Amino-2-(hydroxymethyl)-1,3-propanediol (99.9%, Sigma) was added. The solution was buffered to pH 8 using small quantities of HCl and NaOH. 316.5 mg of $K_2[Fe(CN)_6]$ (99.9%, Sigma) and 82.3 mg of $K_3[Fe(CN)_6]$ (99.9%, Sigma) was added to the solution and stirred until dissolved.

Oil-triblock co-polymer solution was prepared by adding 20 mg of polymer (6-33-6, PMOXA-PDMS-PMOXA, PolymerSource) to 1 mL of AR20 (99%, Sigma). The polymer was left stirring in the oil for 24 hrs until all of the polymer had dissolved.
1.2—Droplet Generation Setup The droplet generation setup consisted of two syringe pumps (Elite, Harvard Apparatus), two gastight syringes (Hamilton), peak tubing (Upchurch Scientific), and a custom made T-junction microfluidic chip. Once the syringes were loaded with oil and buffer and mounted on the syringe pumps, the peak tubing was used to establish the fluidic connections to the ports on the chip. The oil syringe was connected to the continuous phase channel input while the buffer was connected to the disperse phase channel input.

Both syringe pumps were set to infuse at a flow rate of 10 µL/min, which produced an average droplet size (diameter) of 129.46 µm, with a standard deviation of 10.87 µm. The droplets were then collected in a vial.

EXAMPLE 2

This example describes the method used to produce droplet-interface-bilayers (DIBs) using a number of different tri-block co-polymers in different oils. The ability to form bilayers and to allow insertion of biological nanopores (such as mutants of MspA) was also investigated.
Materials and Methods Experiments 2.1, 2.3 and 2.4 were carried out on the below combinations of tri-block co-polymer and oil.

1—6-33-6 (PMOXA-PDMS-PMOXA) PolymerSource (20 mg/mL) in AR20 oil (polyphenyl-methylsiloxane, Sigma Aldrich).

2—6-33-6 (PMOXA-PDMS-PMOXA) PolymerSource (20 mg/mL) in PDMS-OH 65 cSt oil (poly(dimethylsiloxane), hydroxyl terminated, Sigma Aldrich).

3—6-45PE-6 (PMOXA-PE-PMOXA, where PE=a polyelethylene hydrocarbon chain approximately 45 carbon atoms in length.) PolymerSource (20 mg/mL) in hexadecane (99.9%, Sigma Aldrich).

4—6-32-6 (PMOXA-PDMS-PMOXA) HighForce (20 mg/mL) in AR20 oil (polyphenyl-methylsiloxane, Sigma Aldrich).

2.1—Droplet Stability Experiments

Droplet stability was measured off-line by preparing solutions of buffer and triblock ABA polymer in various oils. A small 0.5 cm' tray was prepared using polycarbonate and a glass slide. The tray was filled with oil. To the oil, 1 μL buffer droplets were added and monitored over 24 hrs. Droplets that exhibited only a small degree of merging were progressed to electrical DIBs testing.

2.2—Experimental Set-Up

The experimental system was as follows. A 700B axopatch was connected inside a shielded box containing two micro-manipulators. The entire faraday cage was placed on an inverted microscope (Nikon) such that it was possible to view the manipulation of the droplets from underneath. This allowed the droplets to be moved without opening the Faraday cage.

Within the Faraday cage, the electrodes of the 700B axopatch were connected via pure gold (Au) wire The Au was prepared for use in the droplet setup by flaming the end such that the wire formed a small gold bead. The Au wire was cleaned by emersion in conc.$HNO_3$ for 30 s, and washed thoroughly with DI water. The ball-ended wire was then repeatedly moved through a liquid agarose solution prepared from the buffer (5% wt low-melt agarose, Lonza/Buffer 400 mM KCl, 75 mM $K_2[Fe(CN)_6]$ (99.9%, Sigma) and 25 mM $K_3[Fe(CN)_6]$ (99.9%, Sigma), 10 mM Tris). Once a small bead had formed on the end the agarose was allowed to cool, and the wire was stored in an excess of buffer solution in order to come to equilibrium.

The droplet chamber was mounted on the stage within the Faraday cage, and the electrodes were mounted such that both fell within the central section of the chamber. The manipulators were situated such that a full range of movement in X and Y directions were achievable by both electrodes over the area of the chamber. The chamber was then filled to the brim with the AR20 tri-block co-polymer solution and allowed to stand for a few minutes. 1 μL of buffer was pipetted directly onto each of the agarose tipped Au wires and both electrodes were moved directly under the AR20/triblock co-polymer solution. The droplets were left under the solution for 30 s before movement.

2.3—Bilayer Formation

To form a membrane with the droplet pair, a waveform of ±20 mV was applied to the electrodes in addition to a bias voltage of 180 mV. The current response was monitored as the indicator of the formation of a capacitive membrane. The droplets were carefully brought together such that contact between the two buffer volumes was made. The droplets were left in this state until a membrane was formed. In situations where the membrane growth was very slow, the droplets were moved in the XY direction, which forced exclusion of the AR20/triblock co-polymer between the droplets and facilitated membrane growth.

2.4—Nanopore Insertion Experiments

In order to insert trans-membrane pores across the membrane, a 0.0005 mg/ml solution of MspA-(B2C) (SEQ ID NO: 1 and 9) was added to the buffer that formed the analyte. Insertion of the pore was observed by an instantaneous increase in current. This was performed in the absence of the waveform, but under the applied bias potential.

Results

The different tri-block co-polymer and oil combinations that were investigated are shown in Table 1 below.

TABLE 1

| Tri-Block Co-Polymer | Oil | Off-line Stability Test | Membrane Formation | MspA-(B2C) Pore Insertion |
|---|---|---|---|---|
| 6-33-6 PolymerSource | AR20 | stable droplets formed | capacitive membrane growth observed | pores inserted |
| 6-33-6 PolymerSource | PDMS-OH 65cSt | stable droplets formed | capacitive membrane growth observed | pores inserted |
| 6-45PE-6 PolymerSource | C16 | stable droplets formed | capacitive membrane growth observed | pores inserted |
| 6-32-6 HighForce | AR20 | stable droplets formed | capacitive membrane growth observed | pores inserted |

Capacitive membrane growth and pore insertion was observed for all of the tri-block co-polymer/oils tested. Membrane growth and MspA-(B2C) (SEQ ID NO: 1 and 9) pore insertion were observed for the 6-33-6 PolymerSource tri-block co-polymer used with AR20 silicone oil. Membrane growth and pore insertion were observed for the 6-45PE-6 PolymerSource used with hexadecane as an example of a triblock co-polymer which does not have the PDMS central core structure.

EXAMPLE 3

This example describes the method used to produce the array chips which are assembled with patterned interconnecting droplet zones.

Materials and Methods 3.1—Array Chip Formation 3.1.1 Array Chip Fabrication

The array chips were fabricated in clean-room facilities. A 6 in Si wafer with a 1 μm thermal oxide (SiMat) was used as a base for the support. The wafer was initially treated with 200 W, $O_2$ plasma in a plasma processor (Oxford Instruments), it then underwent a dehydration bake at 150° C. for 15 minutes in a hotplate (Electronic Micro Systems Ltd). The wafer was coated with a 1 μm layer of SU-8 2 photoresist (MicroChem Corp.) in a spin-coater (Electronic Micro Systems Ltd, 3000 rpm for 30 seconds), soft baked at 65° C. and 2 min at 95° C. in a hotplate, flood exposed (110 mJ/cm$^2$) in a UV mask aligner (Quintel Corp.) and then post-exposure baked (PEB) for 1 min at 65° C. followed by 2 min at 95° C. in a hotplate. The wafer was then spin-coated with a 120 μm thick layer of SU-8 3050 (1250 rpm for 30 s) and soft baked for 5 min at 65° C. followed by 2.5 h at 95° C. in a level hot plate. After cooling, it was exposed (260 mJ/cm$^2$) in the mask aligner using the photomask patterned with the microfluidic network. A PEB was then carried out: 2 min at 65° C. and 15 min at 95° C. The channel features were developed by immersion of the wafer in Microposit EC Solvent (Rhom Haas Electronic Materials), in an appropriately size beaker, and shaken for 10 min and finally rinsed. Once the channels had been formed, the wafer was treated with $O_2$ plasma for 1 min at 200 W to promote adhesion of the top layer and the SU-8 resist.

The channels were sealed with a layer of 100 μm thick film laminate resist, SUEX (DJ DevCorp) using a Exclam-Plus laminator (GMP) with the top roller set at 45° C., with a pressure setting at 1 mm thickness and a speed of 50 cm/min. A post lamination bake of 3 min at 65° C. was then carried out. After cooling, the SUEX layer was exposed (1400 mJ/cm$^2$) using the fluidic port mask. It should be noted that the protective polymer layer on the laminate was left on. The PEB was 3 min at 65° C. followed by 7 min at 95° C., again with the protective film on. The wafer was then developed using propylene glycol monomethyl ether acetate (Sigma-Aldrich) for 10 min and rinsed thoroughly with isopropanol, making sure the all residual developer was rinsed from the interior of the channels. The wafers were finally hard baked at 150° C. for 1 h and diced into individual chips.

3.1.2 Open Structure Array Chip Fabrication

The functional structure array chips were fabricated in clean-room facilities. A 6 inch Si wafer (Silex) containing bias and electrodes was used as substrate. The wafer was initially treated with 200 W, $O_2$ plasma in a plasma processor (Oxford Instruments), it then underwent a dehydration bake at 150° C. for 15 minutes in a hotplate (Electronic Micro Systems Ltd). The wafer was coated with a 1 μm layer of SU-8 2 photoresist (MicroChem Corp.) in a spin-coater (Electronic Micro Systems Ltd, 3000 rpm for 30 seconds), soft baked at 65° C. and 2 min at 95° C. in a hotplate, exposed (110 mJ/cm$^2$) in a UV mask aligner (Quintel Corp.) with a Seed layer mask. The wafer was then post-exposure baked (PEB) for 1 min at 65° C. followed by 2 min at 95° C. in a hotplate and developed in EC Solvent for 1 min. The Seed layer function was to improve adhesion of the high aspect ratio and it also ensured that only the desired area of the electrodes was exposed to solution.

A layer of dry-film resist TMMF 2030 (Tokyo Ohka Kogyo Co. Ltd.) was applied to the wafer using an Excelam-Plus roll laminator (GMP Co. Ltd.) with a top roll temperature of 85° C. The process was then repeated five times, to achieve a 150 μm thickness. The wafer was then exposed to UV in the mask aligner using a Pillar structure mask. A PEB at 95° C. was carried out in a hotplate for 10 min previous to development of the resist in EC Solvent for 12 min. The wafer was then treated with a 200 W $O_2$ plasma and hard baked in an oven at 200° C. for 1 h.

At this stage the wafer with the formed pillar structure was diced into individual devices and packaged onto ASIC-containing PCBs.

3.1.3 Closed Structure Array Chip Fabrication

This type of functional structure was fabricated in the same base substrate as the open structure array chip fabrication, i.e. a Silex wafer containing bias and electrodes. A Seed layer was formed in the same way as described in the previous section. Then the wafer was laminated with four layers of TMMF 2030 dry-film resist, with the same process parameters as described above. These four layers, with an overall thickness of 120 μm, were then exposed using the Wells mask. The wafer was subsequently laminated with a fifth layer of TMMF 2030 and exposed using the Pillars mask. The wafers then underwent a PEB at 95° C. for 10 min, were developed in EC Solvent for 12 min, 2 min $O_2$ plasma at 200 W and a hard bake at 200° C. for 1 h.

At this stage the wafer with the formed well and pillar structures, was diced into individual devices and packaged onto ASIC-containing PCBs.

EXAMPLE 4

This example describes the method used to populate the array chips, which were assembled with patterned interconnecting droplet zones, with tri-block copolymer droplets formed using the method detailed in Example 1.

Materials and Methods 4.1—Membrane Formation on Open Structure Arrays

To dispense the droplets onto the array of interconnecting droplet zones, a 1000 μL micro-pipette (Gibson) was used. The pipette tip was cut by 1 mm to, enlarge the orifice and prevent droplet merging due to shear stress. The droplets were then slowly dispensed onto the surface of the interconnecting droplet zones, ensuring that the entire area was cover with a large excess. Most of the excess droplet solution was then removed by inclining the array, in order to allow gravity to remove the excess droplets which had not been captured in the droplet zones. At this point, a flow cell large enough to fit the entire area of the array was placed on top of it, sealed and then filled with oil. This step was carried out because droplets can stick to one another and flushing the flow cell with oil removes the remaining droplets from the top of the capture array. Finally, tri-block co-polymer membranes were formed between each individual droplet and a common aqueous volume by flushing the bulk of the oil away and substituting it for an aqueous phase i.e. buffer 1. As the oil was displaced from the flow cell, the aqueous solution came into contact with the top part of the capture structure as well as the top of each droplet. The self assembled triblock copolymer layer prevented the two aqueous phases from merging; providing the droplet was big enough to be in contact with the bulk aqueous solution. The cross-section of the apparatus 1 is as shown in FIG. 31.

EXAMPLE 5

This example describes the insertion of MspA-(B2C) (SEQ ID NO: 1 and 9) pores into tri-block co-polymer droplets (6-33-6 PolymerSource droplets in AR20 (Sigma Aldrich) and helicase controlled DNA movement through the nanopore. The droplets used in these experiments were made of cross-linked agarose beads (Bio-Works) (140-150 μm) which had been coated in tri-block co-polymer in AR20 silicone oil.

Materials and Methods 5.1—Agarose Bead Preparation

The cross-linked agarose beads were obtained from Bio-Works in a broad range of sizes (130-250 μm). The droplets were then sieved using filters to obtain beads that were in the size range 140-150 μm and stored in pure water. The beads were then centrifuged and buffer exchanged (625 mM KCl, 75 mM potassium ferrocyanide, 25 mM potassium ferricyanide, 100 mM CAPS, pH 10.0) at least 5 times Immediately after the final buffer exchange and centrifuge step (to remove excess water) the beads were extracted and immersed in 10 mg/mL 6-33-6 PolymerSource triblock co-polymer in AR20 silicone oil. The beads were briefly vortexed for 30 sec in the oil, and left to stand for 1 hour.

5.2—Membrane Formation

Cross-linked agarose beads in 6-33-6 PolymerSource triblock co-polymer/AR20 were added to the array, and manually inserted into the interconnecting droplet zones Immediately after filling, a small amount of 10 mg/mL 6-33-6 PolymerSource triblock co-polymer/AR20 (~50 uL) was added to the surface of the array to immerse the beads and keep them under oil. They were incubated in this state for 5 mins. After this the chip was assembled and buffer (625 mM KCl, 75 mM potassium ferrocyanide, 25 mM potassium ferricyanide, 100 mM CAPS, pH 10.0) was immediately flowed through. The array was then ready for testing.

5.3—Pore Insertion and Helicase Controlled DNA Movement

In order for pores to insert into the triblock co-polymer, a solution of buffer (625 mM KCl, 75 mM potassium ferrocyanide, 25 mM potassium ferricyanide, 100 mM CAPS, pH 10.0) with MspA-(B2C) (SEQ ID NO: 1 and 9) was flowed over the array. A holding potential of +180 mV was applied and pores were allowed to enter bilayers until at least 10% occupancy was achieved. Once pores had inserted, then buffer solution (625 mM KCl, 75 mM potassium ferrocyanide, 25 mM potassium ferricyanide, 100 mM CAPS, pH 10.0) containing no MspA-(B2C) (SEQ ID NO: 1 and 9) was then flowed over the array to prevent further pores inserting into the tri-block co-polymer. In order to observe helicase-controlled DNA movement, a solution containing DNA (SEQ ID NO: 3 connected via 4 spacer groups to SEQ ID NO: 4, 1 nM), helicase enzyme (100 nM), dTTP (5 mM), $Mg^{2+}$ (10 mM) in buffer (625 mM KCl, 75 mM potassium ferrocyanide, 25 mM potassium ferricyanide, 100 mM CAPS, pH 10.0) was flowed over the array. A holding potential of +180 mV was applied and helicase-controlled DNA movement was observed.

Results

Upon the exposure of the tri-block co-polymer covered agarose droplets to MspA-(B2C) nanopores, insertion of the pores into the tri-block co-polymer were observed. On the addition of DNA (SEQ ID NO: 3 connected via 4 spacer groups to SEQ ID NO: 4, 1 nM) and helicase enzyme to the system, helicase controlled DNA translocation through the MspA-(B2C) nanopore was observed. Two example current traces showing helicase-controlled DNA movement through nanopores inserted into agarose droplets are shown in FIGS. 48A and B.

EXAMPLE 6

This example describes the insertion of alpha-hemolysin-(E111N/K147N)$_7$ (SEQ ID NO: 5 and 6) pores into tri-block co-polymer droplets (6-33-6 PolymerSource droplets in AR20 (Sigma Aldrich) and how this system was used to detect the presence of the protein thrombin. The droplets used in these experiments were made of low melt agarose.

Materials and Methods 6.1—Agarose Bead Preparation

The droplet generation setup consisted of two syringe pumps (Elite, Harvard Apparatus), two gastight syringes (Hamilton), peak tubing (Upchurch Scientific), and a custom made T-junction microfluidic chip. Once the syringes were loaded with 6-33-6 triblock copolymer in AR20 oil in one and 2% low melt agarose (Lonza) in buffer (625 mM KCl, 75 mM potassium ferrocyanide, 25 mM potassium ferricyanide, 100 mM CAPS, pH 10.0) in the other and mounted on the syringe pumps, the peak tubing was used to establish the fluidic connections to the ports on the chip. The oil syringe was connected to the continuous phase channel input while the buffer was connected to the disperse phase channel input. In order to make agarose droplets, the set-up was placed in an oven at 50° C. in order for the agarose solution to remain fluid during the droplet generation process.

Both syringe pumps were set to infuse at a flow rate of 10 μL/min for the agarose in buffer and 25 μL/min for the 6-33-6 in AR20 oil, which produced an average droplet size (diameter) of 150 μm, with a standard deviation of 5 μm. The droplets were then collected in a vial.

6.2—Membrane Formation

The tri-block co-polymer membrane was formed as described in Example 5.

6.3—Pore Insertion and Detection of the Protein Thrombin

In order for pores to insert into the triblock co-polymer, a solution of buffer (625 mM KCl, 75 mM potassium ferrocyanide, 25 mM potassium ferricyanide, 100 mM CAPS, pH 10.0) with alpha-hemolysin-(E111N/K147N)$_7$ (SEQ ID NO: 5 and 6) was flowed over the array. A holding potential of +180 mV was applied and pores were allowed to enter bilayers until at least 10% occupancy was achieved. Once pores had inserted, then buffer solution (625 mM KCl, 75 mM potassium ferrocyanide, 25 mM potassium ferricyanide, 100 mM CAPS, pH 10.0) containing no alpha-hemolysin-(E111N/K147N)$_7$ (SEQ ID NO: 5 and 6) was then flowed over the array to prevent further pores inserting into the tri-block co-polymer. In order to observe thrombin binding to an aptamer, a solution containing the aptamer (SEQ ID NO: 7, 1 μM) and thrombin (1 μM) in buffer (625 mM KCl, 75 mM potassium ferrocyanide, 25 mM potassium ferricyanide, 100 mM CAPS, pH 10.0) was flowed over the array. A holding potential of +180 mV was applied and characteristic block levels corresponding to the presence and absence of thrombin were detected.

Results

Upon the exposure of the tri-block co-polymer covered agarose droplets to alpha-hemolysin-(E111N/K147N)$_7$ (SEQ ID NO: 5 and 6) nanopores, insertion of the pores into the tri-block co-polymer was observed. On the addition of thrombin and aptamer (SEQ ID NO: 7) to the system, characteristic block levels corresponding to the presence and absence of thrombin were observed. Current traces were obtained showing the block produced in the absence of bound thrombin (1) and in the presence of thrombin (2), as shown in FIG. 49 which is a current trace (which is low-pass filtered) showing characteristic block levels corresponding to the presence (block labelled 2) and absence (block labelled 1).

EXAMPLE 7

This example describes how optical measurements were used to determine whether MspA-(B2C) (SEQ ID NO: 1 and 9) pores had inserted into triblock copolymer droplets.

Materials and Methods 7.1—Droplet Formation

With the ExoI/DNA buffer 1 (962.5 μM KCl, 7.5 mM potassium ferrocyanide, 2.5 mM potassium ferricyanide, 100 mM CAPS (pH10), 50 μM EDTA, 50 nM Eco ExoI, 5 μM FAM/BHQ1-labelled PolyT 30 mer (SEQ ID NO: 8)) and triblock copolymer (6-30-6) in AR20 oil in separate 1 mL Hamilton syringes, droplets were prepared by flowing at 16 μL/min (buffer 1) and 4 μL/min (triblock copolymer in oil), respectively through a Dolomite T-piece.

7.2—Array Population and Pore Insertion

Using a 200 μL pipette tip with the end cut off, 200 μL of droplets were pipette onto four clean arrays. Excess droplets were washed off with 2 mg/mL Triblock 6-30-6 in oil. 500 μL of buffer 2 (962.5 μM KCl, 7.5 mM potassium ferrocyanide, 2.5 mM potassium ferricyanide, 100 mM CAPS (pH10), 50 μM EDTA) was then flowed over each of the four arrays in order to cover the droplets. Brightfield images of each array were obtained using the fluorescence microscope.

Buffers 3 and 4 were then prepared as shown in the Table 2 below. Buffer 3 (which contained MspA-(B2C) nanopores) (500 µL) was flowed over two arrays and Buffer 4 (which contained no nanopores as a control) was flowed over the other two arrays. Buffer 3 and 4 were left on the arrays for 30 minutes before Mg2+ containing buffer (buffer 5-0.5 M $MgCl_2$, 100 mM CAPS, pH10, 7.5 mM potassium ferrocyanide, 2.5 mM potassium ferricyanide) was flowed across all four arrays. The arrays were then left overnight at room temperature before acquiring Brightfield and FITC (2 s exposure) images of each array using a 5× lens.

TABLE 2

|  | Buffer 3 | Buffer 4 |
| --- | --- | --- |
| MspA-(B2C) | 7.5 µL |  |
| Storage buffer | — | 7.5 µL |
| Buffer 2 | 1492.5 µL | 1492.5 µL |

Storage buffer = 50 mM Tris HCl, pH 9.0, 100 mM NaCl, 0.1% DDM

Results

This example describes how optical measurements can be used to determine whether MspA-(B2C) (SEQ ID NO: 1 and 9) pores have inserted into triblock copolymer droplets. MspA-(B2C) (SEQ ID NO: 1 and 9) pores were allowed to insert into triblock copolymer droplets, which contained ExoI enzyme and fluorphore/quencher-labeled DNA substrate (SEQ ID NO: 8). By subsequently flowing a $Mg^{2+}$-containing buffer across the top of the droplets, flow of $Mg^{2+}$ cations into the droplets, through inserted nanopores, activated the ExoI, allowing it to digest the fluorophore/quencher DNA, resulting in a fluorescence increase. The arrays that were treated with MspA-(B2C) (SEQ ID NO: 1 and 9) containing buffer (buffer 3) showed bright spots on the arrays which indicates that pores have inserted into the droplets, as shown in FIG. 50. FIG. 51 shows a control experiment where buffer which contained no MspA-(B2C) (SEQ ID NO: 1 and 9) (buffer 4) was used. The absence of bright spots shows that under control conditions (absence of MspA-(B2C) nanopores) $Mg^{2+}$ cannot penetrate the triblock copolymer, therefore, preventing activation of the enzyme and an increase in fluorescence. By comparison of FIG. 50 and FIG. 51 it is clear that the droplets which were exposed to buffer containing nanopores showed bright spots which corresponded to insertion of nanopores into the triblock copolymer.

EXAMPLE 8

This example describes the method used to populate the arrays, which were assembled with patterned interconnecting droplet zones.

Materials and Methods 8.2 Membrane Formation on Semi-Closed Structure Arrays

Using a micropipette, 50 µL of a 150 µL AR20/1 ml hexane mixture was dispensed onto the surface of a dry array at a temperature of 100° C. and left for 1 h to allow the oil to be distributed through the array surface by capillarity and for the hexane to evaporate. The array was mounted on an array holder and a 1.5 mm thick gasket was placed on it, aligned in such a way that the array was completely open and surrounded. The buffer intended to fill in each of the individual wells was then dispensed on top of the array (700 µL); the gasket should contain the buffer volume. The array was then placed in a vacuum chamber and pumped down to 25 mbar for 1 min such that volumes of buffer were provided in the wells It was then removed from the vacuum chamber and placed on a flow cell assembly clamp, where a flow cell was aligned to the holder and clamped to seal the assembly. An AR20 flow-front (700 µL) was then slowly pushed through the flow cell with a pipette; in this step the individual aqueous volumes contained within the wells were separated from the bulk and encapsulated in oil. This step was followed by a 5 mL air flow-front which displaced the excess oil out of the flow cell. The flow cell was then unclamped and disassembled allowing 30 µL of oil with a 10 mg/mL concentration of tri-block co-polymer (TBCP) to be dispensed on top of the array and left to incubate for 20 min. After the incubation step the excess oil was removed by placing the array at 90° and allowing it to flow off the array so it can be dried with a tissue. At this stage the aqueous volumes were ready to form TBCP membranes.

Once the wells had been filled with aqueous and TBCP had been introduced into the system the array was then assembled into an assay flow cell, where buffer was then introduced. As the buffer flow front travelled over the array, it displaced any excess oil left allowing the bulk buffer volume to form TBCP membranes.

EXAMPLE 9

This example describes the method used to populate arrays with volumes of polar and apolar media according to that shown in FIGS. 21 and 22 and as shown schematically FIG. 32.

Oil Pretreatment

An array was subjected to an oil preconditioning with a small amount of AR-20 silicone oil to fill the micro-patterning of the well and cover the pillars and surface in a thin oil film. A 1 mL syringe barrel of a Harvard syringe pump was primed with AR-20 oil and the dispense speed set to 2 µl/sec. 1.7 µl of AR20 silicone oil was dispensed onto the centre of a hexagonal close packed array of dimensions 6.04 mm×14.47 mm having 2048 compartments spaced with a pitch of 200 µm, a well height of 90 µm and a pillar height of 30 µm and allowed to spread through the array. The array was then subjected to 100 deg. C. in an oven for 30 mins and subsequently removed and allowed to cool. The array was inspected to ensure the oil had reached the edges of the array before use.

Buffer Filling 10 ml of buffer (600 mM KCl, 100 mM Hepes, 75 mM Potassium Ferrocyanide (II), 25 mM Potassium Ferricyanide (III), pH 8) was degassed and loaded into a flow-cell reservoir. The array was placed in the flow-cell as shown in FIG. 27 and the array was filled with buffer under vacuum (approx. 35 mBar) to provide volumes of buffer in the compartments.

Oil Filling

Immediately following the buffer filling step, 5 µl of 10 mg/ml TBCP/AR-20 was added to the flow-cell and flowed over the top of the array under vacuum. This was left to incubate for approx. 5 minute to ensure that the TBCP covered the entire array. Excess buffer was removed from the non-array areas and excess oil was removed from the array under vacuum.

Addition of Buffer Layer

Following the oil filling step, a further amount of buffer was flowed over the array in order to provide a buffer layer/TBCP/volume of buffer interface. The layer of buffer also minimises evaporation of water from the volumes of buffer in the compartments.

EXAMPLE 10

This example describes how the method used to populate the arrays described in Example 8 was modified in order to produce confocal microscopy images showing the uniform population of the interconnecting droplet zones and membrane formation. The images show that the aqueous volumes pinned to the walls of the wells resulting in the control of membrane size.

Materials and Methods

The various images described above were taken by confocal imaging. In order to render the materials involved in the experiments distinguishable in confocal microscopy, fluorescent dyes were diluted in the reagents. The oil (AR20) was dyed with BODIPY 493/503 (green) and the buffer solution, which formed the discrete volumes, was dyed with Sulforhodamine B (red). The remaining materials were not dyed and therefore appear as dark regions in the confocal images. In membrane formation experiments (shown in FIGS. 39 and 40) the incubation oil, with 10 mg/mL of TBCP, was also dyed with BODIPY 493/503. The bulk buffer which was flowed over the array after the first aqueous volume had pinned to the walls of the inner wells was not dyed. The confocal microscopy samples were prepared with the above reagents using the method described in the previous section (Example 8), and then imaged using a Nikon A1 Confocal Microscope.

The invention claimed is:

1. A method of forming an array of membranes comprising amphipathic molecules, the method comprising:
   providing an apparatus (1) comprising a support (3) that comprises partitions (6) defining an array of compartments (4), the partitions (6) comprising inner portions (20) and outer portions (21), the inner portions (20) defining inner recesses (22) without gaps therebetween that are capable of constraining volumes (2) comprising polar medium that may be contained in neighboring inner recesses (22) from contacting each other, and the outer portions (21) extending outwardly from the inner portions (20) and having gaps allowing the flow of an apolar medium between the compartments (4), whereby the compartments (4) have openings through which polar medium may be introduced;
   disposing polar medium and apolar medium onto the support (3) to provide volumes (2) comprising polar medium within respective compartments (4) so that the volumes (2) comprising polar medium are constrained from contacting volumes (2) comprising polar medium in neighboring compartments (4), and a layer comprising apolar medium extending across the openings in the support (3) in contact with the volumes (2) comprising polar medium; and
   flowing polar medium across the openings in the support (3) to displace apolar medium and form a layer (50) comprising polar medium extending across the openings in the support (3) in contact with the volumes (2) comprising polar medium and membranes comprising amphipathic molecules at the interfaces between the layer (50) comprising polar medium and the volumes (2) comprising polar medium.

2. A method according to claim 1, wherein the step of disposing polar medium and apolar medium onto the support (3) comprises:
   disposing polar medium onto the support (3) so that the polar medium enters into the compartments (4) through the openings; and
   subsequently providing said layer comprising apolar medium.

3. A method according to claim 2, wherein the step of disposing polar medium onto the support (3) comprises flowing polar medium across the support (3) so that the polar medium enters into the compartments (4) through the openings.

4. A method according to claim 3, wherein the step of disposing polar medium and apolar medium onto the support (3) comprises, between said step of flowing polar medium across the support (3) and said step of providing said layer comprising apolar medium, flowing a gas across the support (3) to displace excess polar medium, leaving the volumes (2) comprising polar medium in the compartments.

5. A method according to claim 4, wherein the step of providing said layer comprising apolar medium comprises flowing apolar medium across the support (3) to displace excess polar medium leaving the volumes (2) comprising polar medium in the compartments (4) and the layer comprising apolar medium extending across the openings in the support (3) in contact with the volumes (2) comprising polar medium.

6. A method according to claim 2, further comprising pre-treating the support (3) with a pre-treatment of apolar medium before said step of disposing polar medium and apolar medium onto the support (3).

7. A method according to claim 2, wherein the layer comprising apolar medium further comprises the amphipathic molecules or the polar medium that is flowed across the openings in the support (3) further comprises the amphipathic molecules.

* * * * *

SEQUENCE LISTING

```
<160> NUMBER OF SEQ ID NOS: 10

<210> SEQ ID NO 1
<211> LENGTH: 185
<212> TYPE: PRT
<213> ORGANISM: Artificial Sequence
<220> FEATURE:
<223> OTHER INFORMATION: MspA-B2C

<400> SEQUENCE: 1

Met Gly Leu Asp Asn Glu Leu Ser Leu Val Asp Gly Gln Asp Arg Thr
1               5                   10                  15

Leu Thr Val Gln Gln Trp Asp Thr Phe Leu Asn Gly Val Phe Pro Leu
            20                  25                  30

Asp Arg Asn Arg Leu Thr Arg Glu Trp Phe His Ser Gly Arg Ala Lys
        35                  40                  45

Tyr Ile Val Ala Gly Pro Gly Ala Asp Glu Phe Glu Gly Thr Leu Glu
    50                  55                  60

Leu Gly Tyr Gln Ile Gly Phe Pro Trp Ser Leu Ser Val Ser Ile Asn
65                  70                  75                  80

Phe Ser Tyr Thr Thr Pro Asn Ile Asn Ile Asn Asn Gly Asn Ile Thr
                85                  90                  95

Ala Pro Pro Phe Gly Leu Asn Ser Val Ile Thr Pro Asn Leu Phe Pro
            100                 105                 110

Gly Val Ser Ile Ser Ala Arg Leu Gly Asn Gly Pro Gly Ile Arg Glu
        115                 120                 125

Val Ala Thr Phe Ser Val Arg Val Ser Gly Ala Lys Gly Gly Val Ala
    130                 135                 140

Val Ser Asn Ala His Gly Thr Val Thr Gly Ala Ala Gly Gly Val Leu
145                 150                 155                 160

Leu Arg Pro Phe Ala Arg Leu Ile Ala Ser Thr Gly Asp Ser Val Thr
                165                 170                 175

Thr Tyr Gly Glu Pro Trp Asn Met Asn
            180                 185

<210> SEQ ID NO 2
<211> LENGTH: 184
<212> TYPE: PRT
<213> ORGANISM: Artificial Sequence
<220> FEATURE:
<223> OTHER INFORMATION: MS-B1 mutant

<400> SEQUENCE: 2
```

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
            115                 120                 125

Ala Thr Phe Ser Val Arg Val Ser Gly Ala Lys Gly Gly Val Ala Val
        130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 77
<212> TYPE: DNA
<213> ORGANISM: Artificial Sequence
<220> FEATURE:
<223> OTHER INFORMATION: polynucleotide sequence used in Example 5

<400> SEQUENCE: 3
tttttttttt tttttttttt tttttttttt tttttttttt tttttttttt ggttgtttct    60
gttggtgctg atattgc                                                    77

<210> SEQ ID NO 4
<211> LENGTH: 530
<212> TYPE: DNA
<213> ORGANISM: Artificial Sequence
<220> FEATURE:
<223> OTHER INFORMATION: polynucleotide sequence used in Example 5

<400> SEQUENCE: 4
gacgctcagt aatgtgacga tagctgaaaa ctgtacgata acggtacgc tgagggcgga     60 aaaaatcgtc ggggacattg taaaggcggc gagcgcggct tttccgcgcc agcgtgaaag   120
cagtgtggac tggccgtcag gtacccgtac tgtcaccgtg accgatgacc atccttttga   180
tcgccagata gtggtgcttc cgctgacgtt tcgcggaagt aagcgtactg tcagcggcag   240
gacaacgtat tcgatgtgtt atctgaaagt actgatgaac ggtgcggtga tttatgatgg   300
cgcggcgaac gaggcggtac aggtgttctc ccgtattgtt gacatgccag cgggtcgggg   360
aaacgtgatc ctgacgttca cgcttacgtc cacacggcat tcggcagata ttccgccgta   420
tacgtttgcc agcgatgtgc aggttatggt gattaagaaa caggcgctgg gcatcagcgt   480
ggtctgagtg tgaaaaaaaa aaccccaaaa aaaaaccccc aaaaaaaaaa              530
```

-continued

<210> SEQ ID NO 5
<211> LENGTH: 885
<212> TYPE: DNA
<213> ORGANISM: Artificial Sequence
<220> FEATURE:
<223> OTHER INFORMATION: polynucleotide encoding one subunit of
    alpha-hemolysin-E111N/K147N

<400> SEQUENCE: 5

| | | |
|---|---|---|
| atggcagatt ctgatattaa tattaaaacc ggtactacag atattggaag caatactaca | 60 |
| gtaaaaacag gtgatttagt cacttatgat aaagaaaatg gcatgcacaa aaaagtattt | 120 |
| tatagtttta tcgatgataa aaatcacaat aaaaaaactgc tagttattag aacaaaaggt | 180 |
| accattgctg gtcaatatag agtttatagc gaagaaggtg ctaacaaaag tggtttagcc | 240 |
| tggccttcag cctttaaggt acagttgcaa ctacctgata tgaagtagc tcaaatatct | 300 |
| gattactatc caagaaattc gattgataca aaaaactata tgagtacttt aacttatgga | 360 |
| ttcaacggta atgttactgg tgatgataca ggaaaaattg gcggcttat tggtgcaaat | 420 |
| gtttcgattg gtcatacact gaactatgtt caacctgatt tcaaaacaat tttagagagc | 480 |
| ccaactgata aaaagtagg ctggaaagtg atatttaaca atatggtgaa tcaaaattgg | 540 |
| ggaccatacg atcgagattc ttggaacccg gtatatggca atcaacttttt catgaaaact | 600 |
| agaaatggtt ctatgaaagc agcagataac ttccttgatc ctaacaaagc aagttctcta | 660 |
| ttatcttcag ggttttcacc agacttcgct acagttatta ctatggatag aaaagcatcc | 720 |
| aaacaacaaa caaatataga tgtaatatac gaacgagttc gtgatgatta ccaattgcat | 780 |
| tggacttcaa caaattggaa aggtaccaat actaaagata aatggacaga tcgttcttca | 840 |
| gaaagatata aaatcgattg ggaaaaagaa gaaatgacaa attaa | 885 |

<210> SEQ ID NO 6
<211> LENGTH: 293
<212> TYPE: PRT
<213> ORGANISM: Artificial Sequence
<220> FEATURE:
<223> OTHER INFORMATION: amino acid sequence of one subunit of alpha-
    hemolysin-E111N/K147N

<400> SEQUENCE: 6

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro

```
               145                 150                 155                 160
       Thr Asp Lys Lys Val Gly Trp Lys Val Ile Phe Asn Asn Met Val Asn
                       165                 170                 175

Gln Asn Trp Gly Pro Tyr Asp Arg Asp Ser Trp Asn Pro Val Tyr Gly
                       180                 185                 190

Asn Gln Leu Phe Met Lys Thr Arg Asn Gly Ser Met Lys Ala Ala Asp
                       195                 200                 205

Asn Phe Leu Asp Pro Asn Lys Ala Ser Ser Leu Leu Ser Ser Gly Phe
           210                 215                 220

Ser Pro Asp Phe Ala Thr Val Ile Thr Met Asp Arg Lys Ala Ser Lys
       225                 230                 235                 240

Gln Gln Thr Asn Ile Asp Val Ile Tyr Glu Arg Val Arg Asp Asp Tyr
                       245                 250                 255

Gln Leu His Trp Thr Ser Thr Asn Trp Lys Gly Thr Asn Thr Lys Asp
                       260                 265                 270

Lys Trp Thr Asp Arg Ser Ser Glu Arg Tyr Lys Ile Asp Trp Glu Lys
                       275                 280                 285

Glu Glu Met Thr Asn
           290

<210> SEQ ID NO 7

<400> SEQUENCE: 7

000

<210> SEQ ID NO 8
<211> LENGTH: 30
<212> TYPE: DNA
<213> ORGANISM: Artificial Sequence
<220> FEATURE:
<223> OTHER INFORMATION: labelled polynucleotide strand
<220> FEATURE:
<221> NAME/KEY: MISC_FEATURE
<222> LOCATION: (1)..(1)
<223> OTHER INFORMATION: BHQ1 label
<220> FEATURE:
<221> NAME/KEY: MISC_FEATURE
<222> LOCATION: (15)..(15)
<223> OTHER INFORMATION: FAM label

<400> SEQUENCE: 8
tttttttttt tttttttttt tttttttttt                                     30

<210> SEQ ID NO 9
<211> LENGTH: 555
<212> TYPE: DNA
<213> ORGANISM: Artificial Sequence
<220> FEATURE:
<223> OTHER INFORMATION: polynucleotide sequence encoding the MspA-(B2C)
      mutant MspA monomer

<400> SEQUENCE: 9
atgggtctgg ataatgaact gagcctggtg acgggtcaag atcgtacccct gacggtgcaa      60 caatgggata ccttttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgagcgt tagtatcaac     240
ttctcgtaca ccacgccgaa tattaacatc aacaatggta acattaccgc accgccgttt     300
ggcctgaaca gcgtgattac gccgaacctg tttccgggtg ttagcatctc tgcccgtctg     360
```

```
ggcaatggtc cgggcattcg cgaagtggca acctttagtg tgcgcgtttc cggcgctaaa        420
ggcggtgtcg cggtgtctaa cgcccacggt accgttacgg gcgcggccgg cggtgtcctg        480
ctgcgtccgt tcgcgcgcct gattgcctct accggcgaca gcgttacgac ctatggcgaa        540
ccgtggaata tgaac                                                         555

<210> SEQ ID NO 10
<211> LENGTH: 558
<212> TYPE: DNA
<213> ORGANISM: Artificial Sequence
<220> FEATURE:
<223> OTHER INFORMATION: polynucleotide sequence encoding the MS-B1
      mutant of the MspA monomer

<400> SEQUENCE: 10
atgggtctgg ataatgaact gagcctggtg gacggtcaag atcgtaccct gacggtgcaa         60
caatgggata cctttctgaa tggcgttttt ccgctggatc gtaatcgcct gacccgtgaa        120
tggtttcatt ccggtcgcgc aaaatatatc gtcgcaggcc cgggtgctga cgaattcgaa        180
ggcacgctgg aactgggtta tcagattggc tttccgtggt cactgggcgt tggtatcaac        240
ttctcgtaca ccacgccgaa tattctgatc aacaatggta acattaccgc accgccgttt        300
ggcctgaaca gcgtgattac gccgaacctg tttccgggtg ttagcatctc tgcccgtctg        360
ggcaatggtc cgggcattca agaagtggca acctttagtg tgcgcgtttc cggcgctaaa        420
ggcggtgtcg cggtgtctaa cgcccacggt accgttacgg gcgcggccgg cggtgtcctg        480
ctgcgtccgt tcgcgcgcct gattgcctct accggcgaca gcgttacgac ctatggcgaa        540
ccgtggaata tgaactaa                                                      558
```